US011072764B2

(12) United States Patent
Bettiol et al.

(10) Patent No.: US 11,072,764 B2
(45) Date of Patent: Jul. 27, 2021

(54) DETERGENT COMPOSITION

(71) Applicant: The Procter & Gamble Company, Cincinnati, OH (US)

(72) Inventors: Jean-Luc Philippe Bettiol, Etterbeek (BE); Denis Alfred Gonzales, Brussels (BE); Juan Esteban Velasquez, Cincinnati, OH (US); Nicholas William Geary, Mariemont, OH (US)

(73) Assignee: The Procter & Gamble Company, Cincinnati, OH (US)

(*) Notice: Subject to any disclaimer, the term of this patent is extended or adjusted under 35 U.S.C. 154(b) by 37 days.

(21) Appl. No.: 16/188,624

(22) Filed: Nov. 13, 2018

(65) Prior Publication Data
US 2019/0144790 A1 May 16, 2019

(30) Foreign Application Priority Data

Nov. 13, 2017 (EP) .................... 17201309
Oct. 8, 2018 (EP) .................... 18199086

(51) Int. Cl.
| | | |
|---|---|---|
| C11D 3/386 | (2006.01) | |
| C11D 9/40 | (2006.01) | |
| C11D 9/26 | (2006.01) | |
| C12N 9/04 | (2006.01) | |
| C12N 9/88 | (2006.01) | |
| C11D 1/83 | (2006.01) | |
| C11D 11/00 | (2006.01) | |
| C11D 1/94 | (2006.01) | |
| C12N 9/02 | (2006.01) | |
| C11D 1/90 | (2006.01) | |
| C11D 1/75 | (2006.01) | |
| C11D 1/12 | (2006.01) | |

(52) U.S. Cl.
CPC ............ *C11D 3/386* (2013.01); *C11D 1/83* (2013.01); *C11D 1/94* (2013.01); *C11D 3/38654* (2013.01); *C11D 9/267* (2013.01); *C11D 9/40* (2013.01); *C11D 11/0023* (2013.01); *C12N 9/0006* (2013.01); *C12N 9/0069* (2013.01); *C12N 9/88* (2013.01); *C07K 2319/00* (2013.01); *C07K 2319/21* (2013.01); *C11D 1/12* (2013.01); *C11D 1/75* (2013.01); *C11D 1/90* (2013.01); *C12Y 111/01003* (2013.01); *C12Y 111/02001* (2013.01); *C12Y 111/02002* (2013.01); *C12Y 111/02003* (2013.01); *C12Y 111/02004* (2013.01); *C12Y 113/1106* (2013.01); *C12Y 113/11034* (2013.01); *C12Y 113/11044* (2013.01); *C12Y 113/11058* (2013.01); *C12Y 113/11062* (2013.01); *C12Y 114/15003* (2013.01); *C12Y 305/01099* (2013.01); *C12Y 402/01053* (2013.01); *C12Y 402/01092* (2013.01); *C12Y 502/01005* (2013.01); *C12Y 504/04005* (2013.01); *C12Y 504/04006* (2013.01)

(58) Field of Classification Search
None
See application file for complete search history.

(56) References Cited

U.S. PATENT DOCUMENTS

| | | | |
|---|---|---|---|
| 6,699,828 B1* | 3/2004 | de Buzzaccarini .. | C11D 3/0052 510/310 |
| 7,264,954 B2* | 9/2007 | Sugio .................... | A21D 8/042 426/20 |
| 7,321,025 B2 | 1/2008 | Feussner | |
| 2003/0166485 A1 | 9/2003 | Hage | |
| 2006/0073994 A1* | 4/2006 | Hage ................... | C11D 3/38627 510/101 |
| 2011/0015109 A1 | 1/2011 | Brooker | |
| 2014/0073547 A1* | 3/2014 | Meek .................... | C11D 3/046 510/218 |
| 2017/0321160 A1 | 11/2017 | Lant | |
| 2017/0321161 A1 | 11/2017 | Lant | |
| 2017/0321162 A1 | 11/2017 | Lant | |
| 2019/0144789 A1 | 5/2019 | Bettiol | |
| 2019/0144791 A1 | 5/2019 | Bettiol | |

FOREIGN PATENT DOCUMENTS

| | | |
|---|---|---|
| WO | WO9526393 A1 | 10/1995 |
| WO | 0029540 A1 | 5/2000 |
| WO | WO02086114 A1 | 10/2002 |
| WO | WO2014081700 A1 | 5/2014 |

OTHER PUBLICATIONS

Liu, W; et al; "Arabidopsis thaliana fatty acid alpha-dioxygenase-1: evaluation of substrates, inhibitors and amino-terminal function" Plant Physiology and Biochemistry, 44, 284-293, 2006 (Year: 2006).*
Authors et al.: Disclosed Anonymously—IP.com—Water Soluble Film Flakes Incorporating Functional Ingredients, an IP.com prior Art Database Technical Disclosure, 73 pages, IP Electronic Publication: Jan. 2, 2014.
Chen, Yang, et al.—Purification and site-directed mutagenesis of linoleate 9S-dioxygenase-allene oxide synthase of Fusarium oxysporum confirms the oxygenation mechanism, Archives of Biochemistry and Biophysics, vol. 625-626, Jul. 1, 2017, 6 pages.
Estupinan, Monica, et al.—Unveiling the Genes Responsible for the Unique Pseudomonas Aeruginosa Oleate-diol Synthase Activity, Biochimica et Biophysica Acta (BBA) Molecular and Cell Biology of Lipids, vol. 1841, No. 10, Oct. 1, 2014, 12 pages.

(Continued)

Primary Examiner — David W Berke-Schlessel
(74) Attorney, Agent, or Firm — Melissa G Krasovec

(57) ABSTRACT

A liquid detergent composition, preferably a liquid manual dishwashing detergent composition, comprising one or more hydroperoxy fatty acid producing enzymes selected from the group consisting of: arachidonate lipoxygenases, alpha-dioxygenases, and mixtures thereof, preferably alpha-dioxygenases, a surfactant system and a liquid carrier (i.e., water). Methods of washing comprising the liquid detergent composition are also provided.

17 Claims, No Drawings
Specification includes a Sequence Listing.

(56) References Cited

OTHER PUBLICATIONS

Extended European Search Report for Application No./Patent No. 17201309.6-1105, dated Sep. 28, 2018, 14 pages.
Extended European Search Report for Application No./Patent No. 18199086.2-1105, dated Jan. 24, 2019, 9 pages.
Gilbert, Nathaniel, et al.—A Covalent Linker Allows for Membrane Targeting of an Oxylipin Biosynthetic Complex, Biochemistry, vol. 47, No. 40, Oct. 7, 2008, 12 pages.
Hamberg, Mats, et al.—Fatty Acid x-Dioxygenases, Prostaglandins & other Lipid Mediatiors, 68-69 (2002) pp. 363-374.
International Search Report for International Application Serial No. PCT/US2018/059733, dated Feb. 28, 2019, 16 pages.
Noordermeer, Minke A., et al.—Development of a Biocatalytic Process for the Production of C6-Aldehydes from Vegetable Oils by Soybean Lipoxygenase and Recombinant Hydroperoxide Lyase, Journal of Agricultural and Food Chemistry, vol. 50, No. 15, Jul. 1, 2002, 5 pages.
All Office Actions, U.S. Appl. No. 16/188,637.
Branden et al., Introduction to Protein Structure, Garland Publishing Inc., New York, p. 247, dated, 1991.
Eriel Martinez et al. "Biochemical Characterization of the Oxygenation of Unsatured Fatty Acids by the Dioxygenase andHydroperoxide Isomerase of Pseudonomas aeruginosa 42A2", The Journal of Biological Chemistry vol. 285, Issue No. 13, Mar. 26, 2010, pp. 9339-9345.
Extended European Search Report and Search Opinion; Application Ser. No. 18199084.7; dated Jan. 24, 2019, 11 pages.
Extended European Search Report and Search Opinion; Application Ser. No. 18199093.8; dated Feb. 22, 2019, 10 pages.
Gallagher, S. Protocols in Molecular Biology, Gallagher, S., Current Protocols in Molecular Biology, One-Dimensional SOS Gel Electrophoresis of Proteins, vol. 75, Issue 1, pp. 10.2.1-10.2A.37, dated Jul. 2006.
Gottesman, S., Annual Reviews of Genetics 30:465-506, dated,1996.
International Search Report and Written Opinion; Application Serial No. PCT/U52018/059732; dated Feb. 28, 2019; 12 pages.
International Search Report and Written Opinion; Application Serial No. PCT/U52018/059735; dated Jan. 29, 2019; 12 pages.
Raha et al. Journal of Bacteriology 17 4(20):6644-6652, dated, 1992.
Sadowski et al., Current Opinion in Structural Biology 19:357-362, dated 2009.
Seffemick et al., J. Bacterial. 183(8) :2405-2410, dated, 2001.
Tang et al., Phil Trans R Soc B 368:20120318, 1-10, dated 2013.
Witkowski et al., Biochemistry 38:11643-11650, dated ,1999.

* cited by examiner

SEQUENCE LISTING

```
<160> NUMBER OF SEQ ID NOS: 23

<210> SEQ ID NO 1
<211> LENGTH: 639
<212> TYPE: PRT
<213> ORGANISM: Arabidopsis thaliana

<400> SEQUENCE: 1

Met Lys Val Ile Thr Ser Leu Ile Ser Ser Ile Leu Leu Lys Phe Ile
1               5                   10                  15

His Lys Asp Phe His Glu Ile Tyr Ala Arg Met Ser Leu Leu Asp Arg
            20                  25                  30

Phe Leu Leu Leu Ile Val His Gly Val Asp Lys Met Val Pro Trp His
        35                  40                  45

Lys Leu Pro Val Phe Leu Gly Leu Thr Tyr Leu Glu Val Arg Arg His
    50                  55                  60

Leu His Gln Gln Tyr Asn Leu Leu Asn Val Gly Gln Thr Pro Thr Gly
65                  70                  75                  80

Ile Arg Phe Asp Pro Ala Asn Tyr Pro Tyr Arg Thr Ala Asp Gly Lys
                85                  90                  95

Phe Asn Asp Pro Phe Asn Glu Gly Val Gly Ser Gln Asn Ser Phe Phe
            100                 105                 110
```

```
Gly Arg Asn Cys Pro Pro Val Asp Gln Lys Ser Lys Leu Arg Arg Pro
            115                 120                 125

Asp Pro Met Val Val Ala Thr Lys Leu Leu Gly Arg Lys Lys Phe Ile
130                 135                 140

Asp Thr Gly Lys Gln Phe Asn Met Ile Ala Ala Ser Trp Ile Gln Phe
145                 150                 155                 160

Met Ile His Asp Trp Ile Asp His Leu Glu Asp Thr His Gln Ile Glu
            165                 170                 175

Leu Val Ala Pro Lys Glu Val Ala Ser Lys Cys Pro Leu Ser Ser Phe
            180                 185                 190

Arg Phe Leu Lys Thr Lys Glu Val Pro Thr Gly Phe Phe Glu Ile Lys
            195                 200                 205

Thr Gly Ser Gln Asn Ile Arg Thr Pro Trp Trp Asp Ser Ser Val Ile
            210                 215                 220

Tyr Gly Ser Asn Ser Lys Thr Leu Asp Arg Val Arg Thr Tyr Lys Asp
225                 230                 235                 240

Gly Lys Leu Lys Ile Ser Glu Glu Thr Gly Leu Leu His Asp Glu
            245                 250                 255

Asp Gly Leu Ala Ile Ser Gly Asp Ile Arg Asn Ser Trp Ala Gly Val
            260                 265                 270

Ser Ala Leu Gln Ala Leu Phe Ile Lys Glu His Asn Ala Val Cys Asp
            275                 280                 285

Ala Leu Lys Asp Glu Asp Asp Leu Glu Asp Glu Asp Leu Tyr Arg
            290                 295                 300

Tyr Ala Arg Leu Val Thr Ser Ala Val Val Ala Lys Ile His Thr Ile
305                 310                 315                 320

Asp Trp Thr Val Gln Leu Leu Lys Thr Asp Thr Leu Leu Ala Gly Met
            325                 330                 335

Arg Ala Asn Trp Tyr Gly Leu Leu Gly Lys Lys Phe Lys Asp Ser Phe
            340                 345                 350

Gly His Ala Gly Ser Ser Ile Leu Gly Gly Val Val Gly Met Lys Lys
            355                 360                 365

Pro Gln Asn His Gly Val Pro Tyr Ser Leu Thr Glu Asp Phe Thr Ser
            370                 375                 380

Val Tyr Arg Met His Ser Leu Leu Pro Asp Gln Leu His Ile Leu Asp
385                 390                 395                 400

Ile Asp Asp Val Pro Gly Thr Asn Lys Ser Leu Pro Leu Ile Gln Glu
            405                 410                 415

Ile Ser Met Arg Asp Leu Ile Gly Arg Lys Gly Glu Glu Thr Met Ser
            420                 425                 430

His Ile Gly Phe Thr Lys Leu Met Val Ser Met Gly His Gln Ala Ser
            435                 440                 445

Gly Ala Leu Glu Leu Met Asn Tyr Pro Met Trp Leu Arg Asp Ile Val
450                 455                 460

Pro His Asp Pro Asn Gly Gln Ala Arg Pro His Val Asp Leu Ala
465                 470                 475                 480

Ala Leu Glu Ile Tyr Arg Asp Arg Glu Arg Ser Val Pro Arg Tyr Asn
            485                 490                 495

Glu Phe Arg Arg Ser Met Phe Met Ile Pro Ile Thr Lys Trp Glu Asp
            500                 505                 510

Leu Thr Glu Asp Glu Glu Ala Ile Glu Val Leu Asp Asp Val Tyr Asp
            515                 520                 525
```

```
Gly Asp Val Glu Glu Leu Asp Leu Val Gly Leu Met Ala Glu Lys
            530                 535                 540

Lys Ile Lys Gly Phe Ala Ile Ser Glu Thr Ala Phe Tyr Ile Phe Leu
545                 550                 555                 560

Ile Met Ala Thr Arg Arg Leu Glu Ala Asp Arg Phe Phe Thr Ser Asp
                565                 570                 575

Phe Asn Glu Thr Ile Tyr Thr Lys Lys Gly Leu Glu Trp Val Asn Thr
                580                 585                 590

Thr Glu Ser Leu Lys Asp Val Ile Asp Arg His Tyr Pro Asp Met Thr
                595                 600                 605

Asp Lys Trp Met Asn Ser Glu Ser Ala Phe Ser Val Trp Asp Ser Pro
            610                 615                 620

Pro Leu Thr Lys Asn Pro Ile Pro Leu Tyr Leu Arg Ile Pro Ser
625                 630                 635

<210> SEQ ID NO 2
<211> LENGTH: 631
<212> TYPE: PRT
<213> ORGANISM: Arabidopsis thaliana

<400> SEQUENCE: 2

Met Gly Phe Ser Pro Ser Ser Ser Trp Phe Leu His Pro Gln Leu His
1               5                   10                  15

His Val Val Ser Lys Met Ser Tyr Phe Asp Ala Phe Leu Phe Tyr Ile
                20                  25                  30

Val His Leu Val Asp Lys Leu Gly Leu Trp His Arg Phe Pro Val Leu
            35                  40                  45

Leu Gly Val Ala Tyr Leu Gly Leu Arg Arg His Leu His Gln Arg Tyr
    50                  55                  60

Asn Leu Val His Val Gly Pro Ile Asn Gly Gln Gly Tyr Asp Thr Asp
65                  70                  75                  80

Glu Phe Cys Tyr Arg Thr Ala Asp Gly Lys Cys Asn His Pro Ser Asp
                85                  90                  95

Asn Thr Ile Gly Ser Gln Gly Ser Phe Ile Gly Arg Asn Met Pro Pro
            100                 105                 110

Ser Thr Ser Gln Tyr Gly Ile Leu Asp Pro His Pro Ser Val Val Ala
        115                 120                 125

Thr Lys Leu Leu Ala Arg Lys Arg Phe Ile Asp Asn Gly Asp Gln Phe
    130                 135                 140

Asn Val Ile Ala Cys Ser Trp Ile Gln Phe Met Ile His Asp Trp Val
145                 150                 155                 160

Asp His Leu Glu Asp Thr His Gln Ile Glu Leu Glu Ala Pro Glu Glu
                165                 170                 175

Val Ala Ser Gly Cys Pro Leu Lys Ser Phe Lys Phe Leu Arg Thr Lys
            180                 185                 190

Lys Val Pro Thr Asp Asp His His Lys Ser Gly Ala Val Asn Thr Arg
        195                 200                 205

Thr Pro Trp Trp Asp Gly Ser Val Ile Tyr Gly Asn Asp Glu Thr Gly
    210                 215                 220

Met Arg Arg Val Arg Val Phe Lys Asp Gly Lys Leu Lys Ile Ser Gly
225                 230                 235                 240

Asp Gly Leu Leu Glu Arg Asp Glu Arg Gly Val Pro Ile Ser Gly Asp
                245                 250                 255

Ile Arg Asn Ser Trp Ser Gly Phe Ser Leu Leu Gln Ala Leu Phe Val
            260                 265                 270
```

```
Lys Glu His Asn Ser Val Cys Asp Met Leu Lys Glu Arg Tyr Pro Asp
        275                 280                 285

Phe Asp Asp Glu Lys Leu Tyr Arg Thr Ala Arg Leu Val Thr Ala Ala
290                 295                 300

Val Ile Ala Lys Val His Thr Ile Asp Trp Thr Ile Glu Leu Leu Lys
305                 310                 315                 320

Thr Asp Thr Leu Thr Ala Gly Met Arg Ile Asn Trp Tyr Gly Phe Phe
                325                 330                 335

Gly Lys Lys Val Lys Asp Met Val Gly Ala Arg Phe Gly Pro Leu Phe
                340                 345                 350

Ser Gly Leu Val Gly Leu Lys Lys Pro Asn Asp His Gly Val Pro Tyr
                355                 360                 365

Ser Leu Thr Glu Glu Phe Val Ser Val Tyr Arg Met His Cys Leu Leu
370                 375                 380

Pro Glu Thr Leu Ile Leu Arg Asp Met Asn Ser Glu Asn Val Asp Lys
385                 390                 395                 400

Glu Asn Pro Ala Ile Glu Arg Glu Ile Pro Met Thr Glu Leu Ile Gly
                405                 410                 415

Lys Lys Ala Gly Glu Lys Ala Ser Lys Leu Gly Phe Glu Gln Leu Leu
                420                 425                 430

Val Ser Met Gly His Gln Ser Cys Gly Ala Leu Thr Leu Trp Asn Tyr
                435                 440                 445

Pro Asn Trp Met Arg Asn Leu Val Ala Gln Asp Ile Asp Gly Glu Asp
                450                 455                 460

Arg Pro His Leu Ile Asp Met Ala Ala Leu Glu Ile Tyr Arg Asp Arg
465                 470                 475                 480

Glu Arg Gly Val Pro Arg Tyr Asn Glu Phe Arg Lys Asn Leu Leu Met
                485                 490                 495

Ser Pro Ile Ser Lys Trp Glu Glu Leu Thr Asp Asp Glu Glu Ala Ile
                500                 505                 510

Lys Val Leu Arg Glu Val Tyr Glu Asp Ile Glu Lys Leu Asp Leu
515                 520                 525

Asn Val Gly Leu His Ala Glu Lys Lys Ile Lys Gly Phe Ala Ile Ser
530                 535                 540

Glu Thr Ala Phe Phe Ile Phe Leu Leu Val Ala Ser Arg Arg Leu Glu
545                 550                 555                 560

Ala Asp Arg Phe Phe Thr Thr Asn Phe Asn Glu Lys Thr Tyr Thr Lys
                565                 570                 575

Glu Gly Leu Glu Trp Val Asn Thr Thr Glu Thr Leu Lys Asp Val Ile
                580                 585                 590

Asp Arg His Phe Pro Arg Leu Thr Asp Gln Trp Met Arg Cys Ser Ser
                595                 600                 605

Ala Phe Ser Val Trp Gly Ser Asp Pro Asn Pro Lys Asn Trp Val Pro
610                 615                 620

Leu Tyr Leu Arg Ser Ala Pro
625                 630

<210> SEQ ID NO 3
<211> LENGTH: 613
<212> TYPE: PRT
<213> ORGANISM: Fusarium graminearum

<400> SEQUENCE: 3

Met Ala Ser Val Thr Ser Ile Ile Phe Val Ala Leu Val Ala Gly Val
```

-continued

```
1               5                   10                  15
Leu Tyr Ala Ala Arg Met Ser Leu Val Pro Ile Leu Lys Ser Leu Tyr
                20                  25                  30
Ile Arg Leu Trp Lys Gly Val Asn His Phe Ile Glu Trp His Lys Leu
                35                  40                  45
Pro Thr Trp Phe Ala Val Phe Asn Leu Leu Ala Leu Arg Tyr Glu Leu
                50                  55                  60
Arg Glu Gly Asn Leu His Asp Thr Ser Pro Asn Ala Glu Phe Gln Gly
65                  70                  75                  80
Thr Asp Lys Cys Pro Met Ser Asp Ser Lys Phe Val Ser Ser Arg Asp
                85                  90                  95
Ser Asp Gly Leu Tyr Asn Asp Leu Lys Gln Pro Lys Met Gly Cys Ala
                100                 105                 110
Gly Met Arg Phe Gly Arg Asn Val Pro Arg Lys Tyr Thr Lys Pro Pro
                115                 120                 125
Thr Glu Gln Glu Leu Leu Thr Pro Asn Pro Arg Val Ile Ser Glu Lys
                130                 135                 140
Ile Leu Ala Arg Pro Glu Gly Gln Phe Lys Pro Ala Glu Ile Val Asn
145                 150                 155                 160
Leu Leu Ala Ala Ala Trp Ile Gln Phe Gln Val His Asp Trp Ala Gln
                165                 170                 175
His Phe Leu Val Thr Asn Gly Asp Lys Asp Ile Asp Ile Pro Leu His
                180                 185                 190
Asn Lys Asp Lys Trp Thr Glu Gln Ser Met Lys Ile Pro Arg Thr Lys
                195                 200                 205
Lys Ala Asp Ile Leu Ser Lys Gln Asp Ala Glu Thr Pro Ala Tyr Asp
                210                 215                 220
Asn Glu Asn Thr His Trp Trp Asp Ala Ser Gln Ile Tyr Gly Ser Ser
225                 230                 235                 240
Glu Ala Glu Thr Gln Ala Leu Arg Ala Lys Cys His Lys Ser Lys Pro
                245                 250                 255
Gly Gln Leu Glu Leu His Leu Ser Asn Pro Ser Trp Ser Ser Asp His
                260                 265                 270
Ile Phe Asp Thr Ala Arg Leu Ile Asn Cys Ala Leu Met Ala Lys Ile
                275                 280                 285
His Thr Val Glu Trp Thr Pro Gly Ile Leu Gln His Pro Ala Leu Gln
                290                 295                 300
Ile Gly Met Asn Ala Asn Trp Trp Gly Leu Leu Gly Asp Lys Leu Trp
305                 310                 315                 320
His Ala Phe Gly Arg Val Phe Asp Asn Lys Ser Glu Val Ile Ser Gly
                325                 330                 335
Ile Pro Gly Ser Gly Val Asp His Asp Lys Ala Pro Tyr Cys Leu Thr
                340                 345                 350
Glu Glu Phe Val Ser Val Tyr Arg Leu His Ser Leu Ile Pro Asp Asn
                355                 360                 365
Val Ala Phe Phe Asn Ile Lys Asp Gly Gln His Glu Gly Thr Leu Pro
                370                 375                 380
Ile Val Asp Val Ser Phe Glu Ser Ala Arg Lys Pro Phe Asp Glu Gly
385                 390                 395                 400
Lys Ser Gly Leu Gly Leu Ser Phe Ala Asp Val Phe Tyr Ser Phe Gly
                405                 410                 415
Val Asn Tyr Pro Gly Ala Ile Arg Ala His Asn Met Pro Asn Phe Leu
                420                 425                 430
```

```
Arg Asp Leu Lys Ile Pro Ala Asp Lys Asp Phe Pro Glu Gly Arg His
            435                 440                 445

Leu Asp Leu Gly Thr Ile Asp Ile Leu Arg Asp Arg Glu Arg Gly Val
        450                 455                 460

Pro Arg Tyr Asn Ala Phe Arg Arg Leu Phe His Met Pro Ala Ala Lys
465                 470                 475                 480

Ser Phe Ile Asp Leu Thr Gly Gly Asp Lys Leu Ala Ser Glu Leu
            485                 490                 495

Glu Glu Val Tyr Glu Gly Asp Leu Glu Ala Val Asp Leu Leu Val Gly
                500                 505                 510

Thr Leu Cys Glu Pro Leu Pro Lys Gly Phe Gly Phe Ser Asp Thr Ala
            515                 520                 525

Phe Arg Val Phe Ile Leu Met Ala Thr Arg Arg Ile Lys Ser Asp Arg
        530                 535                 540

Phe Ile Ala Gly Asp Gly Trp Cys Pro Glu Val Tyr Thr Arg Glu Gly
545                 550                 555                 560

Met Asp Trp Val Gln Lys Asn Thr Met Lys Asp Val Leu Cys Arg His
            565                 570                 575

Phe Pro Glu Leu Ala Ala Pro Leu His Asn Val Lys Asn Ala Phe Ala
        580                 585                 590

Pro Trp Thr Lys Leu Gly Gln Thr Ala Ala Tyr Ala Gly Pro Glu Thr
            595                 600                 605

Asn Lys Ala Lys Ser
            610

<210> SEQ ID NO 4
<211> LENGTH: 653
<212> TYPE: PRT
<213> ORGANISM: Fusarium verticillioides

<400> SEQUENCE: 4

Met Ala Ser Val Leu Ser Lys Glu Ser Leu Ala Ile Ile Leu Ser Val
1               5                   10                  15

Val Thr Leu Leu Ile Gly Leu Ser His Phe Asn Met Ile Ser Leu Lys
            20                  25                  30

Ser Ile Phe Lys Ser Val Tyr Ile Arg Leu Trp Lys Leu Val Asn Val
        35                  40                  45

Phe Val His Trp His Lys Leu Pro Thr Trp Leu Gly Val Phe Asn Leu
    50                  55                  60

Leu Ala Leu Arg Tyr Glu Leu Arg Glu Lys Asn Leu His Asp Thr Tyr
65              70                  75                  80

Pro Asn Ala Glu Phe Gln Gly Thr Ala Ala Asp Cys Pro Met Lys Asn
            85                  90                  95

Ser Lys Phe Ile Ala Thr Arg Asn Ser Asp Gly Asp Phe Asn Asp Leu
        100                 105                 110

Ala Gln Pro Lys Met Gly Cys Ala Gly Met Arg Phe Gly Arg Asn Val
    115                 120                 125

Pro Arg Asn His Thr Thr Pro Pro Thr Gln Gln Glu Leu Leu Thr Pro
130                 135                 140

Asn Pro Arg Leu Ile Ser Glu Lys Ile Leu Ala Arg Pro Glu Gly Gln
145                 150                 155                 160

Phe Lys Pro Ala Glu Ile Val Asn Leu Leu Ala Ala Ala Trp Ile Gln
            165                 170                 175

Phe Gln Val His Asp Trp Ala Gln His Ser Leu Val Thr Asn Gly Asp
```

```
            180                 185                 190
Lys Asp Val Glu Ile Leu Leu Asp Lys Ala Asp Arg Trp Ser Glu Arg
            195                 200                 205
Ile Met Lys Ile Pro Arg Thr Lys Lys Asp Asp Pro Leu Ser Gln Gln
            210                 215                 220
Asp Ile Glu Thr Pro Ala Tyr Thr Asn Glu Cys Thr His Trp Trp Asp
225                 230                 235                 240
Ala Ser Gln Ile Tyr Gly Ser Thr Glu Ala Glu Thr Lys Ala Leu Arg
                245                 250                 255
Ala Gln Cys Asp Lys Ser Tyr Pro Gly Gln Leu His Val Thr Arg Glu
                260                 265                 270
Asp Gly Val Gln Phe Leu Pro Arg Ser Asp Asp Gly Ile Pro Lys Thr
            275                 280                 285
Gly Phe Arg Gln Asn Trp Trp Leu Gly Leu Glu Leu Leu His Thr Leu
            290                 295                 300
Phe Ala Leu Glu His Asn Ala Ile Ala Thr Gln Leu His Leu Ser Asn
305                 310                 315                 320
Pro Ser Trp Ser Ser Asp Gln Ile Phe Asp Thr Ala Arg Leu Ile Asn
                325                 330                 335
Cys Ala Leu Met Ala Lys Ile His Thr Val Glu Trp Thr Pro Gly Ile
                340                 345                 350
Leu Gln His Pro Ala Leu Gln Ile Gly Met Asn Ala Asn Trp Trp Gly
            355                 360                 365
Leu Leu Gly Asp Lys Leu Trp His Val Phe Gly Arg Val Phe Asp Asn
370                 375                 380
Lys Ser Glu Val Ile Ser Gly Ile Pro Gly Ser Gly Val Asp His Asp
385                 390                 395                 400
Asn Val Pro Tyr Cys Leu Thr Glu Glu Phe Val Ser Val Tyr Arg Leu
                405                 410                 415
His Pro Leu Ile Pro Asp Asn Val Ala Phe Phe Ser Ile Lys Asp Gly
                420                 425                 430
Gln His Lys Gly Thr Leu Pro Ile Lys Glu Val Ala Phe Lys Ser Ala
            435                 440                 445
Arg Lys Pro Phe Asp Glu Asp Lys Ser Gly Leu Gly Leu Ser Phe Ala
450                 455                 460
Asp Val Phe Tyr Ser Phe Gly Val Asn Tyr Pro Gly Ala Ile Arg Ala
465                 470                 475                 480
His Asn Met Pro Asn Phe Leu Arg Asp Leu Asn Ile Pro Gly Asp Lys
                485                 490                 495
Asp Phe Pro His Gly Arg His Leu Asp Leu Gly Thr Ile Asp Ile Leu
                500                 505                 510
Arg Asp Arg Glu Arg Gly Val Pro Arg Tyr Asn Ala Phe Arg Arg Leu
            515                 520                 525
Phe His Met Ala Pro Ala Lys Thr Phe Ile Asp Leu Thr Gly Gly Asp
            530                 535                 540
Ser Lys Leu Ala Ala Glu Leu Glu Glu Val Tyr Asp Gly Asp Leu Glu
545                 550                 555                 560
Ala Val Asp Leu Leu Val Gly Thr Leu Ser Glu Pro Leu Pro Lys Gly
                565                 570                 575
Phe Gly Phe Ser Asp Thr Ala Phe Arg Val Phe Ile Leu Met Ala Thr
                580                 585                 590
Arg Arg Ile Lys Ser Asp Arg Phe Leu Ala Gly Asp Gly Trp Cys Pro
            595                 600                 605
```

Glu Val Tyr Thr Arg Glu Gly Ile Asn Trp Val Gln Asn Asn Thr Met
        610                 615                 620

Lys Asp Val Leu Cys Arg His Phe Pro Glu Leu Ala Ala Thr Leu His
625                 630                 635                 640

Asn Val Lys Asn Leu Ser Val Ser Phe Ile Leu Ser Leu
                645                 650

<210> SEQ ID NO 5
<211> LENGTH: 668
<212> TYPE: PRT
<213> ORGANISM: Fusarium oxysporum

<400> SEQUENCE: 5

Met Ala Ser Val Leu Ser Lys Glu Ser Leu Ala Ile Ser Leu Ser Ile
1               5                   10                  15

Val Thr Leu Leu Ile Gly Leu Ser His Phe Asn Met Ile Ser Leu Lys
            20                  25                  30

Pro Ile Phe Lys Ser Val Tyr Ile Arg Leu Trp Lys Phe Val Asn Ile
        35                  40                  45

Phe Val His Trp His Lys Leu Pro Thr Trp Leu Gly Val Phe Asn Leu
    50                  55                  60

Leu Ala Leu Arg Tyr Glu Leu Arg Glu Lys Asn Leu His Asp Thr Tyr
65                  70                  75                  80

Pro Asn Ala Glu Phe Gln Gly Thr Thr Ala Asp Cys Pro Met Lys Asn
                85                  90                  95

Ser Lys Phe Ile Ala Asn Arg Asn Ser Asp Gly Asp Phe Asn Asp Leu
            100                 105                 110

Ala Gln Pro Lys Met Gly Cys Ala Gly Met Arg Phe Gly Arg Asn Val
        115                 120                 125

Pro Arg Lys Tyr Thr Thr Pro Pro Thr Gln Gln Glu Leu Leu Thr Pro
    130                 135                 140

Asn Pro Arg Ile Ile Ser Glu Lys Ile Leu Ala Arg Pro Glu Gly Gln
145                 150                 155                 160

Phe Lys Pro Ala Glu Ile Val Asn Leu Leu Ala Ala Ala Trp Ile Gln
                165                 170                 175

Phe Gln Val His Asp Trp Ala Gln His Phe Leu Val Thr Asn Gly Asp
            180                 185                 190

Lys Asp Val Glu Ile Pro Leu Asp Lys Ala Asp Arg Trp Ser Glu Arg
        195                 200                 205

Ile Met Lys Ile Pro Arg Thr Lys Lys Asp Asp Ala Leu Ser Gln Gln
    210                 215                 220

Asp Ile Glu Thr Pro Ala Tyr Thr Asn Glu Cys Thr His Trp Trp Asp
225                 230                 235                 240

Ala Ser Gln Ile Tyr Gly Ser Thr Glu Ala Glu Thr Lys Ala Leu Arg
                245                 250                 255

Ala Gln Cys Asp Lys Ser Tyr Pro Gly Gln Leu His Val Thr Arg Glu
            260                 265                 270

Asp Gly Val Gln Phe Leu Pro Arg Ser Asp Asp Gly Ile Pro Lys Thr
        275                 280                 285

Gly Phe Arg Gln Asn Trp Trp Leu Gly Leu Glu Leu His Thr Leu
    290                 295                 300

Phe Ala Leu Glu His Asn Ala Ile Ala Thr Gln Leu His Leu Ser Asn
305                 310                 315                 320

Pro Ser Trp Ser Ser Asp Gln Ile Phe Asp Thr Ala Arg Leu Ile Asn

-continued

```
                325                 330                 335
Cys Ala Leu Met Ala Lys Ile His Thr Val Glu Trp Thr Pro Gly Ile
            340                 345                 350
Leu Gln His Pro Ala Leu Gln Ile Gly Met Asn Ala Asn Trp Trp Gly
        355                 360                 365
Leu Leu Gly Asp Lys Leu Trp His Val Phe Gly Arg Val Phe Asp Asn
    370                 375                 380
Lys Ser Glu Val Ile Ser Gly Ile Pro Gly Ser Gly Val Asp His Asp
385                 390                 395                 400
Asn Val Pro Tyr Cys Leu Thr Glu Glu Phe Val Ser Val Tyr Arg Leu
                405                 410                 415
His Pro Leu Ile Pro Asp Asn Val Ala Phe Phe Ser Ile Lys Asp Gly
            420                 425                 430
Gln His Lys Gly Thr Leu Pro Ile Lys Asp Val Ala Phe Glu Ser Ala
        435                 440                 445
Arg Lys Pro Phe Asp Glu Asp Lys Ser Gly Leu Gly Leu Ser Phe Ala
    450                 455                 460
Asp Val Phe Tyr Ser Phe Gly Val Asn Tyr Pro Gly Ala Ile Arg Ala
465                 470                 475                 480
His Asn Met Pro Asn Phe Leu Arg Asp Leu Asn Ile Pro Gly Asp Lys
                485                 490                 495
Asp Phe Pro Gln Gly Arg His Leu Asp Leu Gly Thr Ile Asp Ile Leu
            500                 505                 510
Arg Asp Arg Glu Arg Gly Val Pro Arg Tyr Asn Ala Phe Arg Arg Leu
        515                 520                 525
Phe His Met Ala Pro Ala Lys Ser Phe Leu Asp Leu Thr Gly Gly Asp
    530                 535                 540
Ala Lys Leu Ala Ala Glu Leu Glu Asp Val Tyr Asp Gly Asp Leu Glu
545                 550                 555                 560
Ala Val Asp Leu Leu Val Gly Thr Leu Ser Glu Pro Leu Pro Lys Gly
                565                 570                 575
Phe Gly Phe Ser Asp Thr Ala Phe Arg Val Phe Ile Leu Met Ala Thr
            580                 585                 590
Arg Arg Ile Lys Ser Asp Arg Phe Leu Ala Gly Asp Gly Trp Cys Pro
        595                 600                 605
Glu Val Tyr Thr Arg Glu Gly Ile Asn Trp Val Gln Asn Asn Thr Met
    610                 615                 620
Lys Asp Val Leu Cys Arg His Phe Pro Glu Leu Ala Ala Thr Leu His
625                 630                 635                 640
Asn Val Lys Asn Ala Phe Ala Pro Trp Thr Lys Ile Gly Gln Thr Glu
                645                 650                 655
Ala Tyr Ala Gly Pro Glu Thr Asn Lys Ala Lys Asn
            660                 665

<210> SEQ ID NO 6
<211> LENGTH: 618
<212> TYPE: PRT
<213> ORGANISM: Oryza sative

<400> SEQUENCE: 6

Met Gly Ser Gly Leu Phe Lys Pro Arg Val His Pro Asp Leu Arg Asp
1               5                   10                  15
Val Phe Ser Lys Met Ser Phe Phe Asp Lys Ile Gly Phe Leu Phe Ile
            20                  25                  30
```

-continued

```
His Ala Phe Asp Lys Arg Asn Leu Trp His Lys Val Pro Val Pro Ile
         35                  40                  45

Gly Leu Leu Tyr Leu Asn Thr Arg Arg Thr Leu Leu Glu Lys Tyr Asn
 50                  55                  60

Leu Leu Ala Val Gly Arg Ser Ser His Gly Ala Leu Phe Asp Pro Lys
 65                  70                  75                  80

Glu Phe Leu Tyr Arg Thr Glu Asp Gly Lys Tyr Asn Asp Pro His Asn
                 85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350

Leu Gly Gly Leu Val Gly Leu Lys Lys Pro Asn Asn His Gly Val Pro
        355                 360                 365

Tyr Ser Leu Thr Glu Glu Phe Thr Ser Val Tyr Arg Met His Ser Leu
    370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
            420                 425                 430

Ala Leu Ser Met Gly Tyr Gln Ala Cys Gly Ala Leu Glu Leu Trp Asn
        435                 440                 445

Tyr Pro Ser Phe Phe Arg Asn Leu Ile Pro Gln Asn Leu Asp Gly Thr
```

```
            450                 455                 460
Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Leu Phe
                485                 490                 495

Leu Ile Pro Ile Lys Ser Trp Glu Asp Leu Thr Ser Asp Lys Asp Ala
                500                 505                 510

Ile Glu Thr Ile Arg Ala Ile Tyr Gly Asp Asp Val Glu Lys Leu Asp
                515                 520                 525

Leu Leu Val Gly Leu Met Ala Glu Lys Lys Ile Lys Gly Phe Ala Ile
                530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Gly Thr Tyr Thr
                565                 570                 575

Lys Lys Gly Met Gln Trp Val Lys Thr Thr Glu Gly Leu Arg Asp Val
                580                 585                 590

Ile Asn Arg His Tyr Pro Glu Ile Thr Ala Lys Trp Met Lys Ser Ser
                595                 600                 605

Ser Ala Phe Ser Val Trp Asp Ala Asp Tyr
                610                 615

<210> SEQ ID NO 7
<211> LENGTH: 674
<212> TYPE: PRT
<213> ORGANISM: Homo sapiens

<400> SEQUENCE: 7

Met Pro Ser Tyr Thr Val Thr Val Ala Thr Gly Ser Gln Trp Phe Ala
1               5                   10                  15

Gly Thr Asp Asp Tyr Ile Tyr Leu Ser Leu Val Gly Ser Ala Gly Cys
                20                  25                  30

Ser Glu Lys His Leu Leu Asp Lys Pro Phe Tyr Asn Asp Phe Glu Arg
                35                  40                  45

Gly Ala Val Asp Ser Tyr Asp Val Thr Val Asp Glu Glu Leu Gly Glu
                50                  55                  60

Ile Gln Leu Val Arg Ile Glu Lys Arg Lys Tyr Trp Leu Asn Asp Asp
65                  70                  75                  80

Trp Tyr Leu Lys Tyr Ile Thr Leu Lys Thr Pro His Gly Asp Tyr Ile
                85                  90                  95

Glu Phe Pro Cys Tyr Arg Trp Ile Thr Gly Asp Val Glu Val Val Leu
                100                 105                 110

Arg Asp Gly Arg Ala Lys Leu Ala Arg Asp Asp Gln Ile His Ile Leu
                115                 120                 125

Lys Gln His Arg Arg Lys Glu Leu Glu Thr Arg Gln Lys Gln Tyr Arg
                130                 135                 140

Trp Met Glu Trp Asn Pro Gly Phe Pro Leu Ser Ile Asp Ala Lys Cys
145                 150                 155                 160

His Lys Asp Leu Pro Arg Asp Ile Gln Phe Asp Ser Glu Lys Gly Val
                165                 170                 175

Asp Phe Val Leu Asn Tyr Ser Lys Ala Met Glu Asn Leu Phe Ile Asn
                180                 185                 190

Arg Phe Met His Met Phe Gln Ser Ser Trp Asn Asp Phe Ala Asp Phe
                195                 200                 205
```

```
Glu Lys Ile Phe Val Lys Ile Ser Asn Thr Ile Ser Glu Arg Val Met
    210             215                 220

Asn His Trp Gln Glu Asp Leu Met Phe Gly Tyr Gln Phe Leu Asn Gly
225             230                 235                 240

Cys Asn Pro Val Leu Ile Arg Arg Cys Thr Glu Leu Pro Glu Lys Leu
                245                 250                 255

Pro Val Thr Thr Glu Met Val Glu Cys Ser Leu Glu Arg Gln Leu Ser
            260                 265                 270

Leu Glu Gln Glu Val Gln Gln Gly Asn Ile Phe Ile Val Asp Phe Glu
            275                 280                 285

Leu Leu Asp Gly Ile Asp Ala Asn Lys Thr Asp Pro Cys Thr Leu Gln
        290                 295                 300

Phe Leu Ala Ala Pro Ile Cys Leu Leu Tyr Lys Asn Leu Ala Asn Lys
305                 310                 315                 320

Ile Val Pro Ile Ala Ile Gln Leu Asn Gln Ile Pro Gly Asp Glu Asn
                325                 330                 335

Pro Ile Phe Leu Pro Ser Asp Ala Lys Tyr Asp Trp Leu Leu Ala Lys
            340                 345                 350

Ile Trp Val Arg Ser Ser Asp Phe His Val His Gln Thr Ile Thr His
        355                 360                 365

Leu Leu Arg Thr His Leu Val Ser Glu Val Phe Gly Ile Ala Met Tyr
    370                 375                 380

Arg Gln Leu Pro Ala Val His Pro Ile Phe Lys Leu Leu Val Ala His
385                 390                 395                 400

Val Arg Phe Thr Ile Ala Ile Asn Thr Lys Ala Arg Glu Gln Leu Ile
                405                 410                 415

Cys Glu Cys Gly Leu Phe Asp Lys Ala Asn Ala Thr Gly Gly Gly Gly
            420                 425                 430

His Val Gln Met Val Gln Arg Ala Met Lys Asp Leu Thr Tyr Ala Ser
        435                 440                 445

Leu Cys Phe Pro Glu Ala Ile Lys Ala Arg Gly Met Glu Ser Lys Glu
    450                 455                 460

Asp Ile Pro Tyr Tyr Phe Tyr Arg Asp Asp Gly Leu Leu Val Trp Glu
465                 470                 475                 480

Ala Ile Arg Thr Phe Thr Ala Glu Val Val Asp Ile Tyr Tyr Glu Gly
                485                 490                 495

Asp Gln Val Val Glu Glu Asp Pro Glu Leu Gln Asp Phe Val Asn Asp
            500                 505                 510

Val Tyr Val Tyr Gly Met Arg Gly Arg Lys Ser Ser Gly Phe Pro Lys
        515                 520                 525

Ser Val Lys Ser Arg Glu Gln Leu Ser Glu Tyr Leu Thr Val Val Ile
    530                 535                 540

Phe Thr Ala Ser Ala Gln His Ala Ala Val Asn Phe Gly Gln Tyr Asp
545                 550                 555                 560

Trp Cys Ser Trp Ile Pro Asn Ala Pro Pro Thr Met Arg Ala Pro Pro
                565                 570                 575

Pro Thr Ala Lys Gly Val Val Thr Ile Glu Gln Ile Val Asp Thr Leu
            580                 585                 590

Pro Asp Arg Gly Arg Ser Cys Trp His Leu Gly Ala Val Trp Ala Leu
        595                 600                 605

Ser Gln Phe Gln Glu Asn Glu Leu Phe Leu Gly Met Tyr Pro Glu Glu
    610                 615                 620

His Phe Ile Glu Lys Pro Val Lys Glu Ala Met Ala Arg Phe Arg Lys
```

```
            625                 630                 635                 640

Asn Leu Glu Ala Ile Val Ser Val Ile Ala Glu Arg Asn Lys Lys Lys
                    645                 650                 655

Gln Leu Pro Tyr Tyr Tyr Leu Ser Pro Asp Arg Ile Pro Asn Ser Val
                    660                 665                 670

Ala Ile

<210> SEQ ID NO 8
<211> LENGTH: 1066
<212> TYPE: PRT
<213> ORGANISM: Plexaura homomalla

<400> SEQUENCE: 8

Met Thr Trp Lys Asn Phe Gly Phe Glu Ile Phe Gly Glu Lys Tyr Gly
1               5                   10                  15

Gln Glu Glu Leu Glu Lys Arg Ile Lys Asp Glu His Thr Pro Pro Pro
                20                  25                  30

Asp Ser Pro Val Phe Gly Gly Leu Lys Leu Lys Leu Lys Lys Glu Lys
            35                  40                  45

Phe Lys Thr Leu Phe Thr Leu Gly Thr Thr Leu Lys Gly Phe Arg Arg
        50                  55                  60

Ala Thr His Thr Val Gly Thr Gly Gly Ile Gly Glu Ile Thr Ile Val
65                  70                  75                  80

Asn Asp Pro Lys Phe Pro Glu His Glu Phe Thr Ala Gly Arg Thr
                    85                  90                  95

Phe Pro Ala Arg Leu Arg His Ala Asn Leu Lys Tyr Pro Asp Asp Ala
                100                 105                 110

Gly Ala Asp Ala Arg Ser Phe Ser Ile Lys Phe Ala Asp Ser Asp Ser
            115                 120                 125

Asp Gly Pro Leu Asp Ile Val Met Asn Thr Gly Glu Ala Asn Ile Phe
        130                 135                 140

Trp Asn Ser Pro Ser Leu Glu Asp Phe Val Pro Val Glu Glu Gly Asp
145                 150                 155                 160

Ala Ala Glu Glu Tyr Val Tyr Lys Asn Pro Tyr Tyr Tyr Asn Leu
                165                 170                 175

Val Glu Ala Leu Arg Arg Ala Pro Asp Thr Phe Ala His Leu Tyr Tyr
            180                 185                 190

Tyr Ser Gln Val Thr Met Pro Phe Lys Ala Lys Asp Gly Lys Val Arg
        195                 200                 205

Tyr Cys Arg Tyr Arg Ala Leu Pro Gly Asp Val Asp Ile Lys Glu Glu
210                 215                 220

Asp Glu Ser Gly Arg Leu Thr Glu Glu Glu Gln Arg Lys Ile Trp Ile
225                 230                 235                 240

Phe Ser Arg His Glu Asn Glu Lys Arg Pro Asp Asp Tyr Leu Arg Lys
                245                 250                 255

Glu Tyr Val Glu Arg Leu Gln Lys Gly Pro Val Asn Tyr Arg Leu Gln
            260                 265                 270

Ile Gln Ile His Glu Ala Ser Pro Asp Asp Thr Ala Thr Ile Phe His
        275                 280                 285

Ala Gly Ile Leu Trp Asp Lys Glu Thr His Pro Trp Phe Asp Leu Ala
        290                 295                 300

Lys Val Ser Ile Lys Thr Pro Leu Ser Pro Asp Val Leu Glu Lys Thr
305                 310                 315                 320

Ala Phe Asn Ile Ala Asn Gln Pro Ala Ser Leu Gly Leu Leu Glu Ala
```

-continued

```
                325                 330                 335
Lys Ser Pro Glu Asp Tyr Asn Ser Ile Gly Glu Leu Arg Val Ala Val
            340                 345                 350
Tyr Thr Trp Val Gln His Leu Arg Lys Leu Lys Ile Gly Ser Leu Val
            355                 360                 365
Pro Ala Gly Gln Asn Ala Ile Tyr Asn Val Glu Val Glu Thr Gly Asp
            370                 375                 380
Arg Glu His Ala Gly Thr Asp Ala Thr Ile Thr Ile Arg Ile Thr Gly
385                 390                 395                 400
Ala Lys Gly Arg Thr Asp Tyr Leu Lys Leu Asp Lys Trp Phe His Asn
            405                 410                 415
Asp Phe Glu Ala Gly Ser Lys Glu Gln Tyr Thr Val Gln Gly Phe Asp
            420                 425                 430
Val Gly Asp Ile Gln Leu Ile Glu Leu His Ser Asp Gly Gly Tyr
            435                 440                 445
Trp Ser Gly Asp Pro Asp Trp Phe Val Asn Arg Val Ile Ile Ser
            450                 455                 460
Ser Thr Gln Asp Arg Val Tyr Ser Phe Pro Cys Phe Arg Trp Val Ile
465                 470                 475                 480
Lys Asp Met Val Leu Phe Pro Gly Glu Ala Thr Leu Pro Phe Asn Glu
            485                 490                 495
Val Pro Ala Ile Val Ser Glu Gln Arg Gln Lys Glu Leu Glu Gln Arg
            500                 505                 510
Lys Leu Thr Tyr Gln Trp Asp Tyr Val Ser Asp Met Pro Gly Asn
            515                 520                 525
Ile Lys Ala Lys Thr His Asp Asp Leu Pro Arg Asp Val Gln Phe Thr
            530                 535                 540
Asp Glu Lys Ser Arg Ser Tyr Gln Glu Ser Arg Lys Ala Ala Leu Val
545                 550                 555                 560
Asn Leu Gly Ile Gly Ser Leu Phe Thr Met Phe Glu Asn Trp Asp Ser
            565                 570                 575
Tyr Asp Asp Tyr His Ile Leu Tyr Arg Asn Trp Ile Leu Gly Gly Thr
            580                 585                 590
Pro Asn Met Ala Asp Arg Trp His Glu Asp Arg Trp Phe Gly Tyr Gln
            595                 600                 605
Phe Leu Asn Gly Ala Asn Pro Val Ile Leu Thr Arg Cys Asp Ala Leu
            610                 615                 620
Pro Ser Asn Phe Pro Val Thr Asn Glu His Val Asn Ala Ser Leu Asp
625                 630                 635                 640
Arg Gly Lys Asn Leu Asp Glu Glu Ile Lys Asp Gly His Ile Tyr Ile
            645                 650                 655
Val Asp Phe Lys Val Leu Val Gly Ala Lys Ser Tyr Gly Gly Pro Val
            660                 665                 670
Leu Glu Asp Ile Gly Tyr Lys Val Pro Asp His Leu Lys His Asp Glu
            675                 680                 685
Ala Asp Ile Arg Tyr Cys Ala Ala Pro Leu Ala Leu Phe Tyr Val Asn
            690                 695                 700
Lys Leu Gly His Leu Met Pro Ile Ala Ile Gln Ile Asn Gln Glu Pro
705                 710                 715                 720
Gly Pro Glu Asn Pro Ile Trp Thr Pro His Glu Glu Asn Glu His Asp
            725                 730                 735
Trp Met Met Ala Lys Phe Trp Leu Gly Val Ala Glu Ser Asn Phe His
            740                 745                 750
```

Gln Leu Asn Thr His Leu Leu Arg Thr His Leu Thr Glu Ser Phe
        755                 760                 765

Ala Leu Ser Thr Trp Arg Asn Leu Ala Ser Ala His Pro Val Phe Lys
770                 775                 780

Leu Leu Gln Pro His Ile Tyr Gly Val Leu Ala Ile Asp Thr Ile Gly
785                 790                 795                 800

Arg Lys Glu Leu Ile Gly Ser Gly Gly Ile Val Asp Gln Ser Leu Ser
                805                 810                 815

Leu Gly Gly Gly Gly His Val Thr Phe Met Glu Lys Cys Phe Lys Glu
                820                 825                 830

Val Asn Leu Gln Asp Tyr His Leu Pro Asn Ala Leu Lys Lys Arg Gly
                835                 840                 845

Val Asp Asp Pro Ser Lys Leu Pro Gly Phe Tyr Tyr Arg Asp Asp Gly
850                 855                 860

Leu Ala Leu Trp Glu Ala Ile Glu Thr Phe Ile Gly Glu Ile Ile Ala
865                 870                 875                 880

Ile Phe Tyr Lys Asn Asp Asp Val Lys Arg Asp Asn Glu Ile Gln
                885                 890                 895

Ser Trp Ile Tyr Asp Val His Lys Asn Gly Trp Arg Val Asn Pro Gly
                900                 905                 910

His Gln Asp His Gly Val Pro Ala Ser Phe Glu Ser Arg Glu Gln Leu
                915                 920                 925

Lys Glu Val Leu Thr Ser Leu Val Phe Thr Phe Ser Cys Gln His Ala
930                 935                 940

Ala Val Asn Phe Ser Gln Lys Asp His Tyr Gly Phe Thr Pro Asn Ala
945                 950                 955                 960

Pro Ala Val Leu Arg His Pro Pro Lys Lys Lys Gly Glu Ala Thr
                965                 970                 975

Leu Gln Ser Ile Leu Ser Thr Leu Pro Ser Lys Ser Gln Ala Ala Lys
                980                 985                 990

Ala Ile Ala Thr Val Tyr Ile Leu Thr Lys Phe Ser Glu Asp Glu Arg
                995                 1000                1005

Tyr Leu Gly Asn Tyr Ser Ala Thr Ala Trp Glu Asp Lys Asp Ala
        1010                1015                1020

Leu Asp Ala Ile Asn Arg Phe Gln Asp Lys Leu Glu Asp Ile Ser
        1025                1030                1035

Lys Lys Ile Lys Gln Arg Asn Glu Asn Leu Glu Val Pro Tyr Ile
        1040                1045                1050

Tyr Leu Leu Pro Glu Arg Ile Pro Asn Gly Thr Ala Ile
        1055                1060                1065

<210> SEQ ID NO 9
<211> LENGTH: 663
<212> TYPE: PRT
<213> ORGANISM: Homo sapiens

<400> SEQUENCE: 9

Met Gly Arg Tyr Arg Ile Arg Val Ala Thr Gly Ala Trp Leu Phe Ser
1               5                   10                  15

Gly Ser Tyr Asn Arg Val Gln Leu Trp Leu Val Gly Thr Arg Gly Glu
                20                  25                  30

Ala Glu Leu Glu Leu Gln Leu Arg Pro Ala Arg Gly Glu Glu Glu Glu
            35                  40                  45

Phe Asp His Asp Val Ala Glu Asp Leu Gly Leu Leu Gln Phe Val Arg

```
                50                  55                  60
Leu Arg Lys His His Trp Leu Val Asp Asp Ala Trp Phe Cys Asp Arg
 65                  70                  75                  80

Ile Thr Val Gln Gly Pro Gly Ala Cys Ala Glu Val Ala Phe Pro Cys
                     85                  90                  95

Tyr Arg Trp Val Gln Gly Glu Asp Ile Leu Ser Leu Pro Glu Gly Thr
                    100                 105                 110

Ala Arg Leu Pro Gly Asp Asn Ala Leu Asp Met Phe Gln Lys His Arg
                    115                 120                 125

Glu Lys Glu Leu Lys Asp Arg Gln Gln Ile Tyr Cys Trp Ala Thr Trp
                    130                 135                 140

Lys Glu Gly Leu Pro Leu Thr Ile Ala Ala Asp Arg Lys Asp Asp Leu
145                 150                 155                 160

Pro Pro Asn Met Arg Phe His Glu Glu Lys Arg Leu Asp Phe Glu Trp
                    165                 170                 175

Thr Leu Lys Ala Gly Ala Leu Glu Met Ala Leu Lys Arg Val Tyr Thr
                    180                 185                 190

Leu Leu Ser Ser Trp Asn Cys Leu Glu Asp Phe Asp Gln Ile Phe Trp
                    195                 200                 205

Gly Gln Lys Ser Ala Leu Ala Glu Lys Val Arg Gln Cys Trp Gln Asp
                    210                 215                 220

Asp Glu Leu Phe Ser Tyr Gln Phe Leu Asn Gly Ala Asn Pro Met Leu
225                 230                 235                 240

Leu Arg Arg Ser Thr Ser Leu Pro Ser Arg Leu Val Leu Pro Ser Gly
                    245                 250                 255

Met Glu Glu Leu Gln Ala Gln Leu Glu Lys Glu Leu Gln Asn Gly Ser
                    260                 265                 270

Leu Phe Glu Ala Asp Phe Ile Leu Leu Asp Gly Ile Pro Ala Asn Val
                    275                 280                 285

Ile Arg Gly Glu Lys Gln Tyr Leu Ala Ala Pro Leu Val Met Leu Lys
                    290                 295                 300

Met Glu Pro Asn Gly Lys Leu Gln Pro Met Val Ile Gln Ile Gln Pro
305                 310                 315                 320

Pro Asn Pro Ser Ser Pro Thr Pro Thr Leu Phe Leu Pro Ser Asp Pro
                    325                 330                 335

Pro Leu Ala Trp Leu Leu Ala Lys Ser Trp Val Arg Asn Ser Asp Phe
                    340                 345                 350

Gln Leu His Glu Ile Gln Tyr His Leu Leu Asn Thr His Leu Val Ala
                    355                 360                 365

Glu Val Ile Ala Val Ala Thr Met Arg Cys Leu Pro Gly Leu His Pro
                    370                 375                 380

Ile Phe Lys Phe Leu Ile Pro His Ile Arg Tyr Thr Met Glu Ile Asn
385                 390                 395                 400

Thr Arg Ala Arg Thr Gln Leu Ile Ser Asp Gly Gly Ile Phe Asp Lys
                    405                 410                 415

Ala Val Ser Thr Gly Gly Gly His Val Gln Leu Leu Arg Arg Ala
                    420                 425                 430

Ala Ala Gln Leu Thr Tyr Cys Ser Leu Cys Pro Pro Asp Asp Leu Ala
                    435                 440                 445

Asp Arg Gly Leu Leu Gly Leu Pro Gly Ala Leu Tyr Ala His Asp Ala
                    450                 455                 460

Leu Arg Leu Trp Glu Ile Ile Ala Arg Tyr Val Glu Gly Ile Val His
465                 470                 475                 480
```

```
Leu Phe Tyr Gln Arg Asp Asp Ile Val Lys Gly Asp Pro Glu Leu Gln
                485                 490                 495

Ala Trp Cys Arg Glu Ile Thr Glu Val Gly Leu Cys Gln Ala Gln Asp
            500                 505                 510

Arg Gly Phe Pro Val Ser Phe Gln Ser Gln Ser Gln Leu Cys His Phe
        515                 520                 525

Leu Thr Met Cys Val Phe Thr Cys Thr Ala Gln His Ala Ala Ile Asn
    530                 535                 540

Gln Gly Gln Leu Asp Trp Tyr Ala Trp Val Pro Asn Ala Pro Cys Thr
545                 550                 555                 560

Met Arg Met Pro Pro Thr Thr Lys Glu Asp Val Thr Met Ala Thr
                565                 570                 575

Val Met Gly Ser Leu Pro Asp Val Arg Gln Ala Cys Leu Gln Met Ala
                580                 585                 590

Ile Ser Trp His Leu Ser Arg Arg Gln Pro Asp Met Val Pro Leu Gly
            595                 600                 605

His His Lys Glu Lys Tyr Phe Ser Gly Pro Lys Pro Lys Ala Val Leu
        610                 615                 620

Asn Gln Phe Arg Thr Asp Leu Glu Lys Leu Lys Glu Ile Thr Ala
625                 630                 635                 640

Arg Asn Glu Gln Leu Asp Trp Pro Tyr Glu Tyr Leu Lys Pro Ser Cys
                645                 650                 655

Ile Glu Asn Ser Val Thr Ile
                660

<210> SEQ ID NO 10
<211> LENGTH: 701
<212> TYPE: PRT
<213> ORGANISM: Homo sapiens

<400> SEQUENCE: 10

Met Ala Thr Tyr Lys Val Arg Val Ala Thr Gly Thr Asp Leu Leu Ser
1               5                   10                  15

Gly Thr Arg Asp Ser Ile Ser Leu Thr Ile Val Gly Thr Gln Gly Glu
            20                  25                  30

Ser His Lys Gln Leu Leu Asn His Phe Gly Arg Asp Phe Ala Thr Gly
        35                  40                  45

Ala Val Gly Gln Tyr Thr Val Gln Cys Pro Gln Asp Leu Gly Glu Leu
    50                  55                  60

Ile Ile Ile Arg Leu His Lys Glu Arg Tyr Ala Phe Phe Pro Lys Asp
65                  70                  75                  80

Pro Trp Tyr Cys Asn Tyr Val Gln Ile Cys Ala Pro Asn Gly Arg Ile
                85                  90                  95

Tyr His Phe Pro Ala Tyr Gln Trp Met Asp Gly Tyr Glu Thr Leu Ala
                100                 105                 110

Leu Arg Glu Ala Thr Gly Lys Thr Thr Ala Asp Asp Ser Leu Pro Val
            115                 120                 125

Leu Leu Glu His Arg Lys Glu Glu Ile Arg Ala Lys Gln Asp Phe Tyr
        130                 135                 140

His Trp Arg Val Phe Leu Pro Gly Leu Pro Ser Tyr Val His Ile Pro
145                 150                 155                 160

Ser Tyr Arg Pro Pro Val Arg Arg His Arg Asn Pro Asn Arg Pro Glu
                165                 170                 175

Trp Asn Gly Tyr Ile Pro Gly Phe Pro Ile Leu Ile Asn Phe Lys Ala
```

```
            180                 185                 190
Thr Lys Phe Leu Asn Leu Asn Leu Arg Tyr Ser Phe Leu Lys Thr Ala
            195                 200                 205
Ser Phe Phe Val Arg Leu Gly Pro Met Ala Leu Ala Phe Lys Val Arg
            210                 215                 220
Gly Leu Leu Asp Cys Lys His Ser Trp Lys Arg Leu Lys Asp Ile Arg
225                 230                 235                 240
Lys Ile Phe Pro Gly Lys Lys Ser Val Val Ser Glu Tyr Val Ala Glu
                245                 250                 255
His Trp Ala Glu Asp Thr Phe Phe Gly Tyr Gln Tyr Leu Asn Gly Val
                260                 265                 270
Asn Pro Gly Leu Ile Arg Arg Cys Thr Arg Ile Pro Asp Lys Phe Pro
            275                 280                 285
Val Thr Asp Asp Met Val Ala Pro Phe Leu Gly Glu Gly Thr Cys Leu
            290                 295                 300
Gln Ala Glu Leu Glu Lys Gly Asn Ile Tyr Leu Ala Asp Tyr Arg Ile
305                 310                 315                 320
Met Glu Gly Ile Pro Thr Val Glu Leu Ser Gly Arg Lys Gln His His
                325                 330                 335
Cys Ala Pro Leu Cys Leu Leu His Phe Gly Pro Glu Gly Lys Met Met
                340                 345                 350
Pro Ile Ala Ile Gln Leu Ser Gln Thr Pro Gly Pro Asp Cys Pro Ile
            355                 360                 365
Phe Leu Pro Ser Asp Ser Glu Trp Asp Trp Leu Leu Ala Lys Thr Trp
            370                 375                 380
Val Arg Tyr Ala Glu Phe Tyr Ser His Glu Ala Ile Ala His Leu Leu
385                 390                 395                 400
Glu Thr His Leu Ile Ala Glu Ala Phe Cys Leu Ala Leu Leu Arg Asn
                405                 410                 415
Leu Pro Met Cys His Pro Leu Tyr Lys Leu Leu Ile Pro His Thr Arg
                420                 425                 430
Tyr Thr Val Gln Ile Asn Ser Ile Gly Arg Ala Val Leu Leu Asn Glu
            435                 440                 445
Gly Gly Leu Ser Ala Lys Gly Met Ser Leu Gly Val Glu Gly Phe Ala
            450                 455                 460
Gly Val Met Val Arg Ala Leu Ser Glu Leu Thr Tyr Asp Ser Leu Tyr
465                 470                 475                 480
Leu Pro Asn Asp Phe Val Glu Arg Gly Val Gln Asp Leu Pro Gly Tyr
                485                 490                 495
Tyr Tyr Arg Asp Asp Ser Leu Ala Val Trp Asn Ala Leu Glu Lys Tyr
                500                 505                 510
Val Thr Glu Ile Ile Thr Tyr Tyr Tyr Pro Ser Asp Ala Ala Val Glu
            515                 520                 525
Gly Asp Pro Glu Leu Gln Ser Trp Val Gln Glu Ile Phe Lys Glu Cys
            530                 535                 540
Leu Leu Gly Arg Glu Ser Ser Gly Phe Pro Arg Cys Leu Arg Thr Val
545                 550                 555                 560
Pro Glu Leu Ile Arg Tyr Val Thr Ile Val Ile Tyr Thr Cys Ser Ala
                565                 570                 575
Lys His Ala Ala Val Asn Thr Gly Gln Met Glu Phe Thr Ala Trp Met
            580                 585                 590
Pro Asn Phe Pro Ala Ser Met Arg Asn Pro Pro Ile Gln Thr Lys Gly
            595                 600                 605
```

```
Leu Thr Thr Leu Glu Thr Phe Met Asp Thr Leu Pro Asp Val Lys Thr
            610                 615                 620

Thr Cys Ile Thr Leu Leu Val Leu Trp Thr Leu Ser Arg Glu Pro Asp
625                 630                 635                 640

Asp Arg Arg Pro Leu Gly His Phe Pro Asp Ile His Phe Val Glu Glu
                645                 650                 655

Ala Pro Arg Arg Ser Ile Glu Ala Phe Arg Gln Arg Leu Asn Gln Ile
            660                 665                 670

Ser His Asp Ile Arg Gln Arg Asn Lys Cys Leu Pro Ile Pro Tyr Tyr
            675                 680                 685

Tyr Leu Asp Pro Val Leu Ile Glu Asn Ser Ile Ser Ile
            690                 695                 700

<210> SEQ ID NO 11
<211> LENGTH: 662
<212> TYPE: PRT
<213> ORGANISM: Homo sapiens

<400> SEQUENCE: 11

Met Gly Leu Tyr Arg Ile Arg Val Ser Thr Gly Ala Ser Leu Tyr Ala
1               5                   10                  15

Gly Ser Asn Asn Gln Val Gln Leu Trp Leu Val Gly Gln His Gly Glu
            20                  25                  30

Ala Ala Leu Gly Lys Arg Leu Trp Pro Ala Arg Gly Lys Glu Thr Glu
        35                  40                  45

Leu Lys Val Glu Val Pro Glu Tyr Leu Gly Pro Leu Leu Phe Val Lys
    50                  55                  60

Leu Arg Lys Arg His Leu Leu Lys Asp Ala Trp Phe Cys Asn Trp
65                  70                  75                  80

Ile Ser Val Gln Gly Pro Gly Ala Gly Asp Glu Val Arg Phe Pro Cys
                85                  90                  95

Tyr Arg Trp Val Glu Gly Asn Gly Val Leu Ser Leu Pro Glu Gly Thr
            100                 105                 110

Gly Arg Thr Val Gly Glu Asp Pro Gln Gly Leu Phe Gln Lys His Arg
        115                 120                 125

Glu Glu Glu Leu Glu Glu Arg Arg Lys Leu Tyr Arg Trp Gly Asn Trp
    130                 135                 140

Lys Asp Gly Leu Ile Leu Asn Met Ala Gly Ala Lys Leu Tyr Asp Leu
145                 150                 155                 160

Pro Val Asp Glu Arg Phe Leu Glu Asp Lys Arg Val Asp Phe Glu Val
                165                 170                 175

Ser Leu Ala Lys Gly Leu Ala Asp Leu Ala Ile Lys Asp Ser Leu Asn
            180                 185                 190

Val Leu Thr Cys Trp Lys Asp Leu Asp Asp Phe Asn Arg Ile Phe Trp
        195                 200                 205

Cys Gly Gln Ser Lys Leu Ala Glu Arg Val Arg Asp Ser Trp Lys Glu
    210                 215                 220

Asp Ala Leu Phe Gly Tyr Gln Phe Leu Asn Gly Ala Asn Pro Val Val
225                 230                 235                 240

Leu Arg Arg Ser Ala His Leu Pro Ala Arg Leu Val Phe Pro Pro Gly
                245                 250                 255

Met Glu Glu Leu Gln Ala Gln Leu Glu Lys Glu Leu Glu Gly Gly Thr
            260                 265                 270

Leu Phe Glu Ala Asp Phe Ser Leu Leu Asp Gly Ile Lys Ala Asn Val
```

```
                    275                 280                 285
Ile Leu Cys Ser Gln Gln His Leu Ala Ala Pro Leu Val Met Leu Lys
290                 295                 300

Leu Gln Pro Asp Gly Lys Leu Leu Pro Met Val Ile Gln Leu Gln Leu
305                 310                 315                 320

Pro Arg Thr Gly Ser Pro Pro Pro Leu Phe Leu Pro Thr Asp Pro
    325                 330                 335

Pro Met Ala Trp Leu Leu Ala Lys Cys Trp Val Arg Ser Ser Asp Phe
            340                 345                 350

Gln Leu His Glu Leu Gln Ser His Leu Leu Arg Gly His Leu Met Ala
                355                 360                 365

Glu Val Ile Val Ala Thr Met Arg Cys Leu Pro Ser Ile His Pro
370                 375                 380

Ile Phe Lys Leu Ile Ile Pro His Leu Arg Tyr Thr Leu Glu Ile Asn
385                 390                 395                 400

Val Arg Ala Arg Thr Gly Leu Val Ser Asp Met Gly Ile Phe Asp Gln
                405                 410                 415

Ile Met Ser Thr Gly Gly Gly His Val Gln Leu Leu Lys Gln Ala
            420                 425                 430

Gly Ala Phe Leu Thr Tyr Ser Ser Phe Cys Pro Pro Asp Leu Ala
                435                 440                 445

Asp Arg Gly Leu Leu Gly Val Lys Ser Ser Phe Tyr Ala Gln Asp Ala
450                 455                 460

Leu Arg Leu Trp Glu Ile Ile Tyr Arg Tyr Val Glu Gly Ile Val Ser
465                 470                 475                 480

Leu His Tyr Lys Thr Asp Val Ala Val Lys Asp Asp Pro Glu Leu Gln
                485                 490                 495

Thr Trp Cys Arg Glu Ile Thr Glu Ile Gly Leu Gln Gly Ala Gln Asp
            500                 505                 510

Arg Gly Phe Pro Val Ser Leu Gln Ala Arg Asp Gln Val Cys His Phe
        515                 520                 525

Val Thr Met Cys Ile Phe Thr Cys Thr Gly Gln His Ala Ser Val His
530                 535                 540

Leu Gly Gln Leu Asp Trp Tyr Ser Trp Val Pro Asn Ala Pro Cys Thr
545                 550                 555                 560

Met Arg Leu Pro Pro Pro Thr Thr Lys Asp Ala Thr Leu Glu Thr Val
                565                 570                 575

Met Ala Thr Leu Pro Asn Phe His Gln Ala Ser Leu Gln Met Ser Ile
            580                 585                 590

Thr Trp Gln Leu Gly Arg Arg Gln Pro Val Met Val Ala Val Gly Gln
        595                 600                 605

His Glu Glu Glu Tyr Phe Ser Gly Pro Glu Pro Lys Ala Val Leu Lys
    610                 615                 620

Lys Phe Arg Glu Glu Leu Ala Ala Leu Asp Lys Glu Ile Glu Ile Arg
625                 630                 635                 640

Asn Ala Lys Leu Asp Met Pro Tyr Glu Tyr Leu Arg Pro Ser Val Val
                645                 650                 655

Glu Asn Ser Val Ala Ile
            660

<210> SEQ ID NO 12
<211> LENGTH: 937
<212> TYPE: PRT
<213> ORGANISM: Physcomitrella patens
```

<400> SEQUENCE: 12

```
Met Met Leu Asn Arg Leu Glu Thr Gly Ser Leu Ala Ser Ala Phe Arg
1               5                   10                  15

Gly Ser Arg Glu Glu Phe Val Val Ser Arg Gly Arg Ser Pro Gly Arg
            20                  25                  30

Ser Gln Ser Ile Gln Val Arg Ala Ser Ser Gly Gly Asp Pro Ala Gly
        35                  40                  45

Trp Leu Gln Thr Ala Ser Lys Gln Leu Gly Lys Leu Ser Ser Phe Gly
    50                  55                  60

Glu Lys Arg Lys Thr Ala Thr Ser Thr Ser Thr Arg Gly Pro Ser Gly
65                  70                  75                  80

Asp Asn Val Gln Tyr Thr Gly Val Ala Thr Thr Met Lys Lys Leu Lys
                85                  90                  95

Val Leu Asp Leu Ile Asp Arg Val Ala Asp Ile Gln Asp Asp Thr Ser
            100                 105                 110

Glu Ile Val Gly Gly Lys Arg Val Thr Val Gln Leu Val Ser Lys Asp
        115                 120                 125

Val Asp Pro Lys Thr Gly Glu Ser Met Lys Ser Ser Glu Val Ile Phe
130                 135                 140

Pro Asn Trp Ala Gly Leu Glu Gly Pro Ala Ala Ser Leu Ile Asp Phe
145                 150                 155                 160

Val Leu Glu Phe Thr Val Pro Lys Ser Phe Gly Val Pro Gly Ala Ile
                165                 170                 175

Leu Val Lys Asn Ala His Pro Asn Glu Phe Leu Leu Val Ser Phe Glu
            180                 185                 190

Leu Glu Leu His Asp Lys Ser Lys Ala His Tyr Val Thr Asn Ser Trp
        195                 200                 205

Val Tyr Asn Thr Glu Lys Thr Gly Ala Arg Ile Phe Phe Gln Asn Thr
    210                 215                 220

Ala Tyr Leu Pro Asp Glu Thr Pro Ala Ser Leu Lys Ala Leu Arg Glu
225                 230                 235                 240

Gln Glu Leu Ile Asn Leu Arg Gly Asp Gly Thr Gly Glu Arg Gln Ile
                245                 250                 255

Gly Asp Arg Ile Tyr Asp Tyr Ala Val Tyr Asn Asp Leu Gly Asn Ile
            260                 265                 270

Glu Gln Asn Glu Lys Phe Glu Arg Pro Asn Leu Gly Gly Asn Asp Met
        275                 280                 285

Tyr His Phe Pro Arg Arg Met Arg Thr Gly Arg Arg Asn Thr Thr Val
    290                 295                 300

Glu Ala Lys Lys Phe Pro Gly Met Val Tyr Glu Thr Arg Lys Thr Lys
305                 310                 315                 320

Gly Asp Phe Tyr Ile Pro Arg Asp Glu Ala Phe Glu Arg Ala Lys Met
                325                 330                 335

Ser Asp Phe Leu Ala Asp Gly Phe Arg Ser Ile Gly His Ser Val Ser
            340                 345                 350

Ser Lys Val Thr Gly Phe Val Thr Arg Lys Gln Glu Phe Asp Thr Val
        355                 360                 365

Glu Glu Ile Lys Lys Leu Tyr Ala Lys Lys Gly Glu Lys Val Gly Gly
    370                 375                 380

Ile Asn Asn Val Leu Pro Asp Lys Glu Asp Ile Pro Glu Gln Glu Gln
385                 390                 395                 400

Tyr Pro Leu Val Phe Leu Gln Glu Val Leu Lys Pro Asp Gly Lys Met
```

```
                    405                 410                 415
Glu His Pro Leu Leu Tyr Pro Leu Pro Gln Leu Leu Gln Ala Asp Asp
                420                 425                 430

Thr Ser Trp Arg Ser Asn Asp Glu Phe Ala Arg Glu Phe Leu Ala Gly
            435                 440                 445

Leu Asn Pro Val Met Ile Thr Arg Val Lys Phe Pro Ile Arg Ser Ser
        450                 455                 460

Leu Asp Pro Ala Glu Phe Gly Asp Pro Thr Ser Ala Ile Thr Lys Asp
465                 470                 475                 480

His Ile Glu Gly Ser Leu Glu Gly Leu Ser Val Glu Glu Ala Val Thr
                485                 490                 495

Ser Asn Arg Leu Phe Val Val Asp Tyr His Asp Ala Phe Leu Pro Phe
            500                 505                 510

Val Ala Lys Ile Asn Ala Gln Gln Asn Ser Ala Thr Tyr Ala Thr Arg
        515                 520                 525

Thr Leu Leu Phe Leu Ser Lys Asp Gly Ile Leu Lys Leu Leu Ala Ile
530                 535                 540

Glu Leu Ala Leu Pro Pro Lys Thr Val Gly Glu Arg Ile Thr Arg
545                 550                 555                 560

Val Leu Thr Thr Arg Lys Asp Asp Gln Leu Trp Lys Val Asn Trp Glu
                565                 570                 575

Trp Glu Leu Ala Lys Ala His Val Ser Asn Asn Asp Ile Thr Ala His
            580                 585                 590

Gln Val Phe Ser His Phe Ser Arg Cys His Ala Val Thr Glu Ala Val
        595                 600                 605

Ile Ile Cys Ser Asn Arg Asn Leu Ser Lys Leu His Pro Leu Met Gln
610                 615                 620

Leu Leu Ala Pro His Phe Lys Ser Thr Leu Glu Ile Asn Arg Gln Ala
625                 630                 635                 640

Arg Ala Thr Leu Ile Ala Ala Gly Gly Ser Ile Glu Thr His Phe Thr
                645                 650                 655

Thr Arg Ala Tyr Ser Leu Glu Met Ala Ala Val Asn Tyr Lys Asp Thr
            660                 665                 670

Trp Thr Phe Glu Ser Gln Ala Leu Pro Thr Asp Leu Val Ala Arg Gly
        675                 680                 685

Met Ala Val Pro Asp Pro Asp Ser Pro His Gly Val Arg Leu Val Val
        690                 695                 700

Glu Asp Tyr Pro Tyr Ala Ala Asp Gly Leu Glu Leu Trp Gly Ala Leu
705                 710                 715                 720

Lys Ala Trp His Lys Glu Tyr Val Asp Ile Tyr Tyr Lys Asp Asp Ala
                725                 730                 735

Ala Val Leu Gln Asp Ser Glu Leu Met Thr Trp Thr Glu Met Arg
            740                 745                 750

Glu Lys Ala His Glu Asp Lys Lys Asp Ser His Gly Trp Pro Glu Leu
        755                 760                 765

Asn Ser Lys Glu Ala Leu Val Asp Ile Leu Thr Thr Val Ile Trp Ile
        770                 775                 780

Pro Ser Cys Leu His Ala Ala Val Asn Phe Gly Gln Tyr Asp Phe Ala
785                 790                 795                 800

Gly Phe Met Pro His His Pro Thr Leu Thr Arg Arg Leu Leu Pro Glu
                805                 810                 815

His Gly Asn Glu Lys Asp Lys Ala Asp Phe Asn Lys Asn Pro Glu Lys
            820                 825                 830
```

```
Tyr Tyr Leu Thr Ser Ile Ser Asn Ile Asp Ser Thr Thr Thr Ala Met
            835                 840                 845

Ser Val Tyr Glu Val Leu Ser Ala His Cys Pro Ile Glu Glu Tyr Ile
850                 855                 860

Gly Glu Arg Arg Gly Asn Trp Thr Asn Asn Glu Lys Val Leu Ala Ala
865                 870                 875                 880

Phe Lys Gly Phe Lys Glu Ser Val Asn Glu Ala Asp Ala Val Met Arg
                885                 890                 895

Ala Arg Asn Ala Asp Pro Lys Leu Arg Asn Arg Gly Gly Pro Val Lys
            900                 905                 910

Met Pro Tyr Gln Leu Leu Arg Pro His Ser Lys Pro Gly Val Thr Ser
            915                 920                 925

Met Gly Val Pro Asn Ser Ile Thr Ile
            930                 935

<210> SEQ ID NO 13
<211> LENGTH: 676
<212> TYPE: PRT
<213> ORGANISM: Homo sapiens

<400> SEQUENCE: 13

Met Ala Glu Phe Arg Val Arg Val Ser Thr Gly Glu Ala Phe Gly Ala
1               5                   10                  15

Gly Thr Trp Asp Lys Val Ser Val Ser Ile Val Gly Thr Arg Gly Glu
                20                  25                  30

Ser Pro Pro Leu Pro Leu Asp Asn Leu Gly Lys Glu Phe Thr Ala Gly
            35                  40                  45

Ala Glu Glu Asp Phe Gln Val Thr Leu Pro Glu Asp Val Gly Arg Val
        50                  55                  60

Leu Leu Leu Arg Val His Lys Ala Pro Pro Val Leu Pro Leu Leu Gly
65                  70                  75                  80

Pro Leu Ala Pro Asp Ala Trp Phe Cys Arg Trp Phe Gln Leu Thr Pro
                85                  90                  95

Pro Arg Gly Gly His Leu Leu Phe Pro Cys Tyr Gln Trp Leu Glu Gly
                100                 105                 110

Ala Gly Thr Leu Val Leu Gln Glu Gly Thr Ala Lys Val Ser Trp Ala
            115                 120                 125

Asp His His Pro Val Leu Gln Gln Arg Gln Glu Glu Leu Gln Ala
        130                 135                 140

Arg Gln Glu Met Tyr Gln Trp Lys Ala Tyr Asn Pro Gly Trp Pro His
145                 150                 155                 160

Cys Leu Asp Glu Lys Thr Val Glu Asp Leu Glu Leu Asn Ile Lys Tyr
                165                 170                 175

Ser Thr Ala Lys Asn Ala Asn Phe Tyr Leu Gln Ala Gly Ser Ala Phe
            180                 185                 190

Ala Glu Met Lys Ile Lys Gly Leu Leu Asp Arg Lys Gly Leu Trp Arg
        195                 200                 205

Ser Leu Asn Glu Met Lys Arg Ile Phe Asn Phe Arg Arg Thr Pro Ala
210                 215                 220

Ala Glu His Ala Phe Glu His Trp Gln Glu Asp Ala Phe Phe Ala Ser
225                 230                 235                 240

Gln Phe Leu Asn Gly Leu Asn Pro Val Leu Ile Arg Arg Cys His Tyr
                245                 250                 255

Leu Pro Lys Asn Phe Pro Val Thr Asp Ala Met Val Ala Ser Val Leu
```

```
            260                 265                 270
Gly Pro Gly Thr Ser Leu Gln Ala Glu Leu Glu Lys Gly Ser Leu Phe
            275                 280                 285
Leu Val Asp His Gly Ile Leu Ser Gly Ile Gln Thr Asn Val Ile Asn
            290                 295                 300
Gly Lys Pro Gln Phe Ser Ala Ala Pro Met Thr Leu Leu Tyr Gln Ser
305                 310                 315                 320
Pro Gly Cys Gly Pro Leu Leu Pro Leu Ala Ile Gln Leu Ser Gln Thr
                325                 330                 335
Pro Gly Pro Asn Ser Pro Ile Phe Leu Pro Thr Asp Asp Lys Trp Asp
            340                 345                 350
Trp Leu Leu Ala Lys Thr Trp Val Arg Asn Ala Glu Phe Ser Phe His
            355                 360                 365
Glu Ala Leu Thr His Leu Leu His Ser His Leu Leu Pro Glu Val Phe
            370                 375                 380
Thr Leu Ala Thr Leu Arg Gln Leu Pro His Cys His Pro Leu Phe Lys
385                 390                 395                 400
Leu Leu Ile Pro His Thr Arg Tyr Thr Leu His Ile Asn Thr Leu Ala
                405                 410                 415
Arg Glu Leu Leu Ile Val Pro Gly Gln Val Val Asp Arg Ser Thr Gly
            420                 425                 430
Ile Gly Ile Glu Gly Phe Ser Glu Leu Ile Gln Arg Asn Met Lys Gln
            435                 440                 445
Leu Asn Tyr Ser Leu Leu Cys Leu Pro Glu Asp Ile Arg Thr Arg Gly
            450                 455                 460
Val Glu Asp Ile Pro Gly Tyr Tyr Tyr Arg Asp Asp Gly Met Gln Ile
465                 470                 475                 480
Trp Gly Ala Val Glu Arg Phe Val Ser Glu Ile Ile Gly Ile Tyr Tyr
                485                 490                 495
Pro Ser Asp Glu Ser Val Gln Asp Asp Arg Glu Leu Gln Ala Trp Val
            500                 505                 510
Arg Glu Ile Phe Ser Lys Gly Phe Leu Asn Gln Glu Ser Ser Gly Ile
            515                 520                 525
Pro Ser Ser Leu Glu Thr Arg Glu Ala Leu Val Gln Tyr Val Thr Met
            530                 535                 540
Val Ile Phe Thr Cys Ser Ala Lys His Ala Ala Val Ser Ala Gly Gln
545                 550                 555                 560
Phe Asp Ser Cys Ala Trp Met Pro Asn Leu Pro Pro Ser Met Gln Leu
                565                 570                 575
Pro Pro Pro Thr Ser Lys Gly Leu Ala Thr Cys Glu Gly Phe Ile Ala
            580                 585                 590
Thr Leu Pro Pro Val Asn Ala Thr Cys Asp Val Ile Leu Ala Leu Trp
            595                 600                 605
Leu Leu Ser Lys Glu Pro Gly Asp Gln Arg Pro Leu Gly Thr Tyr Pro
            610                 615                 620
Asp Glu His Phe Thr Glu Glu Ala Pro Arg Arg Ser Ile Ala Thr Phe
625                 630                 635                 640
Gln Ser Arg Leu Ala Gln Ile Ser Arg Gly Ile Gln Glu Arg Asn Gln
                645                 650                 655
Gly Leu Val Leu Pro Tyr Thr Tyr Leu Asp Pro Pro Leu Ile Glu Asn
            660                 665                 670
Ser Val Ser Ile
            675
```

<210> SEQ ID NO 14
<211> LENGTH: 685
<212> TYPE: PRT
<213> ORGANISM: Pseudomonas aeruginosa

<400> SEQUENCE: 14

```
Met Lys Arg Arg Ser Val Leu Leu Ser Gly Val Ala Leu Ser Gly Thr
1               5                   10                  15

Ala Leu Ala Asn Asp Ser Ile Phe Phe Ser Pro Leu Lys Tyr Leu Gly
            20                  25                  30

Ala Glu Gln Gln Arg Ser Ile Asp Ala Ser Arg Ser Leu Leu Asp Asn
        35                  40                  45

Leu Ile Pro Pro Ser Leu Pro Gln Tyr Asp Asn Leu Ala Gly Lys Leu
    50                  55                  60

Ala Arg Arg Ala Val Leu Thr Ser Lys Lys Leu Val Tyr Val Trp Thr
65                  70                  75                  80

Glu Asn Phe Gly Asn Val Lys Gly Val Pro Met Ala Arg Ser Val Pro
                85                  90                  95

Leu Gly Glu Leu Pro Asn Val Asp Trp Leu Leu Lys Thr Ala Gly Val
            100                 105                 110

Ile Val Glu Leu Ile Val Asn Phe Val Ala Ser Leu Pro Ala Ser Ala
        115                 120                 125

Ala Ala Gln Phe Glu Arg Ile Ala Thr Gly Leu Ser Gly Asp Leu Glu
    130                 135                 140

Ala Ala Arg Gln Val His Glu Ala Leu Leu Glu Glu Ala Lys Asn Asp
145                 150                 155                 160

Pro Ala Ala Gly Ser Leu Leu Arg Phe Thr Glu Leu Gln Thr
                165                 170                 175

Arg Val Ile Ala Ile Leu Thr Arg Val Gly Leu Leu Val Asp Asp Ile
            180                 185                 190

Leu Lys Ser Ala Ser Asn Leu Val Thr Gln Arg Gly Gln Gly Asp Gly
        195                 200                 205

Leu Asn Arg Phe Arg Ala Val Phe Gly Thr Leu Arg Leu Pro Glu Val
    210                 215                 220

Ala Asp Ser Phe Arg Asp Asp Glu Ala Phe Ala Tyr Trp Arg Val Ala
225                 230                 235                 240

Gly Pro Asn Pro Leu Leu Ile Arg Arg Val Asp Ala Leu Pro Ala Asn
                245                 250                 255

Phe Pro Leu Gly Glu Glu Gln Phe Arg Arg Val Met Gly Ala Asp Asp
            260                 265                 270

Ser Leu Leu Glu Ala Ala Ala Ser Arg Arg Leu Tyr Leu Leu Asp Tyr
        275                 280                 285

Ala Glu Leu Gly Lys Leu Ala Pro Ser Gly Ala Val Asp Lys Leu Leu
    290                 295                 300

Thr Gly Thr Gly Phe Ala Tyr Ala Pro Ile Ala Leu Phe Ala Leu Gly
305                 310                 315                 320

Lys Asp Arg Ala Arg Leu Leu Pro Val Ala Ile Gln Cys Gly Gln Asp
                325                 330                 335

Pro Ala Thr His Pro Met Phe Val Arg Pro Ala Glu Ser Glu Ser Asp
            340                 345                 350

Leu Tyr Trp Gly Trp Gln Met Ala Lys Thr Val Val Gln Val Ala Glu
        355                 360                 365

Glu Asn Tyr His Glu Met Phe Val His Leu Ala Gln Thr His Leu Val
```

```
                    370                 375                 380
Ser Glu Ala Phe Cys Leu Ala Thr Gln Arg Thr Leu Ala Pro Ser His
385                 390                 395                 400

Pro Leu His Val Leu Leu Ala Pro His Phe Glu Gly Thr Leu Phe Ile
                405                 410                 415

Asn Glu Gly Ala Ala Arg Ile Leu Leu Pro Ser Ala Gly Phe Ile Asp
                420                 425                 430

Val Met Phe Ala Ala Pro Ile Gln Asp Thr Gln Ala Thr Ala Gly Gly
            435                 440                 445

Asn Arg Leu Gly Phe Asp Phe Tyr Arg Gly Met Leu Pro Glu Ser Leu
        450                 455                 460

Lys Ala Arg Asn Val Asp Asp Pro Leu Ala Leu Pro Asp Tyr Pro Tyr
465                 470                 475                 480

Arg Asp Asp Gly Leu Leu Val Trp Asn Ala Ile Arg Gln Trp Ala Ala
                485                 490                 495

Asp Tyr Val Ala Val Tyr Tyr Ala Ser Asp Gly Asp Val Thr Ala Asp
                500                 505                 510

Val Glu Leu Ala Ala Trp Val Gly Glu Val Ile Gly Ser Gly Lys Val
            515                 520                 525

Ala Gly Phe Arg Pro Ile Thr Gly Arg Ser Gln Leu Val Glu Val Leu
        530                 535                 540

Thr Met Val Ile Phe Thr Ala Ser Ala Gln His Ala Ala Val Asn Phe
545                 550                 555                 560

Pro Gln Pro Ser Met Met Thr Tyr Ala Pro Ala Ile Cys Ala Met Ser
                565                 570                 575

Ala Ala Pro Ala Pro Asp Ser Pro Ser Gly Lys Ser Glu Ala Asp Trp
            580                 585                 590

Leu Lys Met Met Pro Pro Thr Leu Val Ala Leu Glu Lys Val Asn Ile
        595                 600                 605

Tyr His Leu Leu Gly Ser Val Tyr His Gly Arg Leu Gly Asp Tyr Arg
        610                 615                 620

Gln Thr Gly Phe Pro Tyr Ala Pro Val Phe Ser Asp Arg Arg Val Thr
625                 630                 635                 640

Ala Ser Gly Gly Pro Leu Glu Arg Phe Gln Ala Arg Leu Lys Glu Val
                645                 650                 655

Glu Ala Thr Ile Arg Thr Arg Asn Gln Ala Arg Arg Pro Tyr Glu
                660                 665                 670

Tyr Leu Leu Pro Ser Arg Ile Pro Ala Ser Thr Asn Ile
        675                 680                 685

<210> SEQ ID NO 15
<211> LENGTH: 569
<212> TYPE: PRT
<213> ORGANISM: Cyanothece sp.

<400> SEQUENCE: 15

Met Val Gln Pro Ser Leu Pro Gln Asp Asp Thr Pro Asp Gln Gln Glu
1               5                   10                  15

Gln Arg Asn Arg Ala Ile Ala Gln Gln Arg Glu Ala Tyr Gln Tyr Ser
                20                  25                  30

Glu Thr Ala Gly Ile Leu Leu Ile Lys Thr Leu Pro Gln Ser Glu Met
            35                  40                  45

Phe Ser Leu Lys Tyr Leu Ile Glu Arg Asp Lys Gly Leu Val Ser Leu
        50                  55                  60
```

-continued

```
Ile Ala Asn Thr Leu Ala Ser Asn Ile Glu Asn Ile Phe Asp Pro Phe
 65                  70                  75                  80

Asp Lys Leu Glu Asp Phe Glu Glu Met Phe Pro Leu Leu Pro Lys Pro
                 85                  90                  95

Leu Val Met Asn Thr Phe Arg Asn Asp Arg Val Phe Ala Arg Gln Arg
            100                 105                 110

Ile Ala Gly Pro Asn Pro Met Val Ile Glu Arg Val Val Asp Lys Leu
        115                 120                 125

Pro Asp Asn Phe Pro Val Thr Asp Ala Met Phe Gln Lys Ile Met Phe
    130                 135                 140

Thr Lys Lys Thr Leu Ala Glu Ala Ile Ala Gln Gly Lys Leu Phe Ile
145                 150                 155                 160

Thr Asn Tyr Lys Gly Leu Ala Glu Leu Ser Pro Gly Arg Tyr Glu Tyr
                165                 170                 175

Gln Lys Asn Gly Thr Leu Val Gln Lys Thr Lys Thr Ile Ala Ala Pro
            180                 185                 190

Leu Val Leu Tyr Ala Trp Lys Pro Glu Gly Phe Gly Asp Tyr Arg Gly
        195                 200                 205

Ser Leu Ala Pro Ile Ala Ile Gln Ile Asn Gln Gln Pro Asp Pro Ile
    210                 215                 220

Thr Asn Pro Ile Tyr Thr Pro Arg Asp Gly Lys His Trp Phe Ile Ala
225                 230                 235                 240

Lys Ile Phe Ala Gln Met Ala Asp Gly Asn Cys His Glu Ala Ile Ser
                245                 250                 255

His Leu Ala Arg Thr His Leu Ile Leu Glu Pro Phe Val Leu Ala Thr
            260                 265                 270

Ala Asn Glu Leu Ala Pro Asn His Pro Leu Ser Val Leu Leu Lys Pro
        275                 280                 285

His Phe Gln Phe Thr Leu Ala Ile Asn Glu Leu Ala Arg Glu Gln Leu
    290                 295                 300

Ile Ser Ala Gly Gly Tyr Ala Asp Asp Leu Leu Ala Gly Thr Leu Glu
305                 310                 315                 320

Ala Ser Ile Ala Val Ile Lys Ala Ala Ile Lys Glu Tyr Met Asp Asn
                325                 330                 335

Phe Thr Glu Phe Ala Leu Pro Arg Glu Leu Ala Arg Arg Gly Val Gly
            340                 345                 350

Ile Gly Asp Val Asp Gln Arg Gly Glu Asn Phe Leu Pro Asp Tyr Pro
        355                 360                 365

Tyr Arg Asp Asp Ala Met Leu Leu Trp Asn Ala Ile Glu Val Tyr Val
    370                 375                 380

Arg Asp Tyr Leu Ser Leu Tyr Tyr Gln Ser Pro Val Gln Ile Arg Gln
385                 390                 395                 400

Asp Thr Glu Leu Gln Asn Trp Val Arg Arg Leu Val Ser Pro Glu Gly
                405                 410                 415

Gly Arg Val Thr Gly Leu Val Ser Asn Gly Glu Leu Asn Thr Ile Glu
            420                 425                 430

Ala Leu Val Ala Ile Ala Thr Gln Val Ile Phe Val Ser Gly Pro Gln
        435                 440                 445

His Ala Ala Val Asn Tyr Pro Gln Tyr Asp Tyr Met Ala Phe Ile Pro
    450                 455                 460

Asn Met Pro Leu Ala Thr Tyr Ala Thr Pro Pro Asn Lys Glu Ser Asn
465                 470                 475                 480

Ile Ser Glu Ala Thr Ile Leu Asn Ile Leu Pro Pro Gln Lys Leu Ala
```

```
                    485                 490                 495
Ala Arg Gln Leu Glu Leu Met Arg Thr Leu Cys Val Phe Tyr Pro Asn
                500                 505                 510

Arg Leu Gly Tyr Pro Asp Thr Glu Phe Val Asp Val Arg Ala Gln Gln
                515                 520                 525

Val Leu His Gln Phe Gln Glu Arg Leu Gln Glu Ile Glu Gln Arg Ile
            530                 535                 540

Val Leu Cys Asn Glu Lys Arg Leu Glu Pro Tyr Thr Tyr Leu Leu Pro
545                 550                 555                 560

Ser Asn Val Pro Asn Ser Thr Ser Ile
                565

<210> SEQ ID NO 16
<211> LENGTH: 630
<212> TYPE: PRT
<213> ORGANISM: Nostoc punctiforme

<400> SEQUENCE: 16

Met Thr Ala Leu Ser Pro Asp His Ser Ile Ser Ser Ser Thr His
1               5                   10                  15

Thr Leu Asp Ile Ala Arg Gln Glu Tyr Gln Tyr Asn Tyr Asn His Ile
            20                  25                  30

Pro Ser Ile Ala Met Val Asp Arg Leu Ser Ile Thr Glu Glu Phe Thr
        35                  40                  45

Thr Asn Trp Tyr Phe Leu Leu Ala Gln Gln Leu Arg Val Leu Phe Ile
    50                  55                  60

Asn Thr Leu Ile Val Asn Arg Gly Asn Gln Ser Lys Ser Ile Arg
65                  70                  75                  80

Asp Asp Val Glu Arg Phe Ile Leu Glu Ala Leu Leu Lys Gly Ala Val
                85                  90                  95

Pro Ala Arg Ile Ser Ile Leu Ala Arg Ile Leu Gln Ile Ile Pro Gln
            100                 105                 110

Leu Leu Leu Lys Glu Ile Ser Lys Asp Phe Arg Glu Leu Asp Asp Leu
        115                 120                 125

Phe His Ser Ile Leu Lys Glu Asn Gly Leu Ala Ile Leu Arg Asp Ala
    130                 135                 140

Leu Lys Arg Ile Ile Thr Leu Leu Tyr Glu Gly Gln Pro Thr Gly His
145                 150                 155                 160

Ala Thr Ser Leu Lys Asp Tyr Glu Asn Leu Phe Pro Val Ile Ser Leu
                165                 170                 175

Pro Ala Ile Ala Lys Thr Tyr Gln Glu Asp Glu Val Phe Ala Tyr Met
            180                 185                 190

Arg Val Ala Gly Tyr Asn Pro Val Thr Ile Lys Arg Val Thr Thr Leu
        195                 200                 205

Ser Asp Arg Phe Pro Val Thr Asp Glu His Tyr Gln Ala Val Met Gly
    210                 215                 220

Thr Asp Asp Ser Leu Ala Ala Gly Ile Glu Gly Arg Leu Tyr Leu
225                 230                 235                 240

Ala Asp Tyr Lys Ile Leu Asp Gly Ala Ile Asn Gly Thr Phe Pro His
                245                 250                 255

Glu Gln Lys Tyr Leu Tyr Ala Pro Leu Ala Leu Phe Ala Leu Pro Lys
            260                 265                 270

Gly Ser Asp Pro Thr Arg Leu Leu Arg Pro Val Ala Ile Gln Cys Gly
        275                 280                 285
```

Gln Thr Pro Gly Pro Asp Tyr Pro Ile Val Thr Pro Asn Ser Gly Lys
            290                 295                 300

Tyr Ala Trp Leu Phe Ala Lys Thr Ile Val Gln Ile Ala Asp Ala Asn
305                 310                 315                 320

Ile His Glu Ala Val Thr His Leu Ala Arg Thr His Leu Leu Val Gly
                325                 330                 335

Val Phe Ala Ile Ala Thr Ala Arg Gln Leu Pro Leu Thr His Pro Leu
            340                 345                 350

Arg Ile Leu Leu Arg Pro His Phe Asp Ser Thr Leu Ala Ile Asn Asp
        355                 360                 365

Ala Ala Gln Arg Ile Leu Ile Ala Pro Gly Gly Val Asp Arg Leu
370                 375                 380

Leu Ser Ser Ser Ile Asp Asn Ser Arg Val Leu Ala Val Leu Gly Leu
385                 390                 395                 400

Gln Ser Tyr Ser Phe Asn Ser Thr Ile Leu Pro Asn Gln Phe Gln Gln
            405                 410                 415

Arg Gly Val Asp Asp Pro Asn Leu Leu Pro Ile Tyr Pro Tyr Arg Asp
            420                 425                 430

Asp Ala Leu Leu Ile Trp Asn Ala Ile His Gln Trp Val Trp Asp Tyr
            435                 440                 445

Leu Asn Leu Tyr Tyr Thr Thr Asp Glu Asp Ile Gln Lys Asp Arg Ala
450                 455                 460

Leu Gln Ala Trp Ala Ala Glu Ile Pro Ala Tyr Asp Gly Gly Arg Ile
465                 470                 475                 480

Pro Asp Phe Gly Glu Asp Gly Gly Ile Lys Thr Leu Asn Tyr Leu Ile
            485                 490                 495

Asp Ala Thr Thr Leu Ile Ile Phe Thr Ala Ser Ala Gln His Ala Ala
            500                 505                 510

Val Asn Phe Pro Gln Lys Asp Leu Met Gly Tyr Ala Ala Ile Pro
            515                 520                 525

Leu Ala Gly Tyr Leu Pro Ala Ser Thr Leu Lys Arg Glu Val Thr Glu
            530                 535                 540

Gln Asp Tyr Leu Asn Leu Leu Pro Pro Leu Asp Gln Ala Gln Arg Gln
545                 550                 555                 560

Tyr Asn Leu Leu Ser Leu Leu Gly Ser Val Tyr Tyr Asn Lys Leu Gly
            565                 570                 575

Glu Tyr Glu Gln Gly Tyr Phe Thr Asp Glu Lys Val Lys Pro Leu Leu
            580                 585                 590

Gln Ala Phe Gln Ser His Leu Gln Gln Val Glu Asn Thr Ile Lys Gln
            595                 600                 605

Arg Asn Leu His Arg Pro Pro Tyr Glu Tyr Leu Leu Pro Ser Lys Ile
610                 615                 620

Pro Gln Ser Ile Asn Ile
625                 630

<210> SEQ ID NO 17
<211> LENGTH: 936
<212> TYPE: PRT
<213> ORGANISM: Hordeum vulgare

<400> SEQUENCE: 17

Met Leu Thr Ala Thr Lys Pro Leu Val Gly Gly Ala Cys Ala Ala Pro
1               5                   10                  15

Ser Ser Ser Ala Arg Arg Arg Thr Phe Val Val Pro Glu Ala Arg Arg
            20                  25                  30

-continued

```
Lys Pro Gly Asn Gly Arg Arg Thr Ser Val Ser Lys Val Gly Ser Thr
     35                  40                  45
Ser Thr Ser Thr Thr Thr Thr Thr Thr Thr Leu Ser Ala Asp Ser
     50                  55                  60
Asn Gly Ala Ala Val Gly Thr Val Thr Arg Pro Asp Val His Val Gln
 65                  70                  75                  80
Asp Arg Thr His Ala Thr Glu Met Lys Ala Thr Val Thr Val His Met
                 85                  90                  95
Ser Lys Ala Ala Gly Val Arg Asp Phe Leu Tyr Asp Leu Ile Leu Lys
                100                 105                 110
Thr Trp Leu His Val Asp Leu Val Ser Ser Glu Leu Asp Pro Gln Thr
            115                 120                 125
Gly Gln Glu Arg Glu Pro Ile Ser Gly Ala Val Lys His Ser Gly Arg
    130                 135                 140
Val Asp Asp Glu Trp Asp Met Tyr Glu Ala Thr Phe Lys Val Pro Ala
145                 150                 155                 160
Ser Phe Gly Pro Ile Gly Ala Val Gln Val Thr Asn Tyr His His Ser
                165                 170                 175
Glu Met Leu Leu Gly Asp Ile Glu Val Phe Pro Thr Gly Gln Glu Glu
            180                 185                 190
Ser Ala Val Thr Phe His Cys Lys Ser Trp Ile Asp Pro Ser His Cys
    195                 200                 205
Thr Pro Asp Lys Arg Val Phe Phe Pro Ala His Ser Tyr Leu Pro Ser
210                 215                 220
Gln Thr Pro Lys Gly Val Gly Leu Arg Lys Arg Glu Leu Glu Ile
225                 230                 235                 240
Leu Arg Gly Thr Gly Cys Gly Glu Arg Lys Glu His Asp Arg Ile Tyr
                245                 250                 255
Asp Tyr Asp Val Tyr Asn Asp Leu Gly Asn Pro Asp Asp Asn Asn
            260                 265                 270
Pro Thr Thr Arg Pro Val Leu Gly Gly Lys Glu His Pro Tyr Pro Arg
    275                 280                 285
Arg Cys Arg Thr Gly Arg Pro Arg Ser Lys Lys Asp Pro Phe Ser Glu
    290                 295                 300
Glu Arg Ser His Lys Glu His Ile Tyr Val Pro Arg Asp Glu Ala Phe
305                 310                 315                 320
Thr Glu Arg Lys Met Gly Ala Phe Asp Thr Lys Lys Phe Met Ser Gln
                325                 330                 335
Leu His Ala Leu Thr Thr Gly Leu Lys Thr Ala Lys His Lys Ser Gln
            340                 345                 350
Ser Phe Pro Ser Leu Ser Ala Ile Asp Gln Leu Tyr Asp Asp Asn Phe
    355                 360                 365
Arg Asn Gln Pro Val Gln Pro Glu Gly Gly Lys Leu Arg Phe Val Ile
    370                 375                 380
Asp Leu Leu Glu Thr Glu Leu Leu His Leu Phe Lys Leu Glu Gly Ala
385                 390                 395                 400
Ala Phe Leu Glu Gly Ile Arg Arg Val Phe Lys Phe Glu Thr Pro Glu
                405                 410                 415
Ile His Asp Arg Asp Lys Phe Ala Trp Phe Arg Asp Glu Glu Phe Ala
            420                 425                 430
Arg Gln Thr Ile Ala Gly Met Asn Pro Met Ser Ile Gln Leu Val Thr
    435                 440                 445
```

```
Glu Phe Pro Ile Lys Ser Asn Leu Asp Glu Ala Thr Tyr Gly Pro Ala
450                 455                 460
Asp Ser Leu Ile Thr Lys Glu Val Val Glu Gln Ile Arg Arg Val
465                 470                 475             480
Met Thr Ala Asp Glu Ala Val Gln Asn Lys Lys Leu Phe Met Leu Asp
                485                 490                 495
Tyr His Asp Leu Leu Pro Tyr Val His Lys Val Arg Lys Leu Asp
            500                 505                 510
Gly Thr Thr Leu Tyr Gly Ser Arg Ala Leu Phe Phe Leu Thr Ala Asp
                515                 520                 525
Gly Thr Leu Arg Pro Ile Ala Ile Glu Leu Thr Arg Pro Lys Ser Lys
            530                 535                 540
Lys Lys Pro Gln Trp Arg Gln Val Phe Thr Pro Gly Cys Asp Gly Ser
545                 550                 555                 560
Val Thr Gly Ser Trp Leu Trp Gln Leu Ala Lys Ala His Ile Leu Ala
                565                 570                 575
His Asp Ala Gly Val His Gln Leu Val Ser His Trp Leu Arg Thr His
                580                 585                 590
Ala Cys Thr Glu Pro Tyr Ile Ile Ala Ala Asn Arg Gln Leu Ser Gln
            595                 600                 605
Met His Pro Val Tyr Arg Leu Leu His Pro His Phe Arg Phe Thr Met
    610                 615                 620
Glu Ile Asn Ala Gln Ala Arg Ala Met Leu Ile Asn Ala Gly Gly Ile
625                 630                 635                 640
Ile Glu Gly Ser Phe Val Pro Gly Glu Tyr Ser Leu Glu Leu Ser Ser
                645                 650                 655
Val Ala Tyr Asp Gln Gln Trp Arg Phe Asp Met Glu Ala Leu Pro Glu
            660                 665                 670
Asp Leu Ile Arg Arg Gly Met Ala Val Arg Asn Pro Asn Gly Glu Leu
            675                 680                 685
Glu Leu Ala Ile Glu Asp Tyr Pro Tyr Ala Asn Asp Gly Leu Leu Val
            690                 695                 700
Trp Asp Ala Ile Lys Gln Trp Ala Leu Thr Tyr Val Gln His Tyr Tyr
705                 710                 715                 720
Pro Cys Ala Ala Asp Ile Val Asp Asp Glu Glu Leu Gln Ala Trp Trp
                725                 730                 735
Thr Glu Val Arg Thr Lys Gly His Ala Asp Lys Gln Asp Glu Pro Trp
                740                 745                 750
Trp Pro Glu Leu Asp Ser His Glu Asn Leu Ala Gln Thr Leu Ala Thr
            755                 760                 765
Ile Met Trp Val Thr Ser Gly His His Ala Ala Val Asn Phe Gly Gln
770                 775                 780
Tyr Pro Met Ala Gly Tyr Ile Pro Asn Arg Pro Thr Met Ala Arg Arg
785                 790                 795                 800
Asn Met Pro Thr Glu Ile Gly Gly Asp Met Arg Asp Phe Val Glu
                805                 810                 815
Ala Pro Glu Lys Val Leu Leu Asp Thr Phe Pro Ser Gln Tyr Gln Ser
            820                 825                 830
Ala Ile Val Leu Ala Ile Leu Asp Leu Leu Ser Thr His Ser Ser Asp
                835                 840                 845
Glu Glu Tyr Met Gly Thr His Glu Gly Pro Ala Trp Thr Lys Asp Gly
850                 855                 860
Val Ile Asn Gln Ala Phe Glu Glu Phe Lys Glu Ser Thr Arg Lys Ile
```

```
                                 865                  870                  875                  880
Val Glu Gln Val Asp Glu Trp Asn Asn Asp Pro Asp Arg Lys Asn Arg
                    885                  890                  895

His Gly Ala Gly Met Val Pro Tyr Val Leu Leu Arg Pro Ser Asp Gly
            900                  905                  910

Asp Pro Thr Asp Gly Asp Pro Thr Asp Glu Lys Met Val Met Glu Met
                915                  920                  925

Gly Ile Pro Asn Ser Ile Ser Ile
            930             935

<210> SEQ ID NO 18
<211> LENGTH: 1896
<212> TYPE: DNA
<213> ORGANISM: Artificial Sequence
<220> FEATURE:
<223> OTHER INFORMATION: codon optimized artificial DNA sequence

<400> SEQUENCE: 18
```

| | | | | | |
|---|---|---|---|---|---|
| aagcttggat | ccggctcttc | tggtagtgga | gaaaatctat | attttcaagg | aaagatgagc | 60 |
| tattttgatg | cgttcctgtt | ctacattgtt | cacctggttg | ataaactggg | tctgtggcac | 120 |
| cgcttttccg | ttctgctggg | tgtggcgtat | ctggcctgc  | gtcgtcacct | gcaccagcgt | 180 |
| tataacctgg | tgcacgttgg | cccgatcaac | ggtcaaggct | acgacaccga | tgaattctgc | 240 |
| tatcgtaccg | cggacggtaa | atgcaaccac | ccgagcgata | caccatcgg  | tagccagggc | 300 |
| agctttattg | ccgtaacat  | gccgccaagc | accagccaat | acggtattct | ggacccgcac | 360 |
| ccgagcgtgg | ttgcgaccaa | gctgctggcg | cgtaaacgtt | tcatcgacaa | cggtgatcag | 420 |
| tttaacgtga | ttgcgtgcag | ctggatccaa | ttcatgattc | gactgggt   | tgatcacctg | 480 |
| gaagatacc  | accagatcga | actggaagcg | ccggaggaag | tggcgagcgg | ttgcccgctg | 540 |
| aagagcttca | aatttctgcg | taccaagaaa | gttccgaccg | acgatcacca | caaaagcggt | 600 |
| gcggtgaaca | cccgtacccc | gtggtgggac | ggtagcgtta | tctatggcaa | cgatgaaacc | 660 |
| ggtatgcgtc | gtgtgcgtgt | tttcaaggac | ggcaagctga | aaattagcgg | tgacggcctg | 720 |
| ctggagcgtg | atgaacgtgg | cgttccgatc | agcggtgata | ttcgtaacag | ctggagcggt | 780 |
| ttcagcctgc | tgcaagcgct | gtttgttaag | gaacacaaca | gcgtgtgcga | catgctgaaa | 840 |
| gagcgttacc | ggattttga  | cgatgaaaag | ctgtatcgta | ccgcgcgtct | ggtgaccgcg | 900 |
| gcggttatcg | cgaaagtgca | caccatcgac | tggaccattg | agctgctgaa | gaccgatacc | 960 |
| ctgaccgcgg | gcatgcgtat | taactggtac | ggtttctttg | caagaaagt  | taaagacatg | 1020 |
| gtgggtgcgc | gtttcggccc | gctgtttagc | ggtctggttg | gcctgaagaa | accgaacgat | 1080 |
| cacggtgtgc | cgtacagcct | gaccgaggaa | ttcgtgagcg | tttatcgtat | gcactgcctg | 1140 |
| ctgccggaaa | ccctgatcct | gcgtgacatg | aacagcgaga | cgtggataa  | ggaaaacccg | 1200 |
| gcgatcgagc | gtgaaattcc | gatgaccgag | ctgattggta | agaaagcggg | cgaaaaggcg | 1260 |
| agcaaactgg | gctttgagca | gctgctggtg | agcatgggcc | accaaagctg | cggtgcgctg | 1320 |
| accctgtgga | actacccgaa | ctggatgcgt | aacctggttg | cgcaggacat | cgatggcgaa | 1380 |
| gaccgtccgc | acctgatcga | tatggcggcg | ctggagattt | accgtgaccg | tgaacgtggt | 1440 |
| gttccgcgtt | ataacgagtt | ccgtaagaac | ctgctgatga | gcccgattag | caaatgggag | 1500 |
| gaactgaccg | acgatgagga | agcgatcaaa | gttctgcgtg | aggtgtacga | agacgatatt | 1560 |
| gaaaagctgg | acctgaacgt | gggcctgcac | gcggaaaaga | aaatcaaagg | tttcgcgatt | 1620 |
| agcgaaaccg | cgttctttat | ctttctgctg | gttgcgagcc | gtcgtctgga | agcggatcgt | 1680 |

```
ttctttacca ccaactttaa cgagaagacc tataccaaag agggtctgga atgggttaac    1740
accaccgaaa ccctgaagga cgtgattgat cgtcacttcc cgcgtctgac cgaccaatgg    1800
atgcgttgca gcagcgcgtt tagcgtttgg ggtagcgatc cgaatccgaa gaactgggtg    1860
ccgctgtatc tgcgtagcgc gccgtaatga ctcgag                              1896
```

<210> SEQ ID NO 19
<211> LENGTH: 1015
<212> TYPE: PRT
<213> ORGANISM: Arabidopsis thaliana

<400> SEQUENCE: 19

```
Met Gly Ser Ser His His His His His Gly Thr Lys Thr Glu Glu
1               5                   10                  15

Gly Lys Leu Val Ile Trp Ile Asn Gly Asp Lys Gly Tyr Asn Gly Leu
            20                  25                  30

Ala Glu Val Gly Lys Lys Phe Glu Lys Asp Thr Gly Ile Lys Val Thr
        35                  40                  45

Val Glu His Pro Asp Lys Leu Glu Glu Lys Phe Pro Gln Val Ala Ala
    50                  55                  60

Thr Gly Asp Gly Pro Asp Ile Ile Phe Trp Ala His Asp Arg Phe Gly
65                  70                  75                  80

Gly Tyr Ala Gln Ser Gly Leu Leu Ala Glu Ile Thr Pro Asp Lys Ala
                85                  90                  95

Phe Gln Asp Lys Leu Tyr Pro Phe Thr Trp Asp Ala Val Arg Tyr Asn
            100                 105                 110

Gly Lys Leu Ile Ala Tyr Pro Ile Ala Val Glu Ala Leu Ser Leu Ile
        115                 120                 125

Tyr Asn Lys Asp Leu Leu Pro Asn Pro Lys Thr Trp Glu Glu Ile
    130                 135                 140

Pro Ala Leu Asp Lys Glu Leu Lys Ala Lys Gly Lys Ser Ala Leu Met
145                 150                 155                 160

Phe Asn Leu Gln Glu Pro Tyr Phe Thr Trp Pro Leu Ile Ala Ala Asp
                165                 170                 175

Gly Gly Tyr Ala Phe Lys Tyr Glu Asn Gly Lys Tyr Asp Ile Lys Asp
            180                 185                 190

Val Gly Val Asp Asn Ala Gly Ala Lys Ala Gly Leu Thr Phe Leu Val
        195                 200                 205

Asp Leu Ile Lys Asn Lys His Met Asn Ala Asp Thr Asp Tyr Ser Ile
    210                 215                 220

Ala Glu Ala Ala Phe Asn Lys Gly Glu Thr Ala Met Thr Ile Asn Gly
225                 230                 235                 240

Pro Trp Ala Trp Ser Asn Ile Asp Thr Ser Lys Val Asn Tyr Gly Val
                245                 250                 255

Thr Val Leu Pro Thr Phe Lys Gly Gln Pro Ser Lys Pro Phe Val Gly
            260                 265                 270

Val Leu Ser Ala Gly Ile Asn Ala Ala Ser Pro Asn Lys Glu Leu Ala
        275                 280                 285

Lys Glu Phe Leu Glu Asn Tyr Leu Leu Thr Asp Glu Gly Leu Glu Ala
    290                 295                 300

Val Asn Lys Asp Lys Pro Leu Gly Ala Val Ala Leu Lys Ser Tyr Glu
305                 310                 315                 320

Glu Glu Leu Ala Lys Asp Pro Arg Ile Ala Ala Thr Met Glu Asn Ala
                325                 330                 335
```

```
Gln Lys Gly Glu Ile Met Pro Asn Ile Pro Gln Met Ser Ala Phe Trp
            340                 345                 350

Tyr Ala Val Arg Thr Ala Val Ile Asn Ala Ala Ser Gly Arg Gln Thr
            355                 360                 365

Val Asp Glu Ala Leu Lys Asp Ala Gln Thr Gly Thr Asp Tyr Asp Ile
            370                 375                 380

Pro Thr Thr Lys Leu Gly Ser Gly Ser Gly Ser Gly Glu Asn Leu
385                 390                 395                 400

Tyr Phe Gln Gly Lys Met Ser Tyr Phe Asp Ala Phe Leu Phe Tyr Ile
            405                 410                 415

Val His Leu Val Asp Lys Leu Gly Leu Trp His Arg Phe Pro Val Leu
            420                 425                 430

Leu Gly Val Ala Tyr Leu Gly Leu Arg Arg His Leu His Gln Arg Tyr
            435                 440                 445

Asn Leu Val His Val Gly Pro Ile Asn Gly Gln Gly Tyr Asp Thr Asp
            450                 455                 460

Glu Phe Cys Tyr Arg Thr Ala Asp Gly Lys Cys Asn His Pro Ser Asp
465                 470                 475                 480

Asn Thr Ile Gly Ser Gln Gly Ser Phe Ile Gly Arg Asn Met Pro Pro
            485                 490                 495

Ser Thr Ser Gln Tyr Gly Ile Leu Asp Pro His Pro Ser Val Val Ala
            500                 505                 510

Thr Lys Leu Leu Ala Arg Lys Arg Phe Ile Asp Asn Gly Asp Gln Phe
            515                 520                 525

Asn Val Ile Ala Cys Ser Trp Ile Gln Phe Met Ile His Asp Trp Val
            530                 535                 540

Asp His Leu Glu Asp Thr His Gln Ile Glu Leu Glu Ala Pro Glu Glu
545                 550                 555                 560

Val Ala Ser Gly Cys Pro Leu Lys Ser Phe Lys Phe Leu Arg Thr Lys
            565                 570                 575

Lys Val Pro Thr Asp His His Lys Ser Gly Ala Val Asn Thr Arg
            580                 585                 590

Thr Pro Trp Trp Asp Gly Ser Val Ile Tyr Gly Asn Asp Glu Thr Gly
            595                 600                 605

Met Arg Arg Val Arg Val Phe Lys Asp Gly Lys Leu Lys Ile Ser Gly
            610                 615                 620

Asp Gly Leu Leu Glu Arg Asp Glu Arg Gly Val Pro Ile Ser Gly Asp
625                 630                 635                 640

Ile Arg Asn Ser Trp Ser Gly Phe Ser Leu Leu Gln Ala Leu Phe Val
            645                 650                 655

Lys Glu His Asn Ser Val Cys Asp Met Leu Lys Glu Arg Tyr Pro Asp
            660                 665                 670

Phe Asp Asp Glu Lys Leu Tyr Arg Thr Ala Arg Leu Val Thr Ala Ala
            675                 680                 685

Val Ile Ala Lys Val His Thr Ile Asp Trp Thr Ile Glu Leu Leu Lys
            690                 695                 700

Thr Asp Thr Leu Thr Ala Gly Met Arg Ile Asn Trp Tyr Gly Phe Phe
705                 710                 715                 720

Gly Lys Lys Val Lys Asp Met Val Gly Ala Arg Phe Gly Pro Leu Phe
            725                 730                 735

Ser Gly Leu Val Gly Leu Lys Lys Pro Asn Asp His Gly Val Pro Tyr
            740                 745                 750
```

Ser Leu Thr Glu Glu Phe Val Ser Val Tyr Arg Met His Cys Leu Leu
            755                 760                 765

Pro Glu Thr Leu Ile Leu Arg Asp Met Asn Ser Glu Asn Val Asp Lys
    770                 775                 780

Glu Asn Pro Ala Ile Glu Arg Glu Ile Pro Met Thr Glu Leu Ile Gly
785                 790                 795                 800

Lys Lys Ala Gly Glu Lys Ala Ser Lys Leu Gly Phe Glu Gln Leu Leu
                805                 810                 815

Val Ser Met Gly His Gln Ser Cys Gly Ala Leu Thr Leu Trp Asn Tyr
            820                 825                 830

Pro Asn Trp Met Arg Asn Leu Val Ala Gln Asp Ile Asp Gly Glu Asp
        835                 840                 845

Arg Pro His Leu Ile Asp Met Ala Ala Leu Glu Ile Tyr Arg Asp Arg
    850                 855                 860

Glu Arg Gly Val Pro Arg Tyr Asn Glu Phe Arg Lys Asn Leu Leu Met
865                 870                 875                 880

Ser Pro Ile Ser Lys Trp Glu Glu Leu Thr Asp Asp Glu Glu Ala Ile
                885                 890                 895

Lys Val Leu Arg Glu Val Tyr Glu Asp Asp Ile Glu Lys Leu Asp Leu
            900                 905                 910

Asn Val Gly Leu His Ala Glu Lys Lys Ile Lys Gly Phe Ala Ile Ser
        915                 920                 925

Glu Thr Ala Phe Phe Ile Phe Leu Leu Val Ala Ser Arg Arg Leu Glu
    930                 935                 940

Ala Asp Arg Phe Phe Thr Thr Asn Phe Asn Glu Lys Thr Tyr Thr Lys
945                 950                 955                 960

Glu Gly Leu Glu Trp Val Asn Thr Thr Glu Thr Leu Lys Asp Val Ile
                965                 970                 975

Asp Arg His Phe Pro Arg Leu Thr Asp Gln Trp Met Arg Cys Ser Ser
            980                 985                 990

Ala Phe Ser Val Trp Gly Ser Asp Pro Asn Pro Lys Asn Trp Val Pro
        995                 1000                1005

Leu Tyr  Leu Arg Ser Ala Pro
   1010             1015

<210> SEQ ID NO 20
<211> LENGTH: 1926
<212> TYPE: DNA
<213> ORGANISM: Artificial Sequence
<220> FEATURE:
<223> OTHER INFORMATION: codon optimized artificial DNA sequence

<400> SEQUENCE: 20
aagcttggat ccggctcttc tggtagtgga gaaaatctat attttcaagg agattttcac      60
gaaatatacg ctagaatgag cctgctggat cgttttctgc tgctgatcgt gcacggtgtt     120
gacaagatgg tgccgtggca caaactgccg gttttcctgg cctgacctac ctggaagtg     180 cgtcgtcacc tgcaccagca atataacctg ctgaacgttg gtcagacccc gaccggcatc     240
cgttttgacc ggcgaactac cccgtatcgt accgcggatg gcaagttcaa cgacccgttt     300
aacgagggtg tgggcagcca gacagcttc tttggccgta actgcccgcc ggttgatcaa     360
aagagcaaac tgcgtcgtcc ggacccgatg gtggttgcga ccaagctgct gggtcgtaag     420
aaattcattg ataccggcaa acagtttaac atgatcgcgg cgagctggat ccaattcatg     480
attcacgatt ggatcgacca cctggaggac acccaccaga tcgaactggt ggcgccgaaa     540

```
gaggtggcga gcaaatgccc gctgagcagc ttccgttttc tgaagaccaa agaagtgccg    600
accggtttct ttgagattaa aaccggcagc caaaacatcc gtaccccgtg gtgggatagc    660
agcgtgattt acggtagcaa cagcaagacc ctggatcgtg ttcgtaccta taaagacggc    720
aagctgaaaa tcagcgagga aaccggcctg ctgctgcacg atgaagacgg tctggcgatt    780
agcggtgaca ttcgtaacag ctgggcgggc gtgagcgcgc tgcaggcgct gttcattaag    840
gaacacaacg cggtttgcga tgcgctgaaa gacgaggacg atgacctgga ggatgaagac    900
ctgtaccgtt atgcgcgtct ggtgaccagc gcggtggttg cgaagatcca caccattgat    960
tggaccgttc agctgctgaa aaccgacacc ctgctggcgg gtatgcgtgc gaactggtac   1020
ggtctgctgg gcaagaaatt caaggatagc tttggtcatg cgggtagcag catcctgggt   1080
ggcgtggttg gtatgaagaa accgcaaaac cacggcgtgc cgtacagcct gaccgaagac   1140
ttcaccagcg tttatcgtat gcacagcctg ctgccggatc agctgcacat cctggacatt   1200
gatgacgtgc cgggtaccaa caaaagcctg ccgctgatcc aagagattag catgcgtgac   1260
ctgattggtc gtaagggcga ggaaaccatg agccacatcg gctttaccaa actgatggtt   1320
agcatgggtc accaggcgag cggtgcgctg gaactgatga actatccgat gtggctgcgt   1380
gatattgttc gcatgacccc gaacggtcaa gcgcgtccgg atcatgttga cctggcggcg   1440
ctggaaatct accgtgatcg tgagcgtagc gtgccgcgtt ataacgaatt ccgtcgtagc   1500
atgtttatga tcccgattac caagtgggag gatctgaccg aagacgagga agcgatcgag   1560
gtgctggatg acgtttacga tggtgacgtg gaggaactgg acctgctggt tggtctgatg   1620
gcggaaaaga aaattaaagg cttcgcgatc agcgagaccg cgttctatat ctttctgatt   1680
atggcgaccc gtcgtctgga agcggatcgt ttctttacca gcgactttaa cgagaccatt   1740
tacaccaaga aaggcctgga atgggtgaac accaccgaga gcctgaagga tgttatcgac   1800
cgtcactatc cggatatgac cgacaaatgg atgaacagcg agagcgcgtt cagcgtttgg   1860
gacagcccgc cgctgaccaa gaacccgatt ccgctgtacc tgcgtatccc gagctaatga   1920
ctcgag                                                              1926
```

<210> SEQ ID NO 21
<211> LENGTH: 1025
<212> TYPE: PRT
<213> ORGANISM: Arabidopsis thaliana

<400> SEQUENCE: 21

Met Gly Ser Ser His His His His His His Gly Thr Lys Thr Glu Glu
1               5                   10                  15

Gly Lys Leu Val Ile Trp Ile Asn Gly Asp Lys Gly Tyr Asn Gly Leu
            20                  25                  30

Ala Glu Val Gly Lys Lys Phe Glu Lys Asp Thr Gly Ile Lys Val Thr
        35                  40                  45

Val Glu His Pro Asp Lys Leu Glu Glu Lys Phe Pro Gln Val Ala Ala
    50                  55                  60

Thr Gly Asp Gly Pro Asp Ile Ile Phe Trp Ala His Asp Arg Phe Gly
65                  70                  75                  80

Gly Tyr Ala Gln Ser Gly Leu Leu Ala Glu Ile Thr Pro Asp Lys Ala
                85                  90                  95

Phe Gln Asp Lys Leu Tyr Pro Phe Thr Trp Asp Ala Val Arg Tyr Asn
            100                 105                 110

Gly Lys Leu Ile Ala Tyr Pro Ile Ala Val Glu Ala Leu Ser Leu Ile
        115                 120                 125

Tyr Asn Lys Asp Leu Leu Pro Asn Pro Pro Lys Thr Trp Glu Glu Ile
        130                 135                 140

Pro Ala Leu Asp Lys Glu Leu Lys Ala Lys Gly Lys Ser Ala Leu Met
145                 150                 155                 160

Phe Asn Leu Gln Glu Pro Tyr Phe Thr Trp Pro Leu Ile Ala Ala Asp
                165                 170                 175

Gly Gly Tyr Ala Phe Lys Tyr Glu Asn Gly Lys Tyr Asp Ile Lys Asp
                180                 185                 190

Val Gly Val Asp Asn Ala Gly Ala Lys Ala Gly Leu Thr Phe Leu Val
        195                 200                 205

Asp Leu Ile Lys Asn Lys His Met Asn Ala Asp Thr Ala Tyr Ser Ile
210                 215                 220

Ala Glu Ala Ala Phe Asn Lys Gly Glu Thr Ala Met Thr Ile Asn Gly
225                 230                 235                 240

Pro Trp Ala Trp Ser Asn Ile Asp Thr Ser Lys Val Asn Tyr Gly Val
                245                 250                 255

Thr Val Leu Pro Thr Phe Lys Gly Gln Pro Ser Lys Pro Phe Val Gly
                260                 265                 270

Val Leu Ser Ala Gly Ile Asn Ala Ala Ser Pro Asn Lys Glu Leu Ala
        275                 280                 285

Lys Glu Phe Leu Glu Asn Tyr Leu Leu Thr Asp Glu Gly Leu Glu Ala
        290                 295                 300

Val Asn Lys Asp Lys Pro Leu Gly Ala Val Ala Leu Lys Ser Tyr Glu
305                 310                 315                 320

Glu Glu Leu Ala Lys Asp Pro Arg Ile Ala Ala Thr Met Glu Asn Ala
                325                 330                 335

Gln Lys Gly Glu Ile Met Pro Asn Ile Pro Gln Met Ser Ala Phe Trp
                340                 345                 350

Tyr Ala Val Arg Thr Ala Val Ile Asn Ala Ala Ser Gly Arg Gln Thr
        355                 360                 365

Val Asp Glu Ala Leu Lys Asp Ala Gln Thr Gly Thr Asp Tyr Asp Ile
        370                 375                 380

Pro Thr Thr Lys Leu Gly Ser Gly Ser Gly Ser Gly Glu Asn Leu
385                 390                 395                 400

Tyr Phe Gln Gly Asp Phe His Glu Ile Tyr Ala Arg Met Ser Leu Leu
                405                 410                 415

Asp Arg Phe Leu Leu Leu Ile Val His Gly Val Asp Lys Met Val Pro
                420                 425                 430

Trp His Lys Leu Pro Val Phe Leu Gly Leu Thr Tyr Leu Glu Val Arg
        435                 440                 445

Arg His Leu His Gln Tyr Asn Leu Leu Asn Val Gly Gln Thr Pro
        450                 455                 460

Thr Gly Ile Arg Phe Asp Pro Ala Asn Tyr Pro Tyr Arg Thr Ala Asp
465                 470                 475                 480

Gly Lys Phe Asn Asp Pro Phe Asn Glu Gly Val Gly Ser Gln Asn Ser
                485                 490                 495

Phe Phe Gly Arg Asn Cys Pro Pro Val Asp Gln Lys Ser Lys Leu Arg
                500                 505                 510

Arg Pro Asp Pro Met Val Val Ala Thr Lys Leu Leu Gly Arg Lys Lys
        515                 520                 525

Phe Ile Asp Thr Gly Lys Gln Phe Asn Met Ile Ala Ala Ser Trp Ile
530                 535                 540

```
Gln Phe Met Ile His Asp Trp Ile Asp His Leu Glu Asp Thr His Gln
545                 550                 555                 560

Ile Glu Leu Val Ala Pro Lys Glu Val Ala Ser Lys Cys Pro Leu Ser
        565                 570                 575

Ser Phe Arg Phe Leu Lys Thr Lys Glu Val Pro Thr Gly Phe Phe Glu
            580                 585                 590

Ile Lys Thr Gly Ser Gln Asn Ile Arg Thr Pro Trp Trp Asp Ser Ser
    595                 600                 605

Val Ile Tyr Gly Ser Asn Ser Lys Thr Leu Asp Arg Val Arg Thr Tyr
        610                 615                 620

Lys Asp Gly Lys Leu Lys Ile Ser Glu Thr Gly Leu Leu His
625                 630                 635                 640

Asp Glu Asp Gly Leu Ala Ile Ser Gly Asp Ile Arg Asn Ser Trp Ala
                645                 650                 655

Gly Val Ser Ala Leu Gln Ala Leu Phe Ile Lys Glu His Asn Ala Val
                660                 665                 670

Cys Asp Ala Leu Lys Asp Glu Asp Asp Leu Glu Asp Glu Asp Leu
            675                 680                 685

Tyr Arg Tyr Ala Arg Leu Val Thr Ser Ala Val Val Ala Lys Ile His
    690                 695                 700

Thr Ile Asp Trp Thr Val Gln Leu Leu Lys Thr Asp Thr Leu Leu Ala
705                 710                 715                 720

Gly Met Arg Ala Asn Trp Tyr Gly Leu Leu Gly Lys Lys Phe Lys Asp
                725                 730                 735

Ser Phe Gly His Ala Gly Ser Ser Ile Leu Gly Gly Val Val Gly Met
            740                 745                 750

Lys Lys Pro Gln Asn His Gly Val Pro Tyr Ser Leu Thr Glu Asp Phe
    755                 760                 765

Thr Ser Val Tyr Arg Met His Ser Leu Leu Pro Asp Gln Leu His Ile
770                 775                 780

Leu Asp Ile Asp Asp Val Pro Gly Thr Asn Lys Ser Leu Pro Leu Ile
785                 790                 795                 800

Gln Glu Ile Ser Met Arg Asp Leu Ile Gly Arg Lys Gly Glu Glu Thr
                805                 810                 815

Met Ser His Ile Gly Phe Thr Lys Leu Met Val Ser Met Gly His Gln
            820                 825                 830

Ala Ser Gly Ala Leu Glu Leu Met Asn Tyr Pro Met Trp Leu Arg Asp
            835                 840                 845

Ile Val Pro His Asp Pro Asn Gly Gln Ala Arg Pro Asp His Val Asp
    850                 855                 860

Leu Ala Ala Leu Glu Ile Tyr Arg Asp Arg Glu Arg Ser Val Pro Arg
865                 870                 875                 880

Tyr Asn Glu Phe Arg Arg Ser Met Phe Met Ile Pro Ile Thr Lys Trp
            885                 890                 895

Glu Asp Leu Thr Glu Asp Glu Ala Ile Glu Val Leu Asp Asp Val
                900                 905                 910

Tyr Asp Gly Asp Val Glu Glu Leu Asp Leu Leu Val Gly Leu Met Ala
            915                 920                 925

Glu Lys Lys Ile Lys Gly Phe Ala Ile Ser Glu Thr Ala Phe Tyr Ile
            930                 935                 940

Phe Leu Ile Met Ala Thr Arg Arg Leu Glu Ala Asp Arg Phe Phe Thr
945                 950                 955                 960

Ser Asp Phe Asn Glu Thr Ile Tyr Thr Lys Lys Gly Leu Glu Trp Val
```

965                 970                 975
Asn Thr Thr Glu Ser Leu Lys Asp Val Ile Asp Arg His Tyr Pro Asp
            980                 985                 990

Met Thr Asp Lys Trp Met Asn Ser Glu Ser Ala Phe Ser Val Trp Asp
        995                 1000                1005

Ser Pro Pro Leu Thr Lys Asn Pro Ile Pro Leu Tyr Leu Arg Ile
    1010                1015                1020

Pro Ser
    1025

<210> SEQ ID NO 22
<211> LENGTH: 1890
<212> TYPE: DNA
<213> ORGANISM: Artificial Sequence
<220> FEATURE:
<223> OTHER INFORMATION: codon optimized artificial DNA sequence

<400> SEQUENCE: 22
catatgcacc accaccacca ccacatggga tcagggctat ttaaacccag ggttcacccg      60
gacctgcgtg atgtgtttag caagatgagc ttctttgaca aaattggttt cctgtttatc     120
cacgcgttcg ataagcgtaa cctgtggcac aaagtgccgg ttccgatcgg cctgctgtac     180
ctgaacaccc gtcgtaccct gctggagaaa tataacctgc tggcggttgg tcgtagcagc     240
catggtgcgc tgtttgaccc gaaggagttt ctgtaccgta ccaagacgg taaatataac      300 gatccgcaca acgcggaagc gggtagccag aacaccttct ttggccgtaa catggagccg     360
gtggaccagc aagatgaact gatgagcccg gacccgtttg tggttgcgac aagctgctg      420 gcgcgtcgtg agtataagga taccggtaaa cagttcaaca ttctggcggc ggcgtggatc     480
caatttatgg ttcacgactg gatggatcac atggaagaca ccgtcaaat cggcattacc      540 gcgccgaaag aggtggcgaa cgaatgcccg ctgaagagct caaatttca cccgaccaag      600 gagctgccga ccaacagcga cggtatcaaa attggccact acaacattcg taccgcgtgg     660
tgggatggta gcgcggttta tggcaacaac gaggaacgtg cggagaagct gcgtacctac     720
gttgacggta aactggtgat cggtgacgat ggcctgctgc tgcacaagga aaacggtgtt     780
gcgctgagcg gcgatattcg taacagctgg gcgggcgtga gcatcctgca ggcgctgttc     840
gttaaggagc acaacgcggt gtgcgacgcg atcaaagagg aacacccgaa cctgagcgat     900
gaggaactgt accgttatgc gaagctggtg accagcgcgg ttattgcgaa agtgcacacc     960
atcgactgga ccgttgaact gctgaagacc aaaaccatgc gtgcggcgat gcgtgcgaac    1020
tggtacggtc tgctgggcaa gaaaattaaa gataccttcg gtcacattgg tgcccgatc     1080 ctgggtggcc tggttggtct gaagaaaccg aacaaccacg gcgtgccgta cagcctgacc    1140
gaggaattta ccagcgtgta tcgtatgcac agcctgatcc gagcaccct gaagctgcgt     1200 gacccgaccg gtcagccgga tgcgaacaac agcccgccgt gcctggagga catcgatatt    1260
ggtgaaatga ttggtctgaa aggcgaggaa caactgagca gatcggctt cgagaaacag     1320 gcgctgagca tgggttacca gcgtgcggc gcgctggaac tgtggaacta ccgagcttc     1380 tttcgtaacc tgattccgca gaacctggac ggtaccaacc gtagcgaccg tatcgatctg    1440
gcggcgctgg aagtgtaccg tgatcgtgaa cgtagcgtgc gcgttataa cgagttccgt     1500 cgtcgtctgt tcctgatccc gattaagagc tgggaggacc tgaccagcga caaagatgcg    1560
atcgaaacca ttcgtgcgat ctatggtgac gatgttgaaa gctggacct gctggttggt    1620 ctgatggcgg agaagaaaat taaaggcttc gcgatcagcg aaaccgcgtt caacatcttt    1680

-continued

```
attctgatgg cgagccgtcg tctggaagcg gaccgtttct ttaccagcaa ctttaacgag   1740
gaaacctaca ccaagaaagg tatgcaatgg gttaagacca ccgagggcct gcgtgatgtg   1800
attaaccgtc actatccgga aatcaccgcg aagtggatga aaagcagcag cgcgttcagc   1860
gtgtgggatg cggattacta atgaaagctt                                    1890
```

<210> SEQ ID NO 23
<211> LENGTH: 625
<212> TYPE: PRT
<213> ORGANISM: Oryza sativa

<400> SEQUENCE: 23

```
Met His His His His His Met Gly Ser Gly Leu Phe Lys Pro Arg
1               5                   10                  15

Val His Pro Asp Leu Arg Asp Val Phe Ser Lys Met Ser Phe Asp
                20                  25                  30

Lys Ile Gly Phe Leu Phe Ile His Ala Phe Asp Lys Arg Asn Leu Trp
        35                  40                  45

His Lys Val Pro Val Pro Ile Gly Leu Leu Tyr Leu Asn Thr Arg Arg
50                  55                  60

Thr Leu Leu Glu Lys Tyr Asn Leu Leu Ala Val Gly Arg Ser Ser His
65                  70                  75                  80

Gly Ala Leu Phe Asp Pro Lys Glu Phe Leu Tyr Arg Thr Glu Asp Gly
                85                  90                  95

Lys Tyr Asn Asp Pro His Asn Ala Glu Ala Gly Ser Gln Asn Thr Phe
            100                 105                 110

Phe Gly Arg Asn Met Glu Pro Val Asp Gln Gln Asp Glu Leu Met Ser
        115                 120                 125

Pro Asp Pro Phe Val Val Ala Thr Lys Leu Leu Ala Arg Arg Glu Tyr
    130                 135                 140

Lys Asp Thr Gly Lys Gln Phe Asn Ile Leu Ala Ala Trp Ile Gln
145                 150                 155                 160

Phe Met Val His Asp Trp Met Asp His Met Glu Asp Thr Gly Gln Ile
                165                 170                 175

Gly Ile Thr Ala Pro Lys Glu Val Ala Asn Glu Cys Pro Leu Lys Ser
            180                 185                 190

Phe Lys Phe His Pro Thr Lys Glu Leu Pro Thr Asn Ser Asp Gly Ile
        195                 200                 205

Lys Ile Gly His Tyr Asn Ile Arg Thr Ala Trp Trp Asp Gly Ser Ala
    210                 215                 220

Val Tyr Gly Asn Asn Glu Glu Arg Ala Glu Lys Leu Arg Thr Tyr Val
225                 230                 235                 240

Asp Gly Lys Leu Val Ile Gly Asp Asp Gly Leu Leu His Lys Glu
                245                 250                 255

Asn Gly Val Ala Leu Ser Gly Asp Ile Arg Asn Ser Trp Ala Gly Val
            260                 265                 270

Ser Ile Leu Gln Ala Leu Phe Val Lys Glu His Asn Ala Val Cys Asp
        275                 280                 285

Ala Ile Lys Glu Glu His Pro Asn Leu Ser Asp Glu Leu Tyr Arg
    290                 295                 300

Tyr Ala Lys Leu Val Thr Ser Ala Val Ile Ala Lys Val His Thr Ile
305                 310                 315                 320

Asp Trp Thr Val Glu Leu Leu Lys Thr Lys Thr Met Arg Ala Ala Met
                325                 330                 335
```

-continued

```
Arg Ala Asn Trp Tyr Gly Leu Leu Gly Lys Lys Ile Lys Asp Thr Phe
            340                 345                 350

Gly His Ile Gly Gly Pro Ile Leu Gly Gly Leu Val Gly Leu Lys Lys
        355                 360                 365

Pro Asn Asn His Gly Val Pro Tyr Ser Leu Thr Glu Glu Phe Thr Ser
    370                 375                 380

Val Tyr Arg Met His Ser Leu Ile Pro Ser Thr Leu Lys Leu Arg Asp
385                 390                 395                 400

Pro Thr Gly Gln Pro Asp Ala Asn Asn Ser Pro Pro Cys Leu Glu Asp
                405                 410                 415

Ile Asp Ile Gly Glu Met Ile Gly Leu Lys Gly Glu Glu Gln Leu Ser
            420                 425                 430

Lys Ile Gly Phe Glu Lys Gln Ala Leu Ser Met Gly Tyr Gln Ala Cys
            435                 440                 445

Gly Ala Leu Glu Leu Trp Asn Tyr Pro Ser Phe Phe Arg Asn Leu Ile
    450                 455                 460

Pro Gln Asn Leu Asp Gly Thr Asn Arg Ser Asp Arg Ile Asp Leu Ala
465                 470                 475                 480

Ala Leu Glu Val Tyr Arg Asp Arg Glu Arg Ser Val Pro Arg Tyr Asn
                485                 490                 495

Glu Phe Arg Arg Arg Leu Phe Leu Ile Pro Ile Lys Ser Trp Glu Asp
            500                 505                 510

Leu Thr Ser Asp Lys Asp Ala Ile Glu Thr Ile Arg Ala Ile Tyr Gly
            515                 520                 525

Asp Asp Val Glu Lys Leu Asp Leu Leu Val Gly Leu Met Ala Glu Lys
            530                 535                 540

Lys Ile Lys Gly Phe Ala Ile Ser Glu Thr Ala Phe Asn Ile Phe Ile
545                 550                 555                 560

Leu Met Ala Ser Arg Arg Leu Glu Ala Asp Arg Phe Phe Thr Ser Asn
                565                 570                 575

Phe Asn Glu Glu Thr Tyr Thr Lys Lys Gly Met Gln Trp Val Lys Thr
            580                 585                 590

Thr Glu Gly Leu Arg Asp Val Ile Asn Arg His Tyr Pro Glu Ile Thr
            595                 600                 605

Ala Lys Trp Met Lys Ser Ser Ser Ala Phe Ser Val Trp Asp Ala Asp
    610                 615                 620

Tyr
625
```

DETERGENT COMPOSITION

REFERENCE TO A SEQUENCE LISTING

This application contains a Sequence Listing in computer readable form. The computer readable form is incorporated herein by reference.

FIELD OF THE INVENTION

The present invention relates to a liquid detergent composition comprising a surfactant system, one or more hydroperoxy fatty acid producing enzymes selected from the group consisting of: arachidonate lipoxygenases, alpha-dioxygenases, and mixtures thereof, preferably alpha-dioxygenases, and a liquid carrier (i.e., water). The composition provides one or more benefits, including good cleaning particularly good grease emulsification, and long lasting suds especially in presence of greasy soils.

BACKGROUND OF THE INVENTION

Liquid detergent compositions should have a good suds profile in particular a long lasting suds profile especially in the presence of greasy soils while providing good soil and/or grease cleaning. Users usually see suds as an indicator of the performance of the liquid detergent composition. Moreover, the user of a liquid detergent composition may also use the suds profile and the appearance of the suds (e.g., density, whiteness) as an indicator that the wash solution still contains active detergent ingredients. This is particularly the case for manual washing, also referred to herein as hand-washing, where the user usually doses the liquid detergent composition depending on the suds remaining and renews the wash solution when the suds subsides or when the suds does not look thick enough. Thus, a liquid detergent composition, particularly a liquid manual wash detergent composition that generates little or low density suds would tend to be replaced by the user more frequently than is necessary. Accordingly, it is desirable for a liquid detergent composition to provide "good sudsing profile", which includes good suds height and/or density as well as good suds duration during the initial mixing of the liquid detergent with water and/or during the entire washing operation.

The need also exists for an improved liquid detergent composition, when used in a manual-washing process, the composition preferably also provides a pleasant washing experience, i.e, good feel on the user's hands during the wash. Preferably liquid detergent compositions are also easy to rinse. Further it is desirous that the improved liquid detergent composition is stable and will not phase separate, resulting in greater shelf-life of the product. Preferably in addition, the composition provides a good finish to the washed items. There is also the desire to reduce the amount of surfactants without negatively impacting sudsing nor grease cleaning and emulsification profile. Thus, there is the need to find new compositions that improve cleaning and suds longevity in hand washing conditions.

It has been found that some types of soil, in particular greasy soils comprising unsaturated fatty acids, act as a suds suppressor, triggering consumers to replace the product more frequently than is necessary. As such there is a need to provide liquid detergent compositions with desirable suds properties, especially in the presence of greasy soils, even more in the presence of greasy soils comprising unsaturated fatty acids, and that at the same time provide good soil and grease removal. The Applicant discovered that some or all of the above-mentioned needs can be at least partially fulfilled through the improved liquid detergent composition as described herein below.

SUMMARY OF THE INVENTION

The present invention meets one or more of these needs based on the surprising discovery that by formulating a liquid detergent composition comprising one or more hydroperoxy fatty acid producing enzymes capable of converting one or more fatty acids into one or more hydroperoxy fatty acids, a surfactant system, and a liquid carrier, such a composition exhibits good sudsing profile, particularly desirable suds volume and/or sustained suds stabilization, especially in the presence of greasy soils. It also provides good grease cleaning and emulsification benefits.

According to one aspect of the present invention there is provided a liquid detergent composition comprising one or more hydroperoxy fatty acid producing enzymes, a surfactant system, and from 30 wt % to 95 wt % by weight of the composition of a liquid carrier (i.e., water). The hydroperoxy fatty acid producing enzymes are selected from the group consisting of: arachidonate lipoxygenases, alpha-dioxygenases, and mixtures thereof, preferably alpha-dioxygenases. The surfactant system comprises one or more anionic surfactants and one or more co-surfactants selected from the group consisting of amphoteric surfactant, zwitterionic surfactant, and mixtures thereof, wherein the weight ratio of the anionic surfactants to the co-surfactants is less than 9:1, preferably from 5:1 to 1:1, more preferably from 4:1 to 2:1.

Preferably the liquid detergent composition is a manual-washing composition. Preferably the liquid detergent composition is for manual dishwashing. The composition of the invention provides good cleaning and good suds profile, especially in the presence of greasy soils.

According to another aspect, the present invention is directed to a method of manually washing soiled articles, preferably dishware, comprising the step of: delivering a composition of the invention into a volume of water to form a wash solution and immersing the soiled articles in the wash solution. Preferably the hydroperoxy fatty acid producing enzymes are present at a concentration of from 0.005 ppm to 15 ppm, preferably from 0.01 ppm to 5 ppm, more preferably from 0.02 ppm to 0.5 ppm, based on active protein, in the wash solution during the washing process. Preferably the manual washing is dishwashing and the soiled articles comprise soiled dishware. As used herein, "dishware" includes cookware and tableware.

When the composition of the invention is used according to this method a good sudsing profile, with a long lasting effect is achieved.

In yet another aspect, the present invention is directed to a method of manually washing dishware comprising the steps of: i) delivering a composition of the invention onto the dishware or a cleaning implement; ii) cleaning the dishware with the composition in the presence in water; and iii) optionally, rinsing the dishware. Preferably, the composition of the present invention is used in neat form (i.e., direct application) since greater benefits in terms of grease cleaning are obtained when the composition is directly applied on the soiled surface or on a cleaning implement, such as a sponge, to be used to clean the soiled surface.

According to another aspect, the present invention is directed to the use of one or more hydroperoxy fatty acid producing enzymes in a liquid detergent composition of the present invention to provide increased suds longevity in an aqueous wash liquor comprising soil, especially greasy soil, especially greasy soil comprising unsaturated fatty acids. The composition of the invention provides good cleaning and good suds profile, especially in the presence of greasy soils.

The elements of the composition of the invention described in relation to the first aspect of the invention apply mutatis mutandis to the other aspects of the invention.

These and other features, aspects and advantages of the present invention will become evident to those skilled in the art from the detailed description which follows.

DETAILED DESCRIPTION OF THE INVENTION

Definitions

As used herein, the articles "a" and "an" when used in a claim, are understood to mean one or more of what is claimed or described.

As used herein, the term "substantially free of" or "substantially free from" means that the indicated material is present in an amount of no more than about 5 wt %, preferably no more than about 2%, and more preferably no more than about 1 wt % by weight of the composition.

As used therein, the term "essentially free of" or "essentially free from" means that the indicated material is present in an amount of no more than about 0.1 wt % by weight of the composition, or preferably not present at an analytically detectable level in such composition. It may include compositions in which the indicated material is present only as an impurity of one or more of the materials deliberately added to such compositions.

As used herein, the term "detergent composition" refers to a composition or formulation designed for cleaning soiled surfaces. Such compositions include but are not limited to, dishwashing compositions, laundry detergent compositions, fabric softening compositions, fabric enhancing compositions, fabric freshening compositions, laundry pre-wash, laundry pretreat, laundry additives, spray products, dry cleaning agent or composition, laundry rinse additive, wash additive, post-rinse fabric treatment, ironing aid, hard surface cleaning compositions, unit dose formulation, delayed delivery formulation, detergent contained on or in a porous substrate or nonwoven sheet, and other suitable forms that may be apparent to one skilled in the art in view of the teachings herein. Such compositions may be used as a pre-cleaning treatment, a post-cleaning treatment, or may be added during the rinse or wash cycle of the cleaning process. The detergent compositions are in liquid form. Preferably the composition is for manual-washing. Preferably, the detergent composition of the present invention is a manual dishwashing detergent.

As used herein the term "fragment" means an amino acid sequence of at least 30, 60, 100, 150 contiguous amino acids of the reference sequences or any integer there between.

As used herein the term "identity" means the identity between two or more sequences and is expressed in terms of the identity or similarity between the sequences. Sequence identity can be measured in terms of percentage identity; the higher the percentage, the more identical the sequences are. The percentage identity is calculated over the length of comparison. For example, the identity is typically calculated over the entire length of a sequence aligned against the entire length of the reference sequence. Methods of alignment of sequences for comparison are well known in the art and identity can be calculated by many known methods. Various programs and alignment algorithms are described in the art.

It should be noted that the terms 'sequence identity' and 'sequence similarity' can be used interchangeably.

As used herein the term "increased suds longevity" means an increase in the duration of visible suds in a washing process cleaning soiled articles using the composition comprising one or more hydroperoxy fatty acid producing enzymes, and preferably one or more hydroperoxy fatty acid converting enzymes, compared with the suds longevity provided by the same composition and process in the absence of the hydroperoxy fatty acid producing enzymes and the hydroperoxy fatty acid converting enzymes.

As used herein, the term "soiled surfaces" refers non-specifically to any type of flexible material consisting of a network of natural or artificial fibers, including natural, artificial, and synthetic fibers, such as, but not limited to, cotton, linen, wool, polyester, nylon, silk, acrylic, and the like, as well as various blends and combinations. Soiled surfaces may further refer to any type of hard surface, including natural, artificial, or synthetic surfaces, such as, but not limited to, tile, granite, grout, glass, composite, vinyl, hardwood, metal, cooking surfaces, plastic, and the like, as well as blends and combinations, as well as dishware. Key targeted soiled surfaces by this application are soiled dishware.

As used herein, the term "variant" of hydroperoxy fatty acid producing enzyme or hydroperoxy fatty acid converting enzyme means an amino acid sequence when the hydroperoxy fatty acid producing enzyme or hydroperoxy fatty acid converting enzyme is modified by, or at, one or more amino acids (for example 1, 2, 3, 4, 5, 6, 7, 8, 9 or 10 or more amino acid modifications) selected from substitutions, insertions, deletions and combinations thereof. The variant may have "conservative" substitutions, wherein a substituted amino acid has similar structural or chemical properties to the amino acid that replaces it, for example, replacement of leucine with isoleucine. A variant may have "non-conservative" changes, for example, replacement of a glycine with a tryptophan. Variants may also include sequences with amino acid deletions or insertions, or both. Guidance in determining which amino acid residues may be substituted, inserted, or deleted without abolishing the activity of the protein may be found using computer programs well known in the art. Variants may also include truncated forms derived from a wild-type hydroperoxy fatty acid producing enzyme or hydroperoxy fatty acid converting enzyme, such as for example, a protein with a truncated N-terminus. Variants may also include forms derived by adding an extra amino acid sequence to a wild-type protein, such as for example, an N-terminal tag, a C-terminal tag or an insertion in the middle of the protein sequence.

As used herein, the term "water hardness" or "hardness" means uncomplexed cation ions (i.e., $Ca^{2+}$ or $Mg^{2+}$) present in water that have the potential to precipitate with anionic surfactants or any other anionically charged detergent actives under alkaline conditions, and thereby diminishing the surfactancy and cleaning capacity of surfactants. Further, the terms "high water hardness" and "elevated water hardness" can be used interchangeably and are relative terms for the purposes of the present invention, and are intended to include, but not limited to, a hardness level containing at least 12 grams of calcium ion per gallon water (gpg, "American grain hardness" units).

Detergent Composition

The present invention is directed to a liquid detergent composition, preferably a liquid manual dishwashing composition. It contains from 30% to 95%, preferably from 40% to 90%, more preferably from 50% to 85%, by weight of the composition of a liquid carrier in which the other essential and optional components are dissolved, dispersed or suspended. The liquid carrier is water.

Preferably the pH of the liquid detergent composition of the invention, measured as a 10% product concentration in demineralized water at 20° C., is adjusted to between 3 and 14, more preferably between 4 and 13, more preferably between 6 and 12 and most preferably between 8 and 10. The pH of the liquid detergent composition can be adjusted using pH modifying ingredients known in the art.

Enzymes

Fatty acids can be oxidized in the presence of molecular oxygen (02) by dioxygenases, such as arachidonate lipoxygenases and alpha-dioxygenases, to produce hydroperoxy fatty acids. These hydroperoxylated compounds can be further processed by other enzymes or spontaneously transform to a diverse group of oxygenated fatty acids and other derivatives. In the context of the current application, a "hydroperoxy fatty acid producing enzyme" is an enzyme that is capable of converting at least one fatty acid into a mixture of oxygenated compounds, comprising at least a hydroperoxy fatty acid as an intermediate or as a final product.

Unexpectedly, the Applicants found that a group of hydroperoxy fatty acid producing enzymes are capable of producing a more stable hence longer lasting sudsing profile in detergent wash solutions comprising oily and/or greasy soils. Not wishing to be bound by theory, the Applicants believe that the increased sudsing benefits are due to the conversion of fatty acids, present in the oily and/or greasy soils, into oxygenated fatty acids with enhanced surfactant properties and/or decreased tendency to precipitation in the presence of hard water.

Accordingly, the liquid detergent composition of the invention comprises one or more hydroperoxy fatty acid producing enzymes. The hydroperoxy fatty acid producing enzymes are capable of converting one or more fatty acids into one or more hydroperoxy fatty acids. The hydroperoxy fatty acid producing enzymes are selected from the group consisting of: arachidonate lipoxygenases, alpha-dioxygenases, and mixtures thereof, preferably alpha-dioxygenases.

Preferably the fatty acids being converted by the hydroperoxy fatty acid producing enzymes are selected from the group consisting of: mono unsaturated fatty acids, di unsaturated fatty acids, tri unsaturated fatty acids, tetra unsaturated fatty acids, penta unsaturated fatty acids, hexa unsaturated fatty acids, saturated fatty acids, and mixtures thereof; preferably myristoleic acid, myristic acid, pentadecanoic acid, palmitoleic acid, palmitic acid, sapienic acid, margaric acid, oleic acid, elaidic acid, vaccenic acid, linoleic acid, linoelaidic acid, α-linolenic acid, γ-linolenic acid, stearic acid, gadoleic acid, arachidic acid, behenic acid, α-eleostearic acid, β-eleostearic acid, ricinoleic acid, eicosenic acid, arachidonic acid, eicosapentaenoic acid, erucic acid, docosadienoic acid, docosahexaenoic acid, tetracosenoic acid, and mixtures thereof, preferably palmitoleic acid, oleic acid, linoleic acid, α-linolenic acid, γ-linolenic acid, and mixtures thereof, more preferably oleic acid.

Preferably the resultant hydroperoxy fatty acids formed from the conversion reaction of the fatty acids with the hydroperoxy fatty acid producing enzymes are selected from the group consisting of 2-hydroperoxy fatty acids, 8R-hydroperoxy fatty acids, 8S-hydroperoxy fatty acids, 9R-hydroperoxy fatty acids, 9S-hydroperoxy fatty acids, 10R-hydroperoxy fatty acids, 11R-hydroperoxy fatty acids, 11S-hydroperoxy fatty acids, 12R-hydroperoxy fatty acids, 12S-hydroperoxy fatty acids, 13R-hydroperoxy fatty acids, 13S-hydroperoxy fatty acids, 14R-hydroperoxy fatty acids, 14S-hydroperoxy fatty acids, 15S-hydroperoxy fatty acids, their derivatives, and mixtures thereof; preferably 2R-hydroperoxy fatty acids, unsaturated 5S-hydroperoxy fatty acids, unsaturated 8R-hydroperoxy fatty acids, unsaturated 9R-hydroperoxy fatty acids, unsaturated 11R-hydroperoxy fatty acids, unsaturated 12R-hydroperoxy fatty acids, unsaturated 12S-hydroperoxy fatty acids, unsaturated 13S-hydroperoxy fatty acids, unsaturated 15S-hydroperoxy fatty acids, their derivatives, and mixtures thereof; more preferably 2R-hydroperoxy fatty acids. The resulting hydroperoxy fatty acids can undergo spontaneous or enzymatic transformations to hydroxy fatty acids, aldehydes, shorter fatty acids, or other derivatives. Non-limiting examples of hydroxy fatty acids are 2-hydroxy fatty acids, unsaturated 5-hydroxy fatty acids, unsaturated 8-hydroxy fatty acids, unsaturated 9-hydroxy fatty acids, unsaturated 11-hydroxy fatty acids, unsaturated 12-hydroxy fatty acids, unsaturated 13-hydroxy fatty acids, unsaturated 15-hydroxy fatty acids, their derivatives, and mixtures thereof. Non-limiting examples of aldehydes are 1-alkanals, alken-1-als, alkadien-1-als, alkatrien-1-als, alkatetraen-1als, and mixtures thereof.

Lipoxygenases (EC 1.13.11.-) are a family of (non-heme), iron-containing dioxygenases that catalyze the insertion of molecular oxygen into unsaturated fatty acids to produce the corresponding hydroperoxy fatty acids. The present invention comprises arachidonate lipoxygenases. Even though arachidonate lipoxygenases typically recognize arachidonic acid/arachidonate as the preferred substrates, the term "arachidonate lipoxygenases" does not suggest any substrate specificity, i.e., the respective enzymes may act on any of the substrates (e.g. linoleic acid/linoleate, linolenic acid/linolenate, arachidonic acid/arachidonate). Preferably, the arachidonate lipoxygenases are selected from the group consisting of arachidonate 5-lipoxygenases (EC 1.13.11.34), arachidonate 8-lipoxygenases (EC 1.13.11.40), arachidonate 12-lipoxygenases (E.C. 1.13.11.31), and arachidonate 15-lipoxygenase (EC 1.13.11.33), preferably arachidonate 5-lipoxygenases (EC 1.13.11.34).

Non-limiting examples of arachidonate lipoxygenases that are part of the current invention include the wild-types listed in Table 1 and variants thereof which exhibit arachidonate lipoxygenase activity. Preferably the arachidonate lipoxygenases have at least 60%, preferably at least 70%, preferably at least 80%, preferably at least 85%, preferably at least 90%, preferably at least 95%, preferably at least 98% or preferably even 100% identity as calculated over the entire length of a sequence aligned against the entire length of at least one reference sequence selected from the group consisting of wild-type arachidonate lipoxygenases listed in Table 1.

TABLE 1

| Arachidonate lipoxygenases | |
|---|---|
| Origin | SEQ ID |
| Arachidonate 5-lipoxygenases | |
| Homo sapiens | 7 |
| Arachidonate 8-lipoxygenases | |
| Plexaura homomalla | 8 |
| Arachidonate 12-lipoxygenases | |
| Homo sapiens | 9 |
| Homo sapiens | 10 |

TABLE 1-continued

Arachidonate lipoxygenases

| Origin | SEQ ID |
|---|---|
| Homo sapiens | 11 |
| Physcomitrella patens | 12 |
| Arachidonate 15-lipoxygenases | |
| Homo sapiens | 13 |
| Pseudomonas aeruginosa | 14 |
| Cyanothece sp. | 15 |
| Nostoc punctiforme | 16 |
| Hordeum vulgare | 17 |

Regiospecific lipoxygenases catalyze the positional-specific hydroperoxylation of unsaturated fatty acids. For example, arachidonate 12- and 15-lipoxygenases convert arachidonic acid into the corresponding 12- and 15-hydroperoxy fatty acids; whereas some variants of the same enzymes (e.g. SEQ ID NO: 11, 12, 15, 16, and 17) can convert linoleic acid into 9-, 11-, or 13-hydroperoxy derivatives. Furthermore, some lipoxygenases are able to catalyze the incorporation of molecular oxygen at several positions of the unsaturated fatty acid (e.g. SEQ ID NO: 11).

Alpha-dioxygenases convert saturated and unsaturated fatty acids to their corresponding 2-hydroperoxy fatty acids via stereoselective dioxygenation. The resulting hydroperoxy fatty acids can undergo spontaneous decarboxylation to shorter aldehydes. Alpha-dioxygenases differs from lipoxygenases in that an unsaturated carbon bond is not required during the oxidation. They are generally encoded by different species of plants and fungi, where they are up-regulated during the host defense response against pathogen attack, but homologs are also found in bacteria.

Non-limiting examples of alpha-dioxygenases that are part of the current invention include the wild-types listed in Table 2 and variants thereof which exhibit alpha-dioxygenase activity. Preferred alpha-dioxygenases exhibit at least 20%, preferably at least 30%, preferably at least 40%, preferably at least 50%, preferably at least 60%, preferably at least 70%, preferably at least 80%, preferably at least 90%, preferably at least 95%, preferably at least 98% or preferably even 100% identity as calculated over the entire length of a sequence aligned against the entire length of at least one reference sequence selected from the group consisting of wild-type alpha-dioxygenases listed in Table 2.

TABLE 2

Alpha-Dioxygenases

| Origin | SEQ ID |
|---|---|
| Alpha-dioxygenases | |
| Arabidopsis thaliana | 1 |
| Arabidopsis thaliana | 2 |
| Fusarium graminearum | 3 |
| Fusarium verticillioides | 4 |
| Fusarium oxysporum | 5 |
| Oryza sativa (Rice) | 6 |

Preferably the hydroperoxy fatty acid producing enzymes are present in an amount of from 0.0001 wt % to 1 wt %, by weight of the composition, based on active protein in the composition. More preferably the hydroperoxy fatty acid producing enzymes are present in the amounts of from 0.001 wt % to 0.2 wt %, by weight of the composition, based on active protein in the composition.

The present invention also includes variants of enzymes. Variants of enzymes, as used herein, include a sequence resulting when a wild-type protein of the respective protein is modified by, or at, one or more amino acids (for example 1, 2, 5 or 10 amino acids). The invention also includes variants in the form of truncated forms derived from a wild-type enzyme, such as a protein with a truncated N-terminus or a truncated C-terminus. Some enzymes may include an N-terminal signal peptide that is likely removed upon secretion by the cell. The present invention includes variants without the N-terminal signal peptide. Bioinformatic tools, such as SignalP ver 4.1 (Petersen T N., Brunak S., von Heijne G. and Nielsen H. (2011), Nature Methods, 8:785-786), can be used to predict the existence and length of such signal peptides. The invention also includes variants derived by adding an extra amino acid sequence to a wild-type protein, such as for example, an N-terminal tag, a C-terminal tag or an insertion in the middle of the protein sequence. Non-limiting examples of tags are maltose binding protein (MBP) tag, glutathione S-transferase (GST) tag, thioredoxin (Trx) tag, His-tag, and any other tags known by those skilled in art. Tags can be used to improve solubility and expression levels during fermentation or as a handle for enzyme purification.

It is important that variants of enzymes retain and preferably improve the ability of the wild-type protein to catalyze the conversion of the unsaturated fatty acids. Some performance drop in a given property of variants may of course be tolerated, but the variants should retain and preferably improve suitable properties for the relevant application for which they are intended. Screening of variants of one of the wild-types can be used to identify whether they retain and preferably improve appropriate properties.

The variants may have "conservative" substitutions. Suitable examples of conservative substitution includes one conservative substitution in the enzyme, such as a conservative substitution in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17. Other suitable examples include 10 or fewer conservative substitutions in the protein, such as five or fewer. An enzyme of the invention may therefore include 1, 2, 3, 4, 5, 6, 7, 8, 9, 10 or more conservative substitutions. An enzyme can be produced to contain one or more conservative substitutions by manipulating the nucleotide sequence that encodes that enzyme using, for example, standard procedures such as site-directed mutagenesis or PCR.

Examples of amino acids which may be substituted for an original amino acid in an enzyme and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

A variant includes a "modified enzyme" or a "mutant enzyme" which encompasses proteins having at least one substitution, insertion, and/or deletion of an amino acid. A modified enzyme may have 1, 2, 3, 4, 5, 6, 7, 8, 9 or 10 or more amino acid modifications (selected from substitutions, insertions, deletions and combinations thereof).

Enzymes can be modified by a variety of chemical techniques to produce derivatives having essentially the same or preferably improved activity as the unmodified enzymes, and optionally having other desirable properties.

For example, carboxylic acid groups of the protein, whether carboxyl-terminal or side chain, may be provided in the form of a salt of a pharmaceutically-acceptable cation or esterified, for example to form a C1-C6 alkyl ester, or converted to an amide, for example of formula CONR1R2 wherein R1 and R2 are each independently H or C1-C6 alkyl, or combined to form a heterocyclic ring, such as a 5- or 6-membered ring. Amino groups of the enzyme, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C20 alkyl or dialkyl amino or further converted to an amide. Hydroxyl groups of the protein side chains may be converted to alkoxy or ester groups, for example C1-C20 alkoxy or C1-C20 alkyl ester, using well-recognized techniques. Phenyl and phenolic rings of the protein side chains may be substituted with one or more halogen atoms, such as F, CI, Br or I, or with C1-C20 alkyl, C1-C20 alkoxy, carboxylic acids and esters thereof, or amides of such carboxylic acids. Methylene groups of the protein side chains can be extended to homologous C2-C4 alkylenes. Thiols can be protected with any one of a number of well-recognized protecting groups, such as acetamide groups. Those skilled in the art will also recognize methods for introducing cyclic structures into the proteins of this disclosure to select and provide conformational constraints to the structure that result in enhanced stability.

Identity, or homology, percentages as mentioned herein in respect of the present invention are those that can be calculated with the GAP program, obtainable from GCG (Genetics Computer Group Inc., Madison, Wis, USA). Alternatively, a manual alignment can be performed.

For enzyme sequence comparison the following settings can be used: Alignment algorithm: Needleman and Wunsch, J. Mol. Biol. 1970, 48: 443-453. As a comparison matrix for amino acid similarity the Blosum62 matrix is used (Henikoff S. and Henikoff J. G., P.N.A.S. USA 1992, 89: 10915-10919). The following gap scoring parameters are used: Gap penalty: 12, gap length penalty: 2, no penalty for end gaps.

A given sequence is typically compared against the full-length sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17 to obtain a score.

The hydroperoxy fatty acid producing enzymes may be incorporated into the liquid detergent composition via an additive particle, such as an enzyme granule or in the form of an encapsulate, or may be added in the form of a liquid formulation. Preferably the enzyme is incorporated into the liquid detergent composition via an encapsulate. Encapsulating the enzymes promote the stability of the enzymes in the composition and helps to counteract the effect of any hostile compounds present in the composition, such as bleach, protease, surfactant, chelant, etc.

The hydroperoxy fatty acid producing enzymes are present in an additive particle may be the only enzymes in the additive particle or may be present in the additive particle in combination with one or more additional co-enzymes.

Preferably the composition of the invention may further comprise one or more co-enzymes selected from the group consisting of: fatty-acid peroxidases (EC 1.11.1.3), unspecific peroxygenases (EC 1.11.2.1), plant seed peroxygenases (EC 1.11.2.3), fatty acid peroxygenases (EC 1.11.2.4), linoleate diol synthases (EC 1.13.11.44), 5,8-linoleate diol synthases (EC 1.13.11.60 and EC 5.4.4.5), 7,8-linoleate diol synthases (EC 1.13.11.60 and EC 5.4.4.6), 9,14-linoleate diol synthases (EC 1.13.11.B1), 8,11-linoleate diol synthases, oleate diol synthases, other linoleate diol synthases, unspecific monooxygenase (EC 1.14.14.1), alkane 1-monooxygenase (EC 1.14.15.3), oleate 12-hydroxylases (EC 1.14.18.4), fatty acid amide hydrolase (EC 3.5.1.99), oleate hydratases (EC 4.2.1.53), linoleate isomerases (EC 5.2.1.5), linoleate (10E,12Z)-isomerases (EC 5.3.3.B2), fatty acid decarboxylases (OleT-like), iron-dependent decarboxylases (UndA-like), other CYP450 monooxygenases, amylases, lipases, proteases, cellulases, and mixtures thereof. Preferably the co-enzymes are fatty-acid peroxidases (EC 1.11.1.3), unspecific peroxygenases (EC 1.11.2.1), plant seed peroxygenases (EC 1.11.2.3), fatty acid peroxygenases (EC 1.11.2.4), and mixtures thereof.

Other suitable additional co-enzymes include protease such as metalloprotease or alkaline serine protease, such as subtilisin, mannanase, pectinase, DNAse, oxidoreductase, peroxidases, lipases, phospholipases, cellobiohydrolases, cellobiose dehydrogenases, esterases, cutinases, pectinases, pectate lyases, keratinases, reductases, oxidases, phenoloxidases, ligninases, pullulanases, tannases, pentosanases, glucanases, arabinosidases, hyaluronidase, chondroitinase, laccases, amylases, and mixtures thereof.

Where necessary, the composition comprises, provides access to or forms in situ any additional substrate necessary for the effective functioning of the enzyme. For example, molecular oxygen is provided as an additional substrate for alpha-dioxygenases, and arachidonate lipoxygenases; water for oleate hydratases; and hydrogen peroxide can be provided for peroxidases, peroxygenases, and/or fatty acid decarboxylases (OleT-like). The oxygen required by the alpha-dioxygenases and the arachidonate lipoxygenases can be obtained from the atmosphere or from a precursor that can be transformed to produce oxygen in situ. In many applications, oxygen from the atmosphere can be present in sufficient amounts.

Surfactant System

Preferably the liquid detergent composition comprises from 1 wt % to 60 wt %, preferably from 5 wt % to 50 wt %, more preferably from 8 wt % to 40 wt %, by weight of the total composition of a surfactant system.

The surfactant system of the composition of the present invention comprises one or more anionic surfactants. Preferably, the surfactant system for the liquid detergent composition of the present invention comprises from 1 wt % to 40 wt %, preferably 6 wt % to 35 wt %, more preferably 8 wt % to 30 wt % by weight of the total composition of the anionic surfactants. The anionic surfactants can be any anionic cleaning surfactants, preferably selected from sulfate and/or sulfonate anionic surfactants. HLAS (linear alkylbenzene sulfonates) would be the most preferred sulfonate anionic surfactants. Especially preferred anionic surfactants are selected from the group consisting of alkyl sulfates, alkyl alkoxy sufates preferably alkyl ethoxy sulfates, alkyl benzene sulfonates, paraffin sulfonates, and mixtures thereof. Preferred anionic surfactants are a combination of alkyl sulfates and alkyl ethoxy sulfates with a combined average ethoxylation degree of less than 5, preferably less than 3, more preferably less than 2 and more than 0.5 and an average level of branching of from about 5% to about 40%, more preferably from about 10% to 35%, and even more preferably from about 20% to 30%.

The average alkoxylation degree is the mol average alkoxylation degree of all the components of the mixture (i.e., mol average alkoxylation degree) of the anionic surfactant. In the mol average alkoxylation degree calculation the weight of sulfate anionic surfactant components not having alkoxylate groups should also be included.

Mol average alkoxylation degree=$(x1*$alkoxylation degree of surfactant $1+x2*$alkoxylation degree of surfactant $2+ \ldots )/(x1+x2+ \ldots )$ wherein x1, x2, . . . are the number of moles of each sulfate anionic surfactant of the mixture and alkoxylation degree is the number of alkoxy groups in each sulfate anionic surfactant.

The average level of branching is the weight average % of branching and it is defined according to the following formula:

Weight average of branching (%)=$[(x1*$wt % branched alcohol 1 in alcohol $1+x2*$wt % branched alcohol 2 in alcohol $2+ \ldots )/(x1+x2+ \ldots )]*100$ wherein x1, x2, . . . are the weight in grams of each alcohol in the total alcohol mixture of the alcohols which were used as starting material for the anionic surfactant for the composition of the invention. In the weight average branching degree calculation the weight of anionic surfactant components not having branched groups should also be included.

Suitable examples of commercially available sulfates include, those based on Neodol alcohols ex the Shell company, Lial—Isalchem and Safol ex the Sasol company, natural alcohols ex The Procter & Gamble Chemicals company. Suitable sulfonate surfactants for use herein include water-soluble salts of C8-C18 alkyl or hydroxyalkyl sulfonates; C11-C18 alkyl benzene sulfonates (LAS), modified alkylbenzene sulfonate (MLAS); methyl ester sulfonate (MES); and alpha-olefin sulfonate (AOS). Those also include the paraffin sulfonates may be monosulfonates and/ or disulfonates, obtained by sulfonating paraffins of 10 to 20 carbon atoms. The sulfonate surfactant also include the alkyl glyceryl sulfonate surfactants.

The surfactant system of the composition of the present invention further comprises a primary co-surfactant system, wherein the primary co-surfactant system is preferably selected from the group consisting of amphoteric surfactant, zwitterionic surfactant and mixtures thereof. Preferably the amphoteric surfactant is amine oxide surfactant and the zwitterionic surfactant is betaine surfactant. Preferably, the surfactant system for the liquid detergent composition of the present invention comprises from 0.5 wt % to 15 wt %, preferably from 1 wt % to 12 wt %, more preferably from 2 wt % to 10 wt %, by weight of the total composition of a primary co-surfactant system.

Preferably the weight ratio of the anionic surfactants to the primary co-surfactants is less than 9:1, more preferably from 5:1 to 1:1, more preferably from 4:1 to 2:1. Preferably the primary co-surfactant system is an amphoteric surfactant. Preferably, the primary co-surfactant system is an amine oxide surfactant preferably alkyl dimethyl amine oxides, wherein the anionic surfactants are a mixture of alkyl sulfates and alkyl alkoxy sulfates, and wherein the composition comprises the anionic surfactants and the amine oxide surfactant in a weight ratio of less than 9:1, more preferably from 5:1 to 1:1, more preferably from 4:1 to 2:1, preferably from 3:1 to 2.5:1. Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or branched alkyl moiety.

Optionally the amine oxide surfactant is a mixture of amine oxides comprising a low-cut amine oxide and a mid-cut amine oxide. The amine oxide of the composition of the invention then comprises:
a) from about 10% to about 45% by weight of the amine oxide of low-cut amine oxide of formula R1R2R3AO wherein R1 and R2 are independently selected from hydrogen, C1-C4 alkyls or mixtures thereof, and R3 is selected from C10 alkyls or mixtures thereof; and
b) from 55% to 90% by weight of the amine oxide of mid-cut amine oxide of formula R4R5R6AO wherein R4 and R5 are independently selected from hydrogen, C1-C4 alkyls or mixtures thereof, and R6 is selected from C12-C16 alkyls or mixtures thereof.

In a preferred low-cut amine oxide for use herein R3 is n-decyl. In another preferred low-cut amine oxide for use herein R1 and R2 are both methyl. In an especially preferred low-cut amine oxide for use herein R1 and R2 are both methyl and R3 is n-decyl.

Preferably, the amine oxide comprises less than about 5%, more preferably less than 3%, by weight of the amine oxide of an amine oxide of formula R7R8R9AO wherein R7 and R8 are selected from hydrogen, C1-C4 alkyls and mixtures thereof and wherein R9 is selected from C8 alkyls and mixtures thereof. Compositions comprising R7R8R9AO tend to be unstable and do not provide very suds mileage.

Preferably the primary co-surfactant system is a zwitterionic surfactant. Suitable examples of zwitterionic surfactants include betaines, such as alkyl betaines, alkylamidobetaine, amidazoliniumbetaine, sulfobetaine (INCI Sultaines) as well as the Phosphobetaine and preferably meets formula (I):

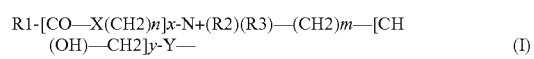

wherein:
R1 is a saturated or unsaturated C6-22 alkyl residue, preferably C8-18 alkyl residue, in particular a saturated C10-16 alkyl residue, for example a saturated C12-14 alkyl residue;
X is NH, NR4 with C1-4 Alkyl residue R4, 0 or S;
n is a number from 1 to 10, preferably 2 to 5, in particular 3;
x is 0 or 1, preferably 1;
R2 and R3 are independently a C1-4 alkyl residue, potentially hydroxy substituted such as a hydroxyethyl, preferably a methyl;
m is a number from 1 to 4, in particular 1, 2 or 3;
y is 0 or 1; and
Y is COO, SO3, OPO(OR5)O or P(O)(OR5)O, whereby R5 is a hydrogen atom H or a C1-4 alkyl residue.

Preferred betaines are the alkyl betaines of the formula (Ia), the alkyl amido propyl betaine of the formula (Ib), the Sulfo betaines of the formula (Ic), and the Amido sulfobetaine of the formula (Id);

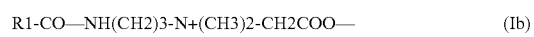

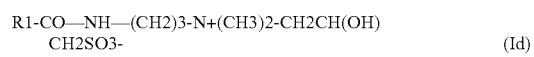

in which R1 has the same meaning as in formula (I). Particularly preferred betaines are the Carbobetaine [wherein Y——COO—], in particular the Carbobetaine of the formula (Ia) and (Ib), more preferred are the Alkylamidobetaine of the formula (Ib). A preferred betaine is, for example, cocoamidopropylbetaine.

Preferably, the surfactant system of the composition of the present invention further comprises from 0.1 wt % to 10 wt % by weight of the total composition of a secondary co-surfactant system preferably comprising a non-ionic surfactant. Suitable non-ionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol. Highly preferred non-ionic surfactants are the condensation products of guerbet alcohols with from 2 to 18 moles, preferably 2 to 15, more preferably 5-12 of ethylene oxide per mole of alcohol. Preferably, the non-ionic surfactants are an alkyl ethoxylated surfactants, preferably comprising from 9 to 15 carbon atoms in its alkyl chain and from 5 to 12 units of ethylene oxide per mole of alcohol. Other suitable non-ionic surfactants for use herein include fatty alcohol polyglycol ethers, alkylpolyglucosides and fatty acid glucamides, preferably alkylpolyglucosides. Preferably the alkyl polyglucoside surfactant is a C8-C16 alkyl polyglucoside surfactant, preferably a C8-C14 alkyl polyglucoside surfactant, preferably with an average degree of polymerization of between 0.1 and 3, more preferably between 0.5 and 2.5, even more preferably between 1 and 2. Most preferably the alkyl polyglucoside surfactant has an average alkyl carbon chain length between 10 and 16, preferably between 10 and 14, most preferably between 12 and 14, with an average degree of polymerization of between 0.5 and 2.5 preferably between 1 and 2, most preferably between 1.2 and 1.6. C8-C16 alkyl polyglucosides are commercially available from several suppliers (e.g., Simusol® surfactants from Seppic Corporation; and Glucopon® 600 CSUP, Glucopon® 650 EC, Glucopon® 600 CSUP/MB, and Glucopon® 650 EC/MB, from BASF Corporation). Preferably, the composition comprises the anionic surfactant and the non-ionic surfactant in a ratio of from 2:1 to 50:1, preferably 2:1 to 10:1.

Enzyme Stabilizer

Preferably the composition of the invention comprises an enzyme stabilizer, selected from the group consisting of chemical and physical stabilizers, preferably the physical stabilizer comprises encapsulated enzyme. Suitable enzyme stabilizers may be selected from the group consisting of (a) univalent, bivalent and/or trivalent cations preferably selected from the group of inorganic or organic salts of alkaline earth metals, alkali metals, aluminum, iron, copper and zinc, preferably alkali metals and alkaline earth metals, preferably alkali metal and alkaline earth metal salts with halides, sulfates, sulfites, carbonates, hydrogencarbonates, nitrates, nitrites, phosphates, formates, acetates, propionates, citrates, maleates, tartrates, succinates, oxalates, lactates, and mixtures thereof. In a preferred embodiment the salt is selected from the group consisting of sodium chloride, calcium chloride, potassium chloride, sodium sulfate, potassium sulfate, sodium acetate, potassium acetate, sodium formate, potassium formate, calcium lactate, calcium nitrate and mixtures thereof. Most preferred are salts selected from the group consisting of calcium chloride, potassium chloride, potassium sulfate, sodium acetate, potassium acetate, sodium formate, potassium formate, calcium lactate, calcium nitrate, and mixtures thereof, and in particular potassium salts selected from the group of potassium chloride, potassium sulfate, potassium acetate, potassium formate, potassium propionate, potassium lactate and mixtures thereof. Most preferred are potassium acetate and potassium chloride. Preferred calcium salts are calcium formate, calcium lactate and calcium nitrate including calcium nitrate tetrahydrate. Calcium and sodium formate salts may be preferred. These cations are present at least 0.01 wt %, preferably at least 0.03 wt %, more preferably at least 0.05 wt %, most preferably at least 0.25 wt % up to 2 wt % or even up to 1 wt % by weight of the total composition. These salts are formulated from 0.1 wt % to 5 wt %, preferably from 0.2 wt % to 4 wt %, more preferably from 0.3 wt % to 3 wt %, most preferably from 0.5 wt % to 2 wt % relative to the total weight of the composition. Further enzyme stabilizers can be selected from the group (b) carbohydrates selected from the group consisting of oligosaccharides, polysaccharides and mixtures thereof, such as a monosaccharide glycerate as described in WO201219844; (c) mass efficient reversible protease inhibitors selected from the group consisting of phenyl boronic acid and derivatives thereof, preferably 4-formyl phenylboronic acid; (d) alcohols such as 1,2-propane diol, propylene glycol; (e) peptide aldehyde stabilizers such as tripeptide aldehydes such as Cbz-Gly-Ala-Tyr-H, or disubstituted alaninamide; (f) carboxylic acids such as phenyl alkyl dicarboxylic acid as described in WO2012/19849 or multiply substituted benzyl carboxylic acid comprising a carboxyl group on at least two carbon atoms of the benzyl radical such as described in WO2012/19848, phthaloyl glutamine acid, phthaloyl asparagine acid, aminophthalic acid and/or an oligoaminobiphenyl-oligocarboxylic acid; and (g) mixtures thereof.

Additional Enzymes

Preferred compositions of the invention comprise one or more additional enzymes selected from the group consisting of amylases, lipases, proteases, cellulases, lipoxygenases, diol synthases, and mixtures thereof. Even more preferred compositions of the invention comprise one or more enzymes selected from lipases, proteases, cellulases, amylases and any combination thereof. Most preferably compositions of the invention comprise one or more enzymes selected from lipases, proteases, amylases and any combination thereof.

It may be particularly preferred for the compositions of the present invention to additionally comprise a protease enzyme. Since oleic acid and other foam suppressing unsaturated fatty acids are present in body soils or even human skin, as protease enzyme acts as a skin care agent, or breaks down proteinaceous soils, fatty acids released are broken down, preventing suds suppression.

It may be particularly preferred for the compositions of the present invention to additionally comprise an amylase enzyme. Since oily soils are commonly entrapped in starchy soils, the amylase and unsaturated fatty acid transforming enzymes work synergistically together: fatty acid soils are released by breakdown of starchy soils with amylase, thus, the unsaturated fatty acid transforming enzyme is particularly effective in ensuring there is no negative impact on suds in the wash liquor.

Each additional enzyme is typically present in an amount of from 0.0001 wt % to 1 wt % (by weight of active protein) more preferably from 0.0005 wt % to 0.5 wt %, most preferably 0.005 wt % to 0.1 wt %, by weight of the composition, based on active protein.

Salt

The composition of the present invention may optionally comprise from 0.01% to 3%, preferably from 0.05% to 2%, more preferably from 0.2% to 1.5%, or most preferably 0.5% to 1%, by weight of the total composition of a salt, preferably a monovalent, divalent inorganic salt or a mixture thereof, preferably sodium chloride. Most preferably the composition alternatively or further comprises a multivalent metal cation in the amount of from 0.01 wt % to 2 wt %, preferably from 0.1% to 1%, more preferably from 0.2% to 0.8% by weight of the composition, preferably the multivalent metal cation is magnesium, aluminum, copper, calcium or iron, more preferably magnesium, most preferably said multivalent salt is magnesium chloride. Without wishing to be bound by theory, it is believed that use of a multivalent cation helps with the formation of protein/protein, surfactant/surfactant or hybrid protein/surfactant network at the oil water and air water interface that is strengthening the suds.

Carbohydrates

Preferably the composition of the present invention comprises one or more carbohydrates selected from the group comprising 0-glycan, N-glycan, and mixtures thereof. Suitable carbohydrates include alpha or beta glucan with 1,3 and/or 1.4 and/or 1,6 linkage. Glucans can be modified especially with carboxyl sulfate, glycol ether of amino groups. Glucan can be extracted from dextran, starch or cellulose. Glucan with structure close to natural glucan such as schizophyllan, scleroglucan or paramylon are particularly preferred.

Hydrotrope

The composition of the present invention may optionally comprise from 1% to 10%, or preferably from 0.5% to 10%, more preferably from 1% to 6%, or most preferably from 0.1% to 3%, or combinations thereof, by weight of the total composition of a hydrotrope, preferably sodium cumene sulfonate. Other suitable hydrotropes for use herein include anionic-type hydrotropes, particularly sodium, potassium, and ammonium xylene sulfonate, sodium, potassium and ammonium toluene sulfonate, sodium potassium and ammonium cumene sulfonate, and mixtures thereof, as disclosed in U.S. Pat. No. 3,915,903. Preferably the composition of the present invention is isotropic. An isotropic composition is distinguished from oil-in-water emulsions and lamellar phase compositions. Polarized light microscopy can assess whether the composition is isotropic. See e.g., *The Aqueous Phase Behaviour of Surfactants*, Robert Laughlin, Academic Press, 1994, pp. 538-542. Preferably an isotropic composition is provided. Preferably the composition comprises 0.1% to 3% by weight of the total composition of a hydrotrope, preferably wherein the hydrotrope is selected from sodium, potassium, and ammonium xylene sulfonate, sodium, potassium and ammonium toluene sulfonate, sodium potassium and ammonium cumene sulfonate, and mixtures thereof.

Organic Solvent

The composition of the present invention may optionally comprise an organic solvent. Suitable organic solvents include C4-14 ethers and diethers, polyols, glycols, alkoxylated glycols, C6-C16 glycol ethers, alkoxylated aromatic alcohols, aromatic alcohols, aliphatic linear or branched alcohols, alkoxylated aliphatic linear or branched alcohols, alkoxylated C1-C5 alcohols, C8-C14 alkyl and cycloalkyl hydrocarbons and halohydrocarbons, and mixtures thereof. Preferably the organic solvents include alcohols, glycols, and glycol ethers, alternatively alcohols and glycols. The composition comprises from 0% to less than 50%, preferably from 0.01% to 25%, more preferably from 0.1% to 10%, or most preferably from 0.5% to 5%, by weight of the total composition of an organic solvent, preferably an alcohol, more preferably an ethanol, a polyalkyleneglycol, more preferably polypropyleneglycol, and mixtures thereof.

Amphiphilic Polymer

The composition of the present invention may further comprise from about 0.01% to about 5%, preferably from about 0.05% to about 2%, more preferably from about 0.07% to about 1% by weight of the total composition of an amphiphilic polymer selected from the groups consisting of amphiphilic alkoxylated polyalkyleneimine and mixtures thereof, preferably an amphiphilic alkoxylated polyalkyleneimine.

Preferably, the amphiphilic alkoxylated polyalkyleneimine is an alkoxylated polyethyleneimine polymer comprising a polyethyleneimine backbone having average molecular weight range from 100 to 5,000, preferably from 400 to 2,000, more preferably from 400 to 1,000 Daltons and the alkoxylated polyethyleneimine polymer further comprising:

(i) one or two alkoxylation modifications per nitrogen atom by a polyalkoxylene chain having an average of about 1 to about 50 alkoxy moieties per modification, wherein the terminal alkoxy moiety of the alkoxylation modification is capped with hydrogen, a C1-C4 alkyl or mixtures thereof;

(ii) an addition of one C1-C4 alkyl moiety and one or two alkoxylation modifications per nitrogen atom by a polyalkoxylene chain having an average of about 1 to about 50 alkoxy moieties per modification wherein the terminal alkoxy moiety is capped with hydrogen, a C1-C4 alkyl or mixtures thereof; or (iii) a combination thereof; and wherein the alkoxy moieties comprises ethoxy (EO) and/or propxy (PO) and/or butoxy (BO) and wherein when the alkoxylation modification comprises EO it also comprises PO or BO.

Preferred amphiphilic alkoxylated polyethyleneimine polymers comprise EO and PO groups within their alkoxylation chains, the PO groups preferably being in terminal position of the alkoxy chains, and the alkoxylation chains preferably being hydrogen capped. Hydrophilic alkoxylated polyethyleneimine polymers solely comprising ethoxy (EO) units within the alkoxylation chain could also optionally be formulated within the scope of this invention.

For example, but not limited to, below is shown possible modifications to terminal nitrogen atoms in the polyethyleneimine backbone where R represents an ethylene spacer and E represents a C1-C4 alkyl moiety and X— represents a suitable water soluble counterion.

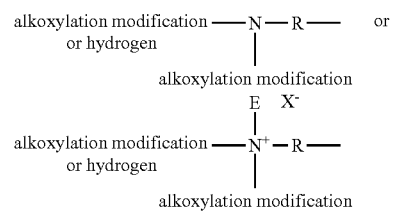

Also, for example, but not limited to, below is shown possible modifications to internal nitrogenatoms in the polyethyleneimine backbone where R represents an ethylene spacer and E represents a C1-C4 alkyl moiety and X— represents a suitable water soluble counterion.

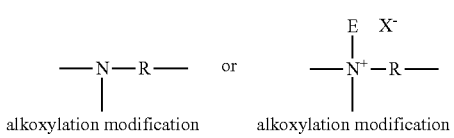

alkoxylation modification     alkoxylation modification

The alkoxylation modification of the polyethyleneimine backbone consists of the replacement of a hydrogen atom by a polyalkoxylene chain having an average of about 1 to about 50 alkoxy moieties, preferably from about 20 to about 45 alkoxy moieties, most preferably from about 30 to about 45 alkoxy moieties. The alkoxy moieties are selected from ethoxy (EO), propoxy (PO), butoxy (BO), and mixtures thereof. Alkoxy moieties solely comprising ethoxy units are outside the scope of the invention though. Preferably, the polyalkoxylene chain is selected from ethoxy/propoxy block moieties. More preferably, the polyalkoxylene chain is ethoxy/propoxy block moieties having an average degree of ethoxylation from about 3 to about 30 and an average degree of propoxylation from about 1 to about 20, more preferably ethoxy/propoxy block moieties having an average degree of ethoxylation from about 20 to about 30 and an average degree of propoxylation from about 10 to about 20.

More preferably the ethoxy/propoxy block moieties have a relative ethoxy to propoxy unit ratio between 3 to 1 and 1 to 1, preferably between 2 to 1 and 1 to 1. Most preferably the polyalkoxylene chain is the ethoxy/propoxy block moieties wherein the propoxy moiety block is the terminal alkoxy moiety block.

The modification may result in permanent quaternization of the polyethyleneimine backbone nitrogen atoms. The degree of permanent quaternization may be from 0% to about 30% of the polyethyleneimine backbone nitrogen atoms. It is preferred to have less than 30% of the polyethyleneimine backbone nitrogen atoms permanently quaternized. Most preferably the degree of quaternization is about 0%.

A preferred polyethyleneimine has the general structure of Formula (II):

wherein the polyethyleneimine backbone has a weight average molecular weight of about 600, n of formula (II) has an average of about 10, m of formula (II) has an average of about 7 and R of formula (II) is selected from hydrogen, a C1-C4 alkyl and mixtures thereof, preferably hydrogen. The degree of permanent quaternization of formula (II) may be from 0% to about 22% of the polyethyleneimine backbone nitrogen atoms. The molecular weight of this polyethyleneimine preferably is between 10,000 and 15,000.

An alternative polyethyleneimine has the general structure of Formula (II) but wherein the polyethyleneimine backbone has a weight average molecular weight of about 600, n of Formula (II) has an average of about 24, m of Formula (II) has an average of about 16 and R of Formula (II) is selected from hydrogen, a C1-C4 alkyl and mixtures thereof, preferably hydrogen. The degree of permanent quaternization of Formula (II) may be from 0% to about 22% of the polyethyleneimine backbone nitrogen atoms. The molecular weight of this polyethyleneimine preferably is between 25,000 and 30,000.

Most preferred polyethyleneimine has the general structure of Formula (II) wherein the polyethyleneimine backbone has a weight average molecular weight of about 600, n of Formula (II) has an average of about 24, m of Formula (II) has an average of about 16 and R of Formula (II) is hydrogen. The degree of permanent quaternization of Formula (II) is 0% of the polyethyleneimine backbone nitrogen atoms. The molecular weight of this polyethyleneimine preferably is about from about 25,000 to 30,000, most preferably about 28,000.

These polyethyleneimines can be prepared, for example, by polymerizing ethyleneimine in the presence of a catalyst such as carbon dioxide, sodium bisulfite, sulfuric acid, hydrogen peroxide, hydrochloric acid, acetic acid, and the like, as described in more detail in PCT Publication No. WO 2007/135645.

Chelant

The liquid detergent composition herein can comprise a chelant at a level of from 0.1% to 20%, preferably from 0.2% to 5%, more preferably from 0.2% to 3% by weight of total composition.

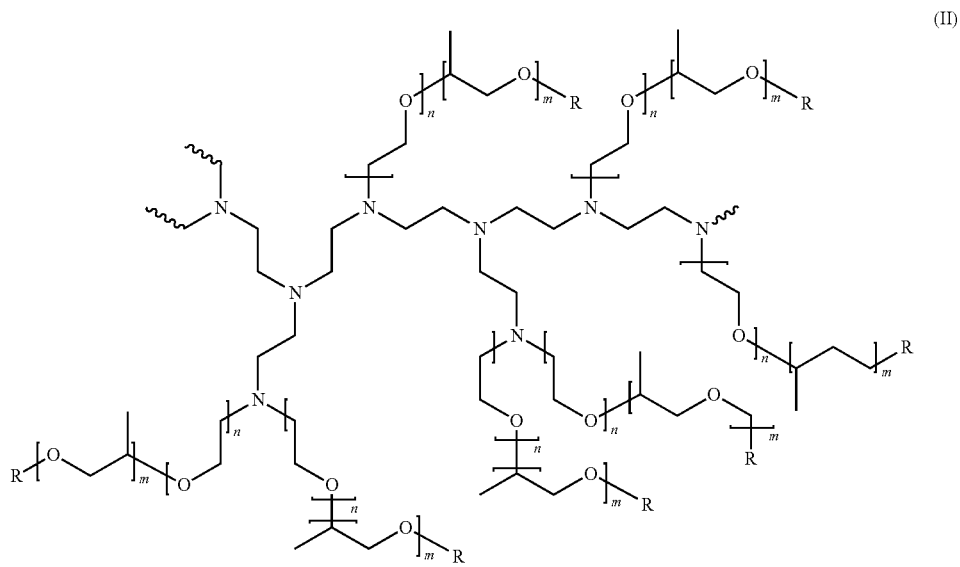

(II)

As commonly understood in the detergent field, chelation herein means the binding or complexation of a bi- or multidentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates or scale, or forming encrustations on soils turning them harder to be removed. The ligand forms a chelate complex with the substrate. The term is reserved for complexes in which the metal ion is bound to two or more atoms of the chelant.

Preferably, the composition of the present invention comprises one or more chelant, preferably selected from the group comprising carboxylate chelants, amino carboxylate chelants, amino phosphonate chelants, and mixtures thereof. Preferably the chelant is selected from the group consisting of MGDA (methylglycine-N,N-diacetic acid), GLDA (glutamic-N,N-diacetic acid), and mixtures thereof.

Suitable chelating agents can be selected from the group consisting of amino carboxylates, amino phosphonates, polycarboxylate chelating agents and mixtures thereof.

Other chelants include homopolymers and copolymers of polycarboxylic acids and their partially or completely neutralized salts, monomeric polycarboxylic acids and hydroxycarboxylic acids and their salts. Suitable polycarboxylic acids are acyclic, alicyclic, heterocyclic and aromatic carboxylic acids, in which case they contain at least two carboxyl groups which are in each case separated from one another by, preferably, no more than two carbon atoms. A suitable hydroxycarboxylic acid is, for example, citric acid. Another suitable polycarboxylic acid is the homopolymer of acrylic acid. Preferred are the polycarboxylates end capped with sulfonates.

Adjunct Ingredients

The liquid detergent composition herein may optionally comprise a number of other adjunct ingredients such as builders (e.g., preferably citrate), cleaning solvents, cleaning amines, conditioning polymers, cleaning polymers, surface modifying polymers, soil flocculating polymers, structurants, emollients, humectants, skin rejuvenating actives, enzymes, carboxylic acids, scrubbing particles, bleach and bleach activators, perfumes, malodor control agents, pigments, dyes, opacifiers, beads, pearlescent particles, microcapsules, inorganic cations such as alkaline earth metals such as Ca/Mg-ions, antibacterial agents, preservatives, viscosity adjusters (e.g., salt such as NaCl, and other mono-, di- and trivalent salts) and pH adjusters and buffering means (e.g., carboxylic acids such as citric acid, HCl, NaOH, KOH, alkanolamines, phosphoric and sulfonic acids, carbonates such as sodium carbonates, bicarbonates, sesquicarbonates, borates, silicates, phosphates, imidazole and alike).

Method of Washing

Other aspects of the invention are directed to methods of washing soiled articles, especially dishware with the composition of the present invention. Accordingly, there is provided a method of manually washing soiled articles, preferably dishware, comprising the steps of delivering a liquid detergent composition of the invention into a volume of water to form a wash solution and immersing the soiled articles in the solution. Preferably the hydroperoxy fatty acid producing enzymes are present at a concentration of from 0.005 ppm to 15 ppm, preferably from 0.01 ppm to 5 ppm, more preferably from 0.02 ppm to 0.5 ppm, based on active protein, in an aqueous wash liquor during the washing process. As such, the composition herein will be applied in its diluted form to the dishware. Soiled surfaces e.g. dishes are contacted with an effective amount, typically from 0.5 mL to 20 mL (per 25 dishes being treated), preferably from 3 mL to 10 mL, of the liquid detergent composition of the present invention diluted in water. The actual amount of the liquid detergent composition used will be based on the judgment of user, and will typically depend upon factors such as the particular product formulation of the composition, including the concentration of active ingredients in the composition, the number of soiled dishes to be cleaned, the degree of soiling on the dishes, and the like. Generally, from 0.01 mL to 150 mL, preferably from 3 mL to 40 mL of a liquid detergent composition of the invention is combined with from 2,000 mL to 20,000 mL, more typically from 5,000 mL to 15,000 mL of water in a sink having a volumetric capacity in the range of from 1,000 mL to 20,000 mL, more typically from 5,000 mL to 15,000 mL. The soiled dishes are immersed in the sink containing the diluted compositions then obtained, where contacting the soiled surface of the dish with a cloth, sponge, or similar article cleans them. The cloth, sponge, or similar article may be immersed in the liquid detergent composition and water mixture prior to being contacted with the dish surface, and is typically contacted with the dish surface for a period of time ranged from 1 to 10 seconds, although the actual time will vary with each application and user. The contacting of cloth, sponge, or similar article to the surface is preferably accompanied by a concurrent scrubbing of the surface.

Another aspect of the present invention is use of one or more hydroperoxy fatty acid producing enzymes in a liquid detergent composition of the present invention to provide increased suds longevity in an aqueous wash liquor comprising soil. The hydroperoxy fatty acid producing enzymes are selected from the group consisting of: arachidonate lipoxygenases, alpha-dioxygenases, and mixtures thereof, preferably alpha-dioxygenases.

Test Methods

The following assays set forth must be used in order that the invention described and claimed herein may be more fully understood.

Test Method 1—Glass Vial Suds Mileage Method

The objective of the glass vial suds mileage test method is to measure the evolution of suds volume over time generated by a certain solution of liquid detergent composition in the presence of a greasy soil, e.g., olive oil. The steps of the method are as follows:

1. Test solutions are prepared by subsequently adding aliquots at room temperature of: a) 10 g of an aqueous detergent solution at specified detergent concentration and water hardness, b) 1.0 g of an aqueous protein solution at specified concentration and water hardness), and c) 0.11 g of olive oil (Bertolli®, Extra Virgin Olive Oil), into a 40 mL glass vial (dimensions: 95 mm H×27.5 mm D). For the reference samples, the protein solutions are substituted with 1.0 mL of demineralized water.

2. The test solutions are mixed in the closed test vials by stirring at room temperature for 2 minutes on a magnetic stirring plate (IKA, model # RTC B 5001; VWR magnetic stirrer, catalog #58949-012; 500 RPM), followed by manually shaking for 20 seconds with an upwards downwards movement (about 2 up and down cycles per second, +/−30 cm up and 30 cm down).

3. Following the shaking, the test solutions in the closed vials are further stirred on a magnetic stirring plate (IKA, model # RTC B S001; VWR magnetic stirrer, catalog

58949-012; 500 RPM) for 60 minutes inside a water bath at 46° C. to maintain a constant temperature. The samples are then shaken manually for another 20 seconds as described above and the initial suds heights (H1) are recorded with a ruler.

4. The samples are incubated for an additional 30 minutes inside the water bath at 46° C. while stirring (IKA, model # RTC B S001; VWR magnetic stirrer, catalog #58949-012; 500 RPM), followed by manual shaking for another 20 seconds as described above. The final suds heights (H2) are recorded.
5. Protein solutions that produce larger suds heights (H1 and H2), preferably combined with lower drops in suds height between H1 and H2, are more desirable.

Test Method 2—Small Sink Suds Mileage Method

The evolution of the suds volume generated by a solution of a liquid detergent composition can be determined while adding soil loads periodically as follows. An aliquot of 500 mL of solution of the liquid detergent composition in 15 dH hard water (final concentration of 0.12 w %, initial temperature 46° C.) is added into a cylindrical container (dimensions: 150 mm D×150 mm H). The container is incubated in a water bath during the test to maintain the temperature of the solution between 46° C. and 40° C. An initial suds volume is generated in the container by mechanical agitation at 135 rpm for 120 seconds with a paddle (dimensions: 50 mm×25 mm) positioned in the middle of the container.

Then, an aliquot of 0.5 mL of greasy soil (composition: see Table 3, 0.5 mL) is dosed into the solution using a 20-mL syringe and an automated pump (KDS Legato 110 Single Syringe I/W Pump), while the paddle rotates into the solution at 135 rpm for 14 seconds. After mixing, the solution is incubated for 166 additional seconds before the next cycle. The soil injecting, paddling, and incubation steps are repeated every 180 seconds until the end-point is reached and the amount of soil additions needed is recorded. The end-point occurs when a clear suds-free ring that circles the impeller at last half way around is observed two or more consecutive times. The complete process is repeated at least 3 times and the average of the number of additions for all the replicates is calculated for each liquid detergent composition.

Finally, the suds mileage index is then calculated as: (average number of soil additions for test liquid detergent composition)/(average number of soil additions for reference liquid detergent composition)×100. Pending on the test purpose the skilled person could choose to select an alternative water hardness, solution temperature, product concentration or soil type.

TABLE 3

Greasy Soil Composition

| Ingredient | Weight % |
| --- | --- |
| Crisco oil | 12.730 |
| Crisco shortening | 27.752 |
| Lard | 7.638 |
| Refined Rendered Edible Beef Tallow | 51.684 |
| Oleic Acid, 90% (Techn) | 0.139 |
| Palmitic Acid, 99+% | 0.036 |
| Stearic Acid, 99+% | 0.021 |

Test Method 3—Large Sink Suds Mileage Method

The evolution of the suds volume generated by a solution of a liquid detergent composition can be determined while adding soil loads periodically as follows. A stream of hard water (15 dH) fills a sink (cylinder dimensions: 300 mm D×288 mm H) to 4 L with a constant pressure of 4 bar. Simultaneously, an aliquot of the liquid detergent composition (final concentration 0.12 w %) is dispensed through a pipette with a flow rate of 0.67 mL/sec at a height of 37 cm above the bottom of the sink surface. An initial suds volume is generated in the sink due to the pressure of the water. The temperature of the solution is maintained at 46° C. during the test.

After recording the initial suds volume (average suds height×sink surface area), a fixed amount of greasy soil (composition: see Table 3, 4 mL) is injected in the middle of the sink, while a paddle (dimensions: 10 cm×5 cm, positioned in the middle of the sink at the air liquid interface at an angle of 45 degrees) rotates 20 times into the solution at 85 rpm. This step is followed immediately by another measurement of the total suds volume. The soil injecting, paddling, and measuring steps are repeated until the measured suds volume reaches a minimum level, which is set at 400 cm$^3$. The amount of soil additions needed to get to that level is recorded. The complete process is repeated a number of times and the average of the number of additions for all the replicates is calculated for each liquid detergent composition.

Finally, the suds mileage index is then calculated as: (average number of soil additions for test liquid detergent composition)/(average number of soil additions for reference liquid detergent composition)×100.

Pending on the test purpose the skilled person could choose to select an alternative water hardness, solution temperature, product concentration or soil type.

EXAMPLES

The following examples are provided to further illustrate the present invention and are not to be construed as limitations of the present invention, as many variations of the present invention are possible without departing from its spirit or scope.

Example 1a—*Arabidopsis thaliana* Alpha Dioxygenase 2 (Alpha DOX2) Q9C9U3

A codon optimized gene (SEQ ID NO: 18) encoding for a *Arabidopsis thaliana* alpha dioxygenase 2 (Alpha DOX2) variant, including an N-terminal amino acid sequence containing a His-tag, a MBP tag and a TEV protease cleavage site (SEQ ID NO: 19), is designed and synthesized. After gene synthesis, the protein is expressed and purified by Genscript (Piscataway, N.J.). In brief, the complete synthetic gene sequence is subcloned into a pET28a vector for heterologous expression. *Escherichia coli* BL21 (DE3) cells are transformed with the recombinant plasmid and a single colony is inoculated into TB medium containing kanamycin at 37° C. When the OD600 reaches about 3.8, protein expression is induced by adding isopropyl β-D-1-thiogalactopyranoside (IPTG) (final concentration 0.1 mM) and 6-aminolevulinic acid (final concentration 0.25 mM). Cultures are incubated at 16° C. for 16 h at 200 rpm. Cells are harvested by centrifugation and the pellets are lysed by sonication. After centrifugation, the supernatant is collected and the protein is purified by one-step purification using a nickel affinity column and standard protocols known in the art. The protein is stored in 1X PBS buffer (pH 7.4) containing 10% glycerol. The final protein concentration is 0.58 mg/mL as determined by Bradford protein assay with BSA as a standard (ThermoFisher, catalog #23236) and the purity is about 60% as estimated by densitometric analysis of the Coomassie Blue-stained SDS-PAGE gel under reducing conditions.

Example 1b—*Arabidopsis thaliana* Alpha Dioxygenase 1 (Alpha DOX1) Q9SGH6

A codon optimized gene (SEQ ID NO: 20) encoding for a *Arabidopsis thaliana* alpha dioxygenase 1 (Alpha DOX1) variant, including an N-terminal amino acid sequence containing a His-tag, a MBP tag and a TEV protease cleavage site (SEQ ID NO: 21), is designed and synthesized. After gene synthesis, the protein is expressed and purified by Genscript (Piscataway, N.J.). In brief, the complete synthetic gene sequence is subcloned into a pET28a vector for heterologous expression. *Escherichia coli* BL21 (DE3) cells are transformed with the recombinant plasmid and a single colony is inoculated into TB medium containing kanamycin at 37° C. When the OD600 reaches about 4, protein expression is induced by adding isopropyl β-D-1-thiogalactopyranoside (IPTG) (final concentration 0.1 mM) and 6-aminolevulinic acid (final concentration 0.25 mM). Cultures are incubated at 16° C. for 16 h at 200 rpm. Cells are harvested by centrifugation and the pellets are lysed by sonication. After centrifugation, the supernatant is collected and the protein is purified by one-step purification using a nickel affinity column and standard protocols known in the art. The protein is stored in 1×PBS buffer (pH 7.4) containing 10% glycerol. The final protein concentration is 1.58 mg/mL as determined by Bradford protein assay with BSA as a standard (ThermoFisher, catalog #23236) and the purity is about 80% as estimated by densitometric analysis of the Coomassie Blue-stained SDS-PAGE gel under reducing conditions.

Example 1c—*Oryza sativa* Fatty Acid Alpha-Dioxygenase Q9M5J1

A codon optimized gene (SEQ ID NO: 22) encoding for a *Oryza sativa* fatty acid alpha-dioxygenase variant, including an N-terminal His-tag sequence (SEQ ID NO: 23), is designed and synthesized. After gene synthesis, the protein is expressed and purified by Genscript (Piscataway, N.J.). In brief, the complete synthetic gene sequence is subcloned into a pET30a vector for heterologous expression. *Escherichia coli* BL21 (DE3) cells are transformed with the recombinant plasmid and a single colony is inoculated into 2×YT medium containing kanamycin at 37° C. When the OD600 reaches about 0.85, protein expression is induced by adding isopropyl β-D-1-thiogalactopyranoside (IPTG) (final concentration 0.1 mM) and 6-aminolevulinic acid (final concentration 0.25 mM). Cultures are incubated at 16° C. for 16 h at 200 rpm. Cells are harvested by centrifugation and the pellets are lysed by sonication. After centrifugation, the supernatant is collected and the protein is purified by one-step purification using a nickel affinity column and standard protocols known in the art. The protein is stored in 1×PBS buffer (pH 7.4) containing 10% glycerol. The final protein concentration is 1.29 mg/mL as determined by Bradford protein assay with BSA as a standard (ThermoFisher, catalog #23236) and the purity is about 85% as estimated by densitometric analysis of the Coomassie Blue-stained SDS-PAGE gel under reducing conditions.

Example 1d—Hydroperoxy Fatty Acid Producing Enzymes Detergent Compositions

The evolution of suds volume generated by a certain solution of liquid detergent composition in presence of a soil, i.e.greasy soil, is followed under specific conditions (e.g., water hardness, solution temperature, detergent concentrations, etc.). The following solutions are prepared:

A. Hard water (15 dH): 0.75 g $MgCl_2.6H_2O$ (Sigma-Aldrich, catalog # M9272), 2.10 g $CaCl_2.6H_2O$ (Sigma-Aldrich, catalog #21108), and 0.689 g $NaHCO_3$(Sigma-Aldrich, catalog #31437) are dissolved in 5 L of demineralized water.

B. Detergent solution of a control reference detergent composition ("solution DG-R") is prepared using Fairy Dark Green, as commercially available in the UK in February 2017, comprising C1213AE0.6S anionic surfactant and C1214-dimethyl amine oxide amphoteric surfactant in a weight %-ratio between 2:1 and 4:1 and between 50% and 85% of water, diluted in hard water (15 dH) prepared as above, at targeted detergent concentration of 0.12%.

C. Greasy soil: A grease soil is prepared according to the composition described in Table 3.

Example 2—Suds Mileage of Alpha-Dioxygenases and Arachidonate Lipoxygenases

Inventive Composition A is an example of a liquid detergent composition according to the present invention, made with a) detergent solution DG-R (prepared as described in Example 1d) and b) diluted samples of purified *Arabidopsis thaliana* alpha dioxygenase 2 (Alpha DOX2) (prepared as described in Example 1a).

Inventive Composition B is an example of a liquid detergent composition according to the present invention, made with a) detergent solution DG-R (prepared as described in Example 1d) and b) diluted samples of purified *Arabidopsis thaliana* alpha dioxygenase 1 (Alpha DOX1) (prepared as described in Example 1b).

Inventive Composition C is an example of a liquid detergent composition according to the present invention, made with a) detergent solution DG-R (prepared as described in Example 1d) and b) diluted samples of purified *Oryza sativa* fatty acid alpha-dioxygenase (prepared as described in Example 1c).

Inventive Composition D is an example of a liquid detergent composition according to the present invention, made with a) detergent solution DG-R (prepared as described in Example 1d) and b) diluted samples of purified *Homo sapiens* Arachidonate 5-lipoxygenase (EC 1.13.11.34), obtained from Sigma-Aldrich (catalog #437996).

Comparative Composition E contains the same detergent solution DG-R in the absence of enzymes.

The compositions were tested using the small sink suds mileage method (Test Method 2), as described in the test methods section. The results are shown in Table 4.

TABLE 4

| Suds Mileage | | |
|---|---|---|
| | Enzyme Concentration in the Composition [ppm] | Suds Mileage Index |
| Inventive Composition A | 1.2 | 132 |
| Inventive Composition B | 1.2 | 114 |
| Inventive Composition C | 1.2 | 117 |
| Inventive Composition D | 6.0 | 132 |
| Comparative Composition E | 0.0 | 100 |

The results in Table 4 confirm that detergent Inventive Compositions A to D comprising alpha-dioxygenases and arachidonate lipoxygenases according to the invention have a superior suds profile over the entire washing process as single variably compared to Comparative Composition E without the enzymes.

Example 3: Exemplary Liquid Manual Dish-Washing Detergent Composition

Liquid manual dish-washing detergent compositions comprising *Arabidopsis thaliana* Alpha-dioxygenases (SEQ ID NO: 2) or *Homo sapiens* Arachidonate 5-lipoxygenase (SEQ ID NO: 7) according to the invention are shown in Table 5.

TABLE 5

Liquid Detergent Compositions

| Ingredient | Exemplary Comp. 1 (Wt %) | Exemplary Comp. 2 (Wt %) |
| --- | --- | --- |
| Sodium alkyl ethoxy sulfate (C1213EO0.6S) | 22.91% | 22.91% |
| n-C12-14 Di Methyl Amine Oxide | 7.64% | 7.64% |
| Lutensol ® XP80 (non-ionic surfactant supplied by BASF) | 0.45% | 0.45% |
| Sodium Chloride | 1.2% | 1.2% |
| Poly Propylene Glycol (MW 2000) | 1% | 1% |
| Ethanol | 2% | 2% |
| Sodium Hydroxide | 0.24% | 0.24% |
| *Arabidopsis thaliana* Alpha-dioxygenases (SEQ ID NO: 2) | 0.1% | — |
| *Homo sapiens* arachidonate 5-lipoxygenase (SEQ ID NO: 7) | — | 0.1% |
| Minors (perfume, preservative, dye) + water | To 100% | To 100% |
| pH (@ 10% solution) | 9 | 9 |

All percentages and ratios given for enzymes are based on active protein. All percentages and ratios herein are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid detergent composition comprising:
one or more hydroperoxy fatty acid producing enzymes, wherein the one or more hydroperoxy fatty acid producing enzymes are alpha-dioxygenases
b) a surfactant system comprising one or more anionic surfactants and one or more co-surfactants selected from the group consisting of amphoteric surfactant, zwitterionic surfactant, and mixtures thereof, wherein the weight ratio of the anionic surfactants to the co-surfactants is less than about 9:1; and
c) from about 30 wt % to about 95 wt % by weight of the composition, of water;
wherein the alpha-dioxygenases provide increased suds longevity in an aqueous wash liquor comprising greasy soil.

2. The composition according to claim 1, wherein the surfactant system comprises the anionic surfactant and co-surfactant in a weight ratio of the anionic surfactants to the co-surfactants of from 4:1 to 2:1.

3. The composition according to claim 1, wherein the composition is a liquid manual dishwashing composition.

4. The composition according to claim 1, wherein the alpha-dioxygenases are selected from the group consisting of *Arabidopsis thaliana* alpha-dioxygenases (SEQ ID NO: 1), *Arabidopsis thaliana* alpha-dioxygenases (SEQ ID NO: 2), *Fusarium graminearum* alpha-dioxygenases (SEQ ID NO: 3), *Fusarium verticillioides* alpha-dioxygenases (SEQ ID NO: 4), *Fusarium oxysporum* alpha-dioxygenases (SEQ ID NO: 5), *Oryza sativa* alpha-dioxygenases (SEQ ID NO: 6), and variants thereof which exhibit alpha-dioxygenase activity.

5. The composition according to claim 4, wherein the alpha-dioxygenases are selected from the group consisting of *Arabidopsis thaliana* alpha-dioxygenases (SEQ ID NO: 2), and variants thereof which exhibit alpha-dioxygenase activity.

6. The composition according to claim 1, further comprising one or more co-enzymes selected from the group consisting of fatty-acid peroxidases (EC 1.11.1.3), unspecific peroxygenases (EC 1.11.2.1), plant seed peroxygenases (EC 1.11.2.3), fatty acid peroxygenases (EC1.11.2.4), linoleate diol synthases (EC 1.13.11.44), 5,8-linoleate diol synthases (EC 1.13.11.60 and EC 5.4.4.5), 7,8-linoleate diol synthases (EC 1.13.11.60 and EC 5.4.4.6), 9,14-linoleate diol synthases (EC 1.13.11.B1), 8,11-linoleate diol synthases, oleate diol synthases, other linoleate diol synthases, unspecific monooxygenase (EC 1.14.14.1), alkane 1-monooxygenase (EC 1.14.15.3), oleate 12-hydroxylases (EC 1.14.18.4), fatty acid amide hydrolase (EC 3.5.1.99), oleate hydratases (EC 4.2.1.53), linoleate isomerases (EC 5.2.1.5), linoleate (10E,12Z)-isomerases (EC 5.3.3.B2), fatty acid decarboxylases (OleT-like), iron-dependent decarboxylases (UndA-like), amylases, lipases, proteases, cellulases, and mixtures thereof.

7. The composition according to claim 6, wherein the co-enzyme is selected from the group consisting of fatty-acid peroxidases (EC 1.11.1.3), unspecific peroxygenases (EC 1.11.2.1), plant seed peroxygenases (EC 1.11.2.3), and fatty acid peroxygenases (EC1.11.2.4), and mixtures thereof.

8. The composition according to claim 1, wherein the hydroperoxy fatty acid producing enzymes are present in an amount of from about 0.0001 wt % to about 1 wt %, by weight of the detergent composition, based on active protein.

9. The composition according to claim 1, wherein the surfactant system is present in an amount of from about 1 wt % to about 60 wt %, by weight of the detergent composition.

10. The composition according to claim 1, wherein the anionic surfactants are selected from the group consisting of alkyl sulfates, alkyl alkoxy sulfates, alkyl benzene sulfonates, paraffin sulfonates, and mixtures thereof.

11. The composition according to claim 1, wherein the co-surfactant is an amphoteric surfactant which is an amine oxide surfactant.

12. The composition according to claim 1, wherein the anionic surfactants are a mixture of alkyl sulfates and alkyl alkoxy sulfates, the co-surfactants are alkyl dimethyl amine oxides, and wherein the weight ratio of the anionic surfactants to the co-surfactants is from about 4:1 to about 2:1.

13. The composition according to claim 1, further comprising one or more non-ionic surfactants.

14. The composition according to claim 1, further comprising an enzyme stabilizer selected from the group consisting of chemical and physical stabilizers.

15. A method of manually washing soiled dishware, comprising the step of delivering a composition according to claim 1 into a volume of water to form a wash solution and immersing the soiled dishware in the wash solution, wherein the hydroperoxy fatty acid producing enzymes are present at a concentration of from about 0.005 ppm to about 15 ppm, based on active protein, in the wash solution during the washing process.

16. The composition according to claim 1, wherein the alpha-dioxygenases have at least about 95% identity as calculated over the entire length of a sequence aligned against the entire length of at least one reference sequence selected from the group consisting of *Arabidopsis thaliana* alpha-dioxygenases (SEQ ID NO: 1), *Arabidopsis thaliana* alpha-dioxygenases (SEQ ID NO: 2), *Fusarium graminearum* alpha-dioxygenases (SEQ ID NO: 3), *Fusarium verticillioides* alpha-dioxygenases (SEQ ID NO: 4), *Fusarium oxysporum* alpha-dioxygenases (SEQ ID NO: 5), and *Oryza sativa* alpha-dioxygenases (SEQ ID NO: 6).

17. The composition according to claim 16, wherein the alpha-dioxygenases have at least about 95% identity as calculated over the entire length of a sequence aligned against the entire length of a reference sequence which is *Arabidopsis thaliana* alpha-dioxygenases (SEQ ID NO: 2).

\* \* \* \* \*